US012584098B2

(12) United States Patent
Tramontano et al.

(10) Patent No.: US 12,584,098 B2
(45) Date of Patent: Mar. 24, 2026

(54) IN-VITRO MODEL OF THE HUMAN GUT MICROBIOME AND USES THEREOF IN THE ANALYSIS OF THE IMPACT OF XENOBIOTICS

(71) Applicant: EUROPEAN MOLECULAR BIOLOGY LABORATORY, Heidelberg (DE)

(72) Inventors: Melanie Tramontano, Heidelberg (DE); Kiran Raosaheb Patil, Heidelberg (DE); Martina Klünemann, Heidelberg (DE); Mihaela Pruteanu, Berlin (DE); Lisa Maier, Heidelberg (DE); Michael Kuhn, Heidelberg (DE); Sergej Andrejev, Heidelberg (DE); Yongkyu Kim, Heidelberg (DE); Peer Bork, Heidelberg (DE); Athanasios Typas, Heidelberg (DE); Georg Zeller, Heidelberg (DE)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 0 days.

(21) Appl. No.: 16/966,322

(22) PCT Filed: Feb. 6, 2019

(86) PCT No.: PCT/EP2019/052836
§ 371 (c)(1),
(2) Date: Jul. 30, 2020

(87) PCT Pub. No.: WO2019/154823
PCT Pub. Date: Aug. 15, 2019

(65) Prior Publication Data
US 2020/0370005 A1 Nov. 26, 2020

(30) Foreign Application Priority Data
Feb. 6, 2018 (EP) ..................................... 18155278

(51) Int. Cl.
| | |
|---|---|
| *C12N 1/20* | (2006.01) |
| *C12Q 1/02* | (2006.01) |
| *C12Q 1/04* | (2006.01) |

(52) U.S. Cl.
CPC .............. *C12N 1/20* (2013.01); *C12Q 1/025* (2013.01); *C12Q 1/04* (2013.01)

(58) Field of Classification Search
CPC ............. C12Q 1/04; C12Q 1/025; C12N 1/20
See application file for complete search history.

(56) References Cited

U.S. PATENT DOCUMENTS 9,028,841 B2 * 5/2015 Henn ..................... A61K 35/74
435/252.4

FOREIGN PATENT DOCUMENTS

| WO | WO-2012122522 A2 * | 9/2012 | .............. C12N 1/20 |
|---|---|---|---|
| WO | 2015051323 A1 | 4/2015 | |
| WO | 2016049932 A1 | 4/2016 | |
| WO | 2016079731 A2 | 5/2016 | |

OTHER PUBLICATIONS

Venema K, van den Abbeele P. Experimental models of the gut microbiome. Best Pract Res Clin Gastroenterol. Feb. 2013;27(1): 115-26. doi: 10.1016/j.bpg.2013.03.002. PMID: 23768557. (Year: 2013).*

Spiegelman, D., Whissell, G., & Greer, C. W. (2005). A survey of the methods for the characterization of microbial consortia and communities. Canadian Journal of Microbiology, 51(5), 355-386 (Year: 2005).*

Atlas, R. M. (2004). Handbook of microbiological media. CRC press (Year: 2004).*

Rettedal, Elizabeth A., Heidi Gumpert, and Morten OA Sommer. "Cultivation-based multiplex phenotyping of human gut microbiota allows targeted recovery of previously uncultured bacteria." Nature communications 5.1 (2014): 1-9 (Year: 2014).*

Kaneko, Tsutomu, et al. "Growth stimulator for bifidobacteria produced by Propionibacterium freudenreichii and several intestinal bacteria." Journal of dairy science 77.2 (1994): 393-404 (Year: 1994).*

Baron, Ellen Jo. "Bilophila wadsworthia: a unique Gram-negative anaerobic rod." Anaerobe 3.2-3 (1997): 83-86. (Year: 1997).*

Gotoh, Aina, et al.: "Use of Gifu Anaerobic Medium for Culturing 32 Dominant Species of Human Gut Microbes and its Evaluation Based on Short-Chain Fatty Acids Fermentation Profiles", Bioscience, Biotechnology, and Biochemistry, vol. 81, No. 10, Oct. 3, 2017, pp. 2009-2017.

Klünemann, Martina, et al.: "Computational tools for modeling xenometabolism of the human gut microbiota", Trends in Biotechnology, Elsevier Publications, Cambridge, GB, vol. 32, No. 3, Mar. 2014, pp. 157-165.

(Continued)

*Primary Examiner* — Robert J Yamasaki
*Assistant Examiner* — Trevor Kane
(74) *Attorney, Agent, or Firm* — SALIWANCHIK, LLOYD & EISENSCHENK

(57) ABSTRACT

The present invention relates to an in-vitro model of the human gut microbiome, the model comprising a culture of the gut microbiome, wherein the model has a cumulative enzymatic coverage of more than 85% of the gut microbiome of a healthy human. The model facilitates metabolic modeling and enables a better understanding of the structure and function of the human gut microbiome as well as of modifications of xenobiotics by intrinsic gut microbiota, such as biotransformation and bioaccumulation. It can further be used to study the effects of variations in nutritional conditions. Importantly, the invention can also be used for diagnosing a disease, such as a gastrointestinal disorder, a proliferative disease, a metabolic disorder, a cardiovascular disease, an immunological disease, and an infectious disease.

11 Claims, 37 Drawing Sheets

(56)                    References Cited

OTHER PUBLICATIONS

Li, Leyuan, et al.: "Evaluating in Vitro Culture Medium of Gut Microbiome with Orthogonal Experimental Design and a Metaproteomics Approach", Journal of Proteome Research, vol. 17, Nov. 13, 2017, pp. 154-163.

Maier, Lisa, et al.: "Extensive impact of non-antibiotic drugs on human gut bacteria", Nature, vol. 555, Mar. 29, 2018, pp. 623-648.

Medina, Daniel A., et al.: "Prebiotics Mediate Microbial Interactions in a Consortium of the Infant Gut Microbiome", International Journal of Molecular Sciences, vol. 18, Oct. 4, 2017, pp. 1-16.

Sommer, Morten OA: "Advancing gut microbiome research using cultivation", Current Opinion in Microbiology, vol. 27, 2015, pp. 127-132.

Venema, Koen, et al.: "Experimental models of the gut microbiome", Best Practice and Research: Clinical Gastroenterology, vol. 27, Jan. 1, 2013, pp. 115-126.

* cited by examiner

Correlation (spearman)

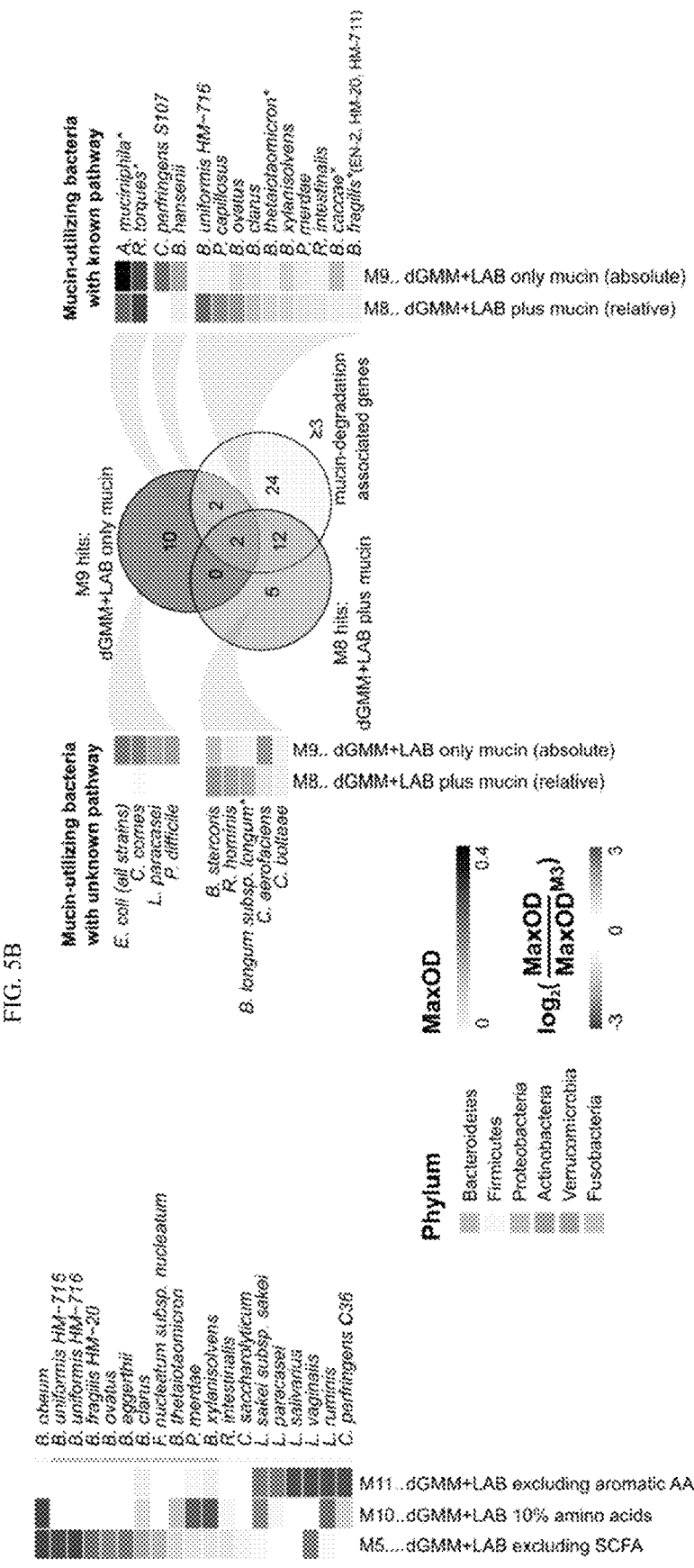

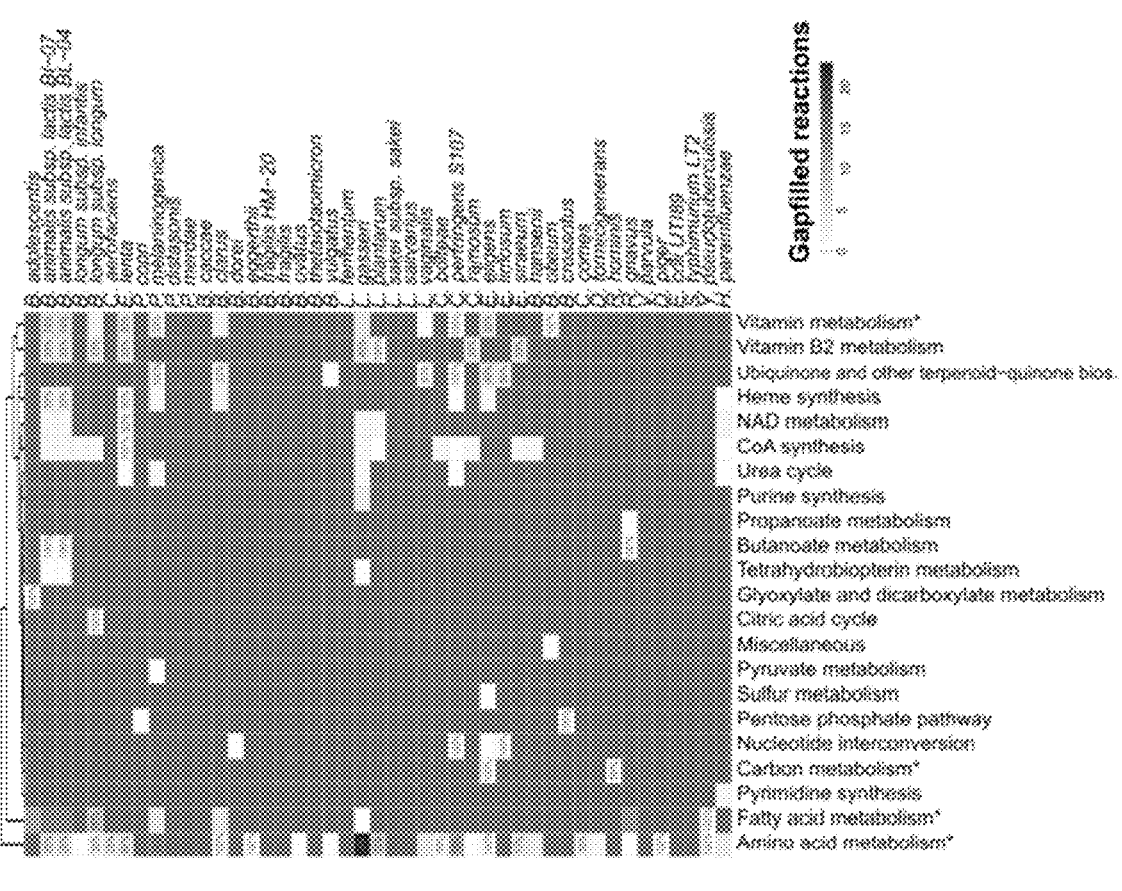
FIG. 9B
FIG. 9A
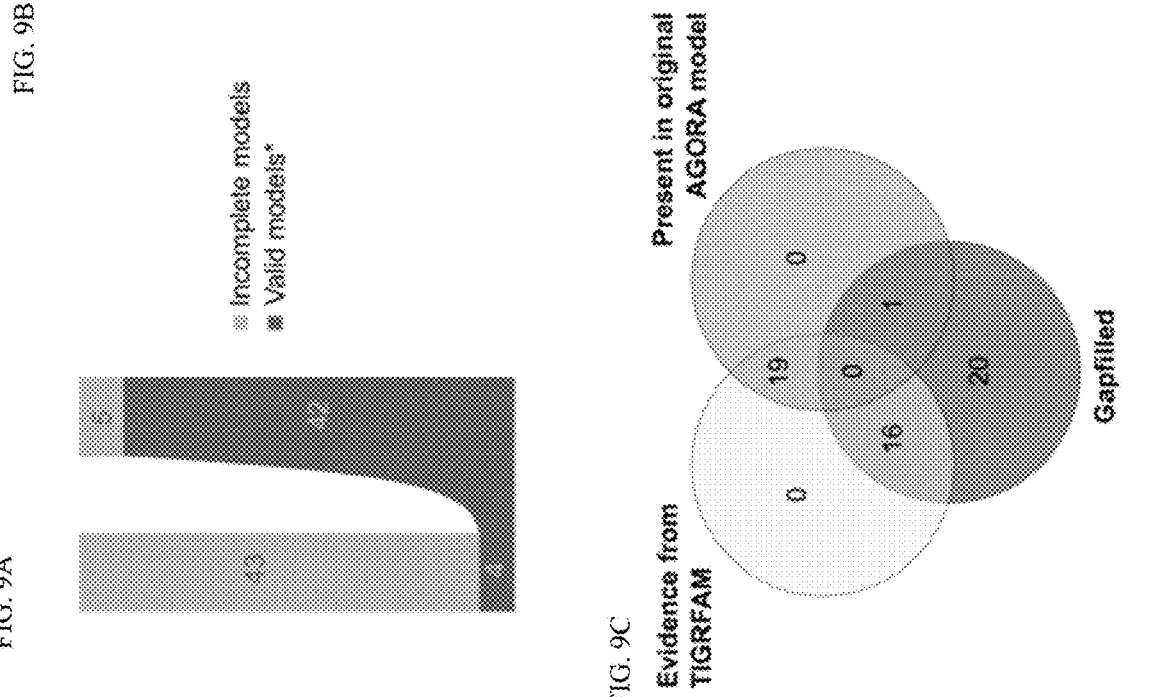
FIG. 9C

FIG. 10B
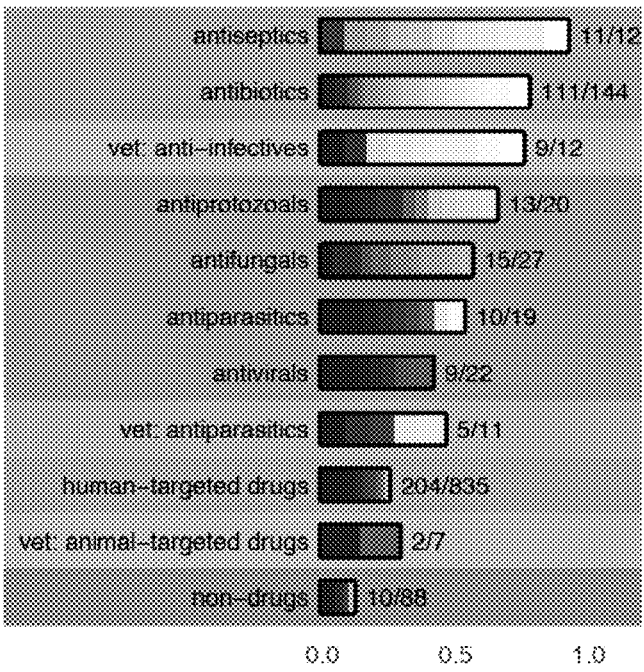
Fraction of drugs with anticommensal activity
Number of affected strains
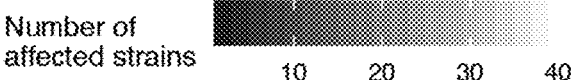
FIG. 10C
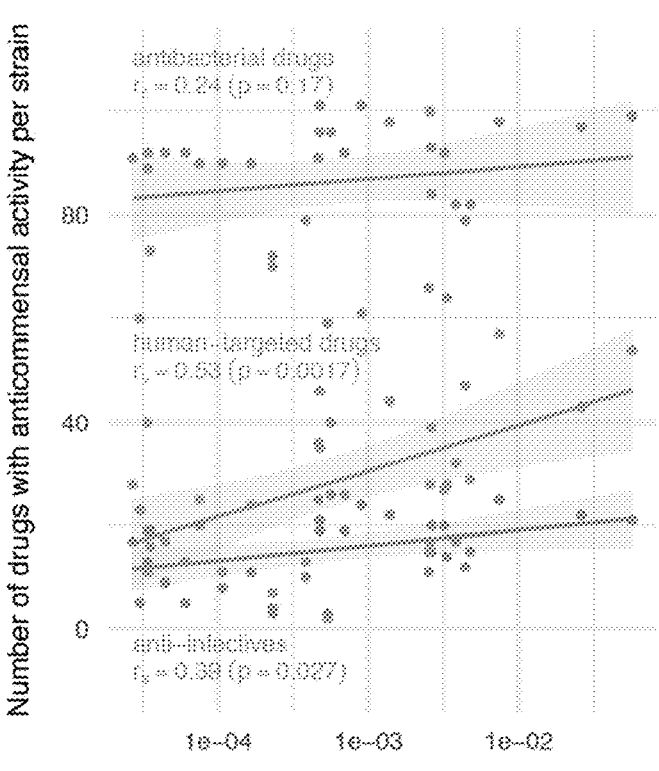
Relative abundance

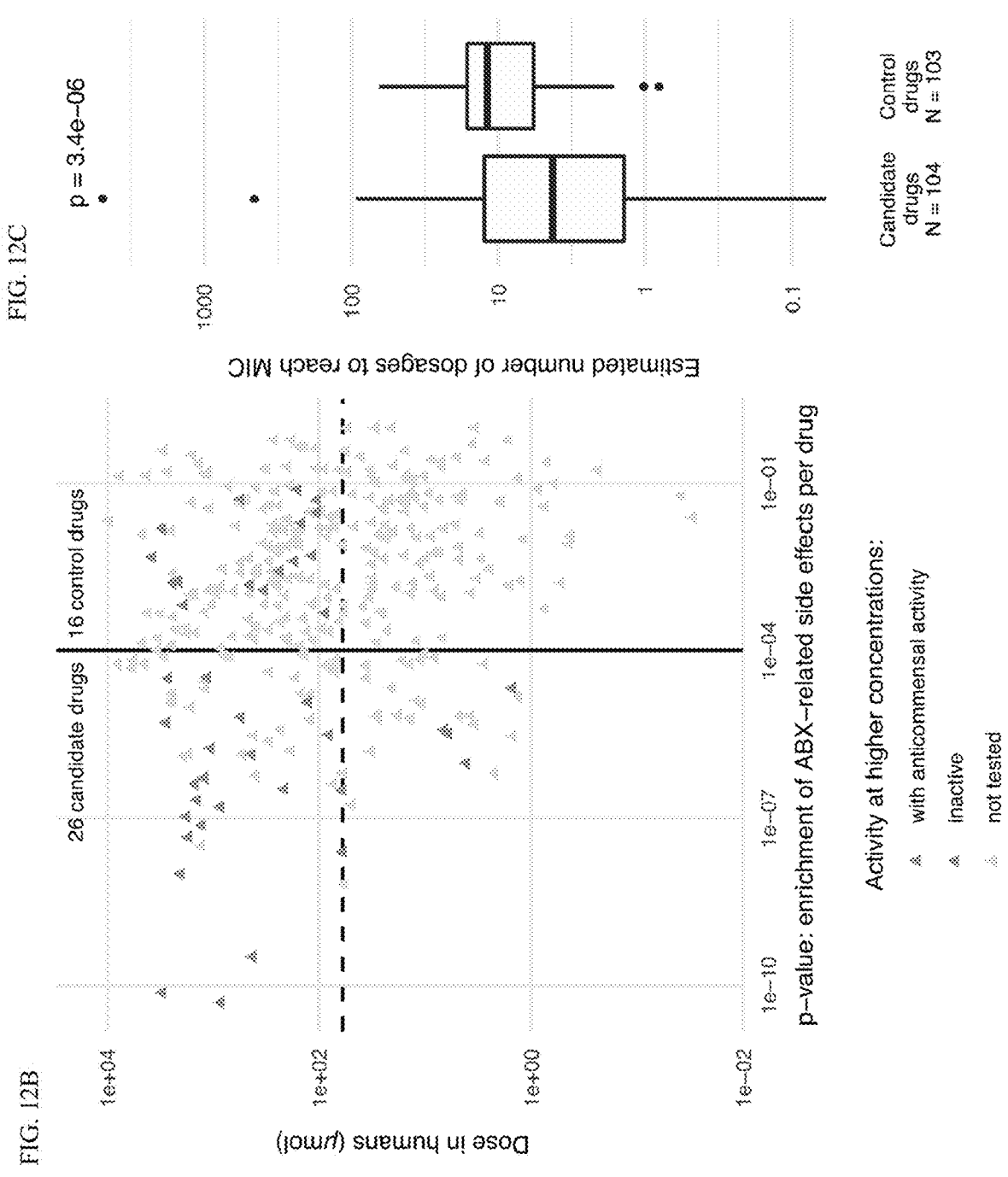

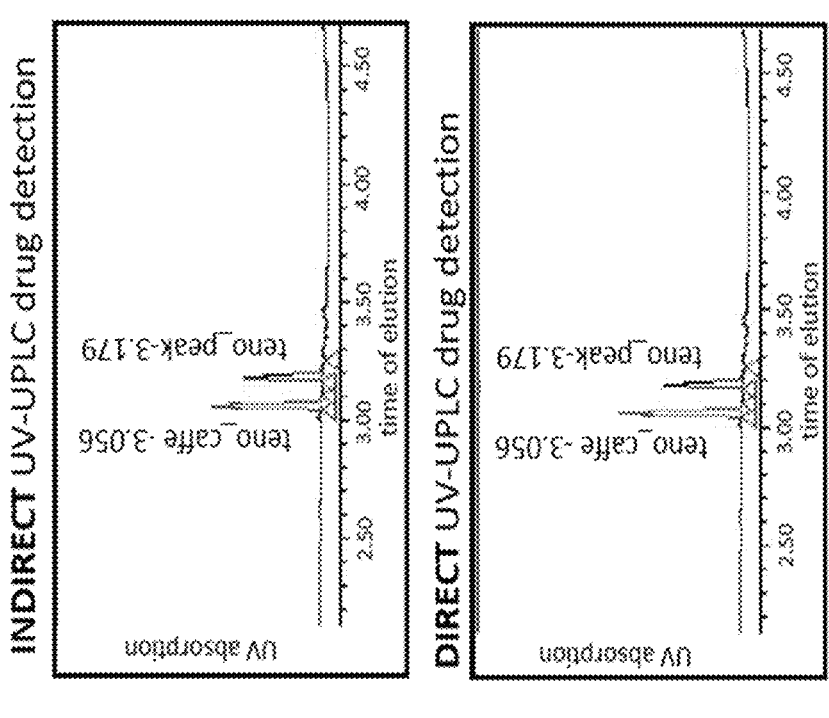
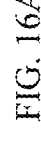
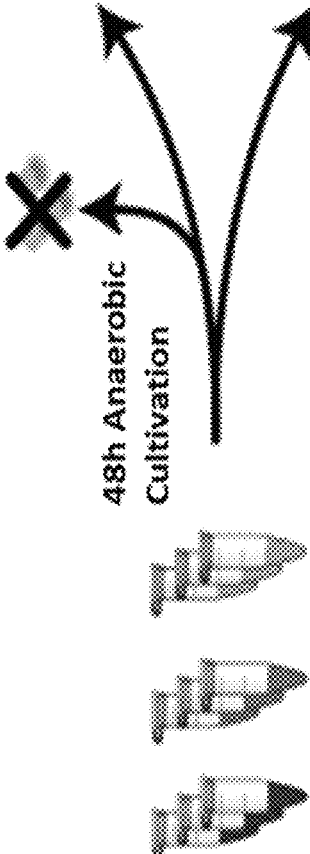
FIG. 16A

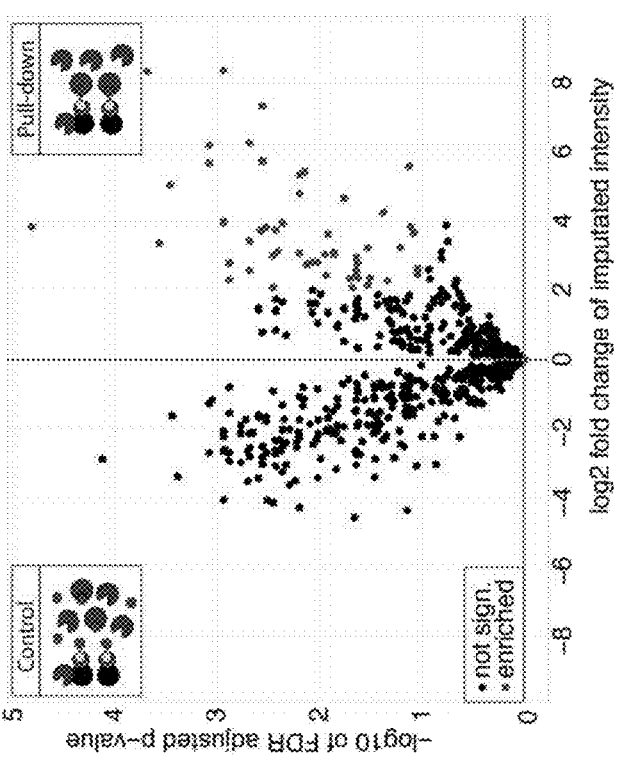
FIG. 17C
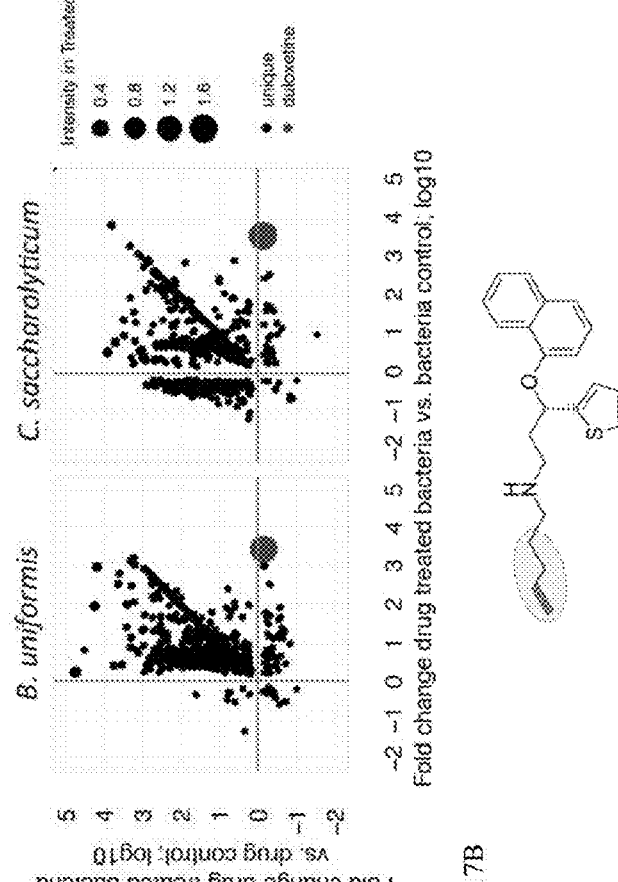
FIG. 17A
FIG. 17B

IN-VITRO MODEL OF THE HUMAN GUT MICROBIOME AND USES THEREOF IN THE ANALYSIS OF THE IMPACT OF XENOBIOTICS

CROSS REFERENCE TO RELATED APPLICATIONS

This application is a National Stage Application of International Application Number PCT/EP2019/052836, filed Feb. 6, 2019; which claims priority to European Application No. 18155278.7, filed Feb. 6, 2018.

The present invention relates to an in-vitro model of the human gut microbiome, the model comprising a culture of the gut microbiome, wherein the model has a cumulative enzymatic coverage of more than 85% of the gut microbiome of a healthy human. The model facilitates metabolic modeling and enables a better understanding of the structure and function of the human gut microbiome as well as of modifications of xenobiotics by intrinsic gut microbiota, such as biotransformation and bioaccumulation. It can further be used to study the effects of variations in nutritional conditions. Importantly, the invention can also be used for diagnosing a disease, such as a gastrointestinal disorder, a proliferative disease, a metabolic disorder, a cardiovascular disease, an immunological disease, and an infectious disease.

BACKGROUND OF THE INVENTION

All pharmaceuticals have both beneficial and undesirable effects. Improving drug efficacy and reducing side effects have paramount medical and economic importance, and hence numerous studies on mode of action (MoA) and off-target spectrum of various drugs are being conducted. The role of the gut microbiota on both these levels is rarely considered despite gastrointestinal side effects being very common for drugs, and the gut microbiome itself being pivotal for human health.

Early in life, the gut is colonized quickly by a remarkable variety of bacteria, archaea, fungi, and viruses. Together, these cells are termed the gut 'microbiome'. Under most circumstances, gut microbes help digest food as well as maintain immune functions in the host. Recent improvements of high-throughput environmental shotgun sequencing techniques enabled an efficient and cost-effective tool for investigating the members of the microbiome. Subsequently, many links between dysfunctions of the human microbiota and diseases such as gastrointestinal disorders, proliferative diseases, metabolic disorders, cardiovascular diseases, immunological diseases, and infectious diseases have been established. Recent progress in the field suggests the use of the microbiome as an early detection biomarker for diseases and makes the human microbiome a target for therapeutic intervention.

The composition of the human gut microbiota is influenced by several host factors including the immune system and life style, but also by metabolic cross-feeding among different bacterial species. Interactions of the microbiota with the host are often mediated by bacterial metabolites such as vitamins, short chain fatty acids, amino acids, neurotransmitters, virulence factors and toxins. For example, specific gut bacteria can cause elevated serum levels of branched-chain amino acids that correlate with insulin resistance in non-diabetic individuals. Several community members, such as *Bacteroides thetaiotaomicron*, are known to be capable of metabolizing complex substrates like mucin, which is critical in understanding their contribution to inflammation and infection through, for example, weakening of the mucosal barrier.

It has been shown recently that therapeutic drugs, designed to target human cells and not microbes, can influence the human microbiota itself, which might be the cause of therapeutic side effects. Those therapeutic drugs included members mainly of four classes: antidiabetics (metformin), proton pump inhibitors (PPIs), nonsteroidal anti-inflammatory drugs (NSAIDs) and atypical antipsychotics. Another study implied a more general role of medication on gut microbiome composition. As it is unclear whether such effects are direct and go beyond the few drug classes studied, the inventors decided it was necessary to systematically profile interactions between drugs and a large number of bacterial species.

The inventors reasoned that such comprehensive knowledge would enable to derive general trends and rules of drug action on the microbiome and serve as resource for the community. Ultimately such knowledge could be used to improve current therapies and facilitate drug design, by opening new paths for controlling side effects and for drug repurposing: new MoAs, tools to modulate the microbiome or scaffolds for new antimicrobials. Even for anti-infectives, used to eradicate pathogens, an understanding of the collateral damage they cause in human gut commensals may lead to more targeted treatments with reduced risks for antibiotic resistance.

Prediction of xenobiotic biotransformation is highly valuable since it can reduce the cost of developing drugs and prevent unnecessary testing for toxicity. Furthermore, together with other data from metagenomic sequencing, this knowledge can foster personalized dosage (for better pharmacokinetics) and personalized medicine, thus reducing side effects. To predict efficacy or potential toxic side effects one has thus to investigate how the xenobiotic metabolism of gut bacteria influences the degradation and absorption of the drugs. The general metabolic processes a xenobiotic compound can potentially undergo in the gut are known in principle. However, the specifics of when, where, and how are often unclear. The biodegradation of a xenobiotic compound is difficult to predict from the compound structure alone, since it is also dependent on the chemical environment and enzyme availability.

Importantly, bacterial metabolism plays a fundamental role in gut microbiota ecology and host microbiome interactions. Yet, metabolic capabilities of most gut bacteria have remained unknown. To examine metabolic capacity and dissect complex metabolic interactions, for example in studies on mode of action (MoA) and off-target spectrum of various drugs, advanced culture based model systems are urgently needed. Most gut bacterial species have so far been grown in complex media of unknown chemical composition and defined media have been described only for a handful of species. This severely limits mechanistic investigations into community functions, e.g. discovering cross-fed metabolites or linking functional metabolites to the producer species. Moreover, computational efforts to reconstruct species and community-level metabolic models critically rely on the availability of defined growth media. Consequently, the mechanistic link between diet, drug and/or inter-species interactions with microbiota composition and dynamics is currently difficult to establish.

There is an urgent demand for advanced culture based model systems of the human gut microbiome as well as media compositions for culturing such gut microbiome model systems. Such models could dissect complex metabolic interactions between host and the human microbiome and enable novel assays for drug screenings and drug design. In particular, such models will enable bacteria-drug interaction screenings and depletion-mode assays, which can reveal how human gut bacteria interact with human-targeted drugs. Using such models could facilitate metabolic modeling and enable a better understanding of the structure and function of the human gut microbiome as well as of modifications of xenobiotics by intrinsic gut microbiota, such as biotransformation and bioaccumulation. Such models can further be used to study the effects of variations in nutritional conditions and for diagnosing a disease, such as a gastro-intestinal disorder, a proliferative disease, a metabolic disorder, a cardiovascular disease, an immunological disease, and an infectious disease.

Innovative culture based model systems of the human gut microbiome are dependent upon identifying a minimal set of bacterial strains needed to represent the gut microbiome of a healthy human subject. However, the recovery of gut bacterial strains from fecal samples is a very complicated process, which has limited the number of gut bacterial strains that have successfully been grown from fecal samples for a long time. The reason for this lies in the fastidious and anaerobic growth requirements of most gut bacterial strains, making microbiota in vitro studies very difficult and time-consuming. As a result, most gut bacterial strains had previously been labeled as 'unculturable'.

Recent scientific advancements led to significant improvements in the development of culturing techniques of gut bacterial strains and enabled the identification and characterization of several so far unidentified gut bacterial strains. For example, Lagier et al. (2015) used microbial culturomics, a culturing approach that uses multiple culture conditions and matrix-assisted laser desorption/ionization— time of flight and 16S rRNA, for identification of a large number of gut bacterial species.

Lau et al. (2016) further combined a culture-based method with 16S rRNA gene sequencing to demonstrate the majority of the bacteria identified by 16S sequencing of the human gut microbiota can indeed be cultured.

Additionally, Browne et al. (2016) used targeted phenotypic culturing linked to large-scale whole-genome sequencing, phylogenetic analysis and computational modelling to demonstrate that a substantial proportion of the intestinal bacteria are culturable.

Recent advances have also been made to mimic growth conditions of the gastrointestinal tract. Kim et al. (2011) compared the bacterial community in three different complex culture media (brain heart infusion broth and high- and low-carbohydrate medium with different growth supplements). However, such rich and complex media prevent mechanistic investigations into community functions, e.g. the discovery of cross-fed metabolites. Thus, it would be of great advantage to characterize the defined growth media compositions needed for culturing of individual gut bacterial strains.

Lopes et al. (1976) described a chemically defined medium for *Veillonella parvula* and *V. alcalescens*. Sebald et al. (1975) determined a defined culture medium for *Clostridium perfringens*, and Neidhardt et al. (1974) further defined a minimal medium for *Escherichia coli* as well as for *Salmonella typhimurium*. Magnusdottir (2017) identified a defined growth medium for *Bacteroides caccae* ATCC 34185 by using AGORA (assembly of gut organisms through reconstruction and analysis), a resource of genome-scale metabolic reconstructions semi-automatically generated for 773 human gut bacteria.

However, no large scale study has been performed so far to identify defined growth conditions needed to culture a panel of gut bacteria representative for the human gut microbiome of a healthy individual. Moreover, the minimal species needed to represent the gut microbiome of a healthy human subject had not been determined prior to this invention.

It is therefore an object of the present invention to generate a culture based model system of the human gut microbiome. It is a further object of this invention to use such a culture based model system for systematic screenings of bacteria thriving in the human gut, for example against drugs. Other objects of the present invention will become apparent to the person of skill when studying the specification of the present invention.

In a first aspect thereof, the object of the present invention is solved by providing an in-vitro model of a gut microbiome, comprising a panel of bacterial species selected from i Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella, and *Bilophila.*

According to the present invention, a "panel" designates a combination of multiple bacterial species that, together, have a cumulative enzymatic coverage of the gut microbiome of a healthy human being. The panel in context of the herein disclosed invention can further contain additional bacterial species.

The present invention pertains to a panel of a plurality of bacterial species as identified herein as having a cumulative enzymatic coverage close to the one of the gut microbiome of a healthy human being. Thus, the advantage of combing the bacterial species disclosed herein is an increased coverage of the human gut microbiome, which is important for further biomedical and pharmaceutical studies.

Hence, in the context of the present invention, a bacterial panel comprising *Bacteroides* as only bacterial species achieves a cumulative enzymatic coverage of almost 50% of the gut microbiome of a healthy human being.

A bacterial panel comprising *Bacteroides* and at least one species selected from *Eubacterium, Alistipes*, and *Ruminococcus* reaches a cumulative enzymatic coverage of over 55% of the human gut microbiome. Thus, a panel comprising *Bacteroides* and *Eubacterium*, or *Bacteroides* and *Alistipes*, or *Bacteroides* and *Ruminococcus* is sufficient to cover at least 55% of the enzymatic activity of the human gut microbiome.

A bacterial panel comprising *Bacteroides, Eubacterium, Alistipes, Ruminococcus*, and at least one species selected from *Roseburia, Parabacteroides*, and *Prevotella* achieves a cumulative enzymatic coverage of at least 60% of the human gut microbiome. Thus, a panel comprising *Bacteroides, Eubacterium, Alistipes, Ruminococcus*, and *Roseburia*, or *Bacteroides, Eubacterium, Alistipes, Ruminococcus*, and *Parabacteroides*, or *Bacteroides, Eubacterium, Alistipes, Ruminococcus*, and *Prevotella* is sufficient to cover at least 60% of the enzymatic activity of the human gut microbiome.

A bacterial panel comprising *Bacteroides, Eubacterium, Alistipes, Ruminococcus, Roseburia, Parabacteroides, Prevotella*, and at least one species selected from *Bifidobacterium, Coprococcus* and *Dorea* achieves a cumulative enzymatic coverage of at least 62.5% of the human gut microbiome.

A bacterial panel comprising *Bacteroides, Eubacterium, Alistipes, Ruminococcus, Roseburia, Parabacteroides, Prevotella, Bifidobacterium, Coprococcus, Dorea*, and at least one species selected from *Blautia*, and *Odoribacter* covers at least 65% of the enzymatic activity of the human gut microbiome.

A bacterial panel comprising *Bacteroides, Eubacterium, Alistipes, Ruminococcus, Roseburia, Parabacteroides, Prevotella, Bifidobacterium, Coprococcus, Dorea, Blautia, Odoribacter*, and *Clostridium* achieves a cumulative enzymatic coverage of at least 70% of the human gut microbiome.

A bacterial panel comprising *Bacteroides, Eubacterium, Alistipes, Ruminococcus, Roseburia, Parabacteroides, Prevotella, Bifidobacterium, Coprococcus, Dorea, Blautia, Odoribacter, Clostridium* and *Streptococcus* achieves a cumulative enzymatic coverage of at least 72.5% of the human gut microbiome.

A bacterial panel comprising *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus*, and *Collinsella* reaches a cumulative enzymatic coverage of at least 80% of the human gut microbiome.

A bacterial panel comprising *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella*, and *Bilophila* reaches a cumulative enzymatic coverage of at least 85% of the human gut microbiome.

A bacterial panel comprising *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella, Bilophila* and at least one species selected from *Escherichia*, and *Akkermansia*, reaches a cumulative enzymatic coverage of at least 87.5% of the human gut microbiome.

A bacterial panel comprising *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella, Bilophila, Escherichia, Akkermansia*, and at least one species selected from *Veillonella, Haemophilus, Desulfovibrio*, and *Butyrivibrio* achieves a cumulative enzymatic coverage of at least 90% of the gut microbiome of a healthy human being.

Thus, one, two, three, four, five, six, seven, eight, nine, ten, eleven, twelve, thirteen, fourteen, fifteen, sixteen, seventeen, eighteen, nineteen, twenty, twenty-one, or twenty-two bacterial species are combined to achieve a cumulative enzymatic coverage of at least 50%, 55%, 60%, 62.5%, 65%, 70%, 72.5%, 80%, 85%, 87.5%, or 90% of the gut microbiome of a healthy human being.

Alternatively or additionally to the preferred embodiments, the panel of the invention may be characterized by an enzymatic coverage of at least 50%, preferably at least 55%, more preferably at least 60%, more preferably at least 62.5%, more preferably at least 65%, more preferably at least 70%, more preferably at least 72.5%, more preferably at least 80%, more preferably at least 85%, more preferably at least 87.5%, or most preferably at least 90% of the gut microbiome of a healthy human being.

Preferred is that at least two bacterial species are combined to the panel of the present invention. More preferred at least five bacterial species are combined. More preferred at least eight bacterial species are combined. More preferred at least eleven bacterial species are combined. More preferred at least thirteen bacterial species are combined. More preferred at least fourteen bacterial species are combined. More preferred at least fifteen bacterial species are combined. More preferred, at least sixteen bacterial species are combined. More preferred at least seventeen bacterial species are combined. More preferred at least nineteen bacterial species are combined. Most preferred at least twenty-two bacterial species are combined.

One specifically preferred panel in context of the herein disclosed invention comprises bacterial species selected from *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella*, and *Bilophila*.

In a specifically preferred embodiment, the in-vitro model according to the present invention has a cumulative enzymatic coverage of more than 85% of the gut microbiome of a healthy human.

In another preferred embodiment, the in-vitro model of the present invention can further comprise at least one bacterial species selected from *Escherichia, Akkermansia, Veillonella, Haemophilus, Desulfovibrio*, and *Butyrivibrio*.

The most preferred embodiment of the invention relates to a panel of all bacterial species, optionally wherein 1 or 2 bacterial species are substituted with others, or omitted. The complete set of all bacterial species selected from *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella, Bilophila, Escherichia, Akkermansia, Veillonella, Haemophilus, Desulfovibrio*, and *Butyrivibrio* is the most preferred panel of the invention.

Preferred is an in-vitro model according to the present invention, wherein said species are selected from *Bacteroides caccae, Bacteroides clarus, Bacteroides coprocola, Bacteroides dorei* or *Bacteroides vulgatus, Bacteroides eggerthii, Bacteroides fragilis, Bacteroides ovatus, Bacteroides thetaiotaomicron, Bacteroides xylanisolvens, Bacteroides stercoris, Bacteroides uniformis, Eubacterium eligens, Eubacterium rectale, Eubacterium siraeum, Alistipes putredinis, Alistipes shahii, Ruminococcus gnavus, Ruminococcus torques, Ruminoccocus bromii, Ruminococcus obeum, Roseburia hominis, Roseburia intestinalis, Parabacteroides distasonis, Parabacteroides merdae, Prevotella copri, Bifidobacterium adolescentis, Bifidobacterium longum, Coprococcus comes, Dorea formicigenerans, Blautia hansenii, Odoribacter splanchnicus, Clostridium bolteae, Clostridium leptum, Clostridium ramosum, Streptococcus parasanguinis, Streptococcus salivarius, Collinsella aerofaciens, Bilophila wadsworthia, Escherichia coli, Akkermansia muciniphila, Veillonella parvula, Haemophilus parainfluenzae, Desulfovibrio piger*, and *Butyrivibrio crossotus*.

The present invention further relates to a medium kit for culturing bacteria of the human gut microbiome, comprising at least one of gut microbiota medium (GMM), modified Gifu anaerobic medium broth (mGAM), mGAM comprising hemin and ß-NAD (mGAM++), GMM+mGAM, brain heart infusion broth comprising hemin and ß-NAD (BHI++), defined gut microbiota medium (dGMM), lactic acid bacteria (LAB) medium, dGMM and LAB medium, dGMM and LAB medium comprising a reduced amount of minerals and vitamins, dGMM and LAB medium excluding short chain fatty acids (SOFA), dGMM and LAB medium comprising monosaccharides as only carbohydrate source, dGMM and LAB medium comprising Mucin, dGMM and LAB medium comprising Mucin as only carbohydrate source, dGMM and LAB medium comprising only 10% amino acids, and dGMM and LAB medium excluding aromatic amino acids.

The media composition of the present invention is disclosed in table 2.

Thus, in context of the herein disclosed invention a medium kit can comprise any number of media selected from gut microbiota medium (GMM), modified Gifu anaerobic medium broth (mGAM), mGAM comprising hemin and ß-NAD (mGAM++), GMM+mGAM, brain heart infusion broth comprising hemin and ß-NAD (BHI++), defined gut microbiota medium (dGMM), lactic acid bacteria (LAB) medium, dGMM and LAB medium, dGMM and LAB medium comprising a reduced amount of minerals and vitamins, dGMM and LAB medium excluding short chain fatty acids (SOFA), dGMM and LAB medium comprising monosaccharides as only carbohydrate source, dGMM and LAB medium comprising Mucin, dGMM and LAB medium comprising Mucin as only carbohydrate source, dGMM and LAB medium comprising only 10% amino acids, and dGMM and LAB medium excluding aromatic amino acids.

Moreover, any media selected from gut microbiota medium (GMM), modified Gifu anaerobic medium broth (mGAM), mGAM comprising hemin and ß-NAD (mGAM++), GMM+mGAM, brain heart infusion broth comprising hemin and ß-NAD (BHI++), defined gut microbiota medium (dGMM), lactic acid bacteria (LAB) medium, dGMM and LAB medium, dGMM and LAB medium comprising a reduced amount of minerals and vitamins, dGMM and LAB medium excluding short chain fatty acids (SOFA), dGMM and LAB medium comprising monosaccharides as only carbohydrate source, dGMM and LAB medium comprising Mucin, dGMM and LAB medium comprising Mucin as only carbohydrate source, dGMM and LAB medium comprising only 10% amino acids, and dGMM and LAB medium excluding aromatic amino acids can be combined to culture the bacterial species of the herein disclosed invention.

Preferred is the in-vitro model according to the present invention, further comprising the afore-described medium kit.

Yet another aspect of the present invention relates to a method for producing an in-vitro model of the human gut microbiome, comprising providing a fecal sample from a healthy human subject or a group of healthy human subjects, isolating and identifying bacterial strains from said sample, and combining said strains into a panel, until said panel has a cumulative enzymatic coverage of more than 85% of the gut microbiome of said healthy human and/or group of humans.

Another aspect of the present invention then relates to a method for determining the effect of at least one compound on the human gut microbiome, comprising the steps of
a) providing an in-vitro model of the human gut microbiome according to the present invention;
b) providing at least one compound to be tested;
c) culturing said in-vitro model in the presence of said compound in vitro;
d) determining the bacterial growth in said in-vitro model; and
e) determining the effect of said at least one compound on said human gut microbiome comprising comparing said growth to a control culture.

In a preferred embodiment, the present invention further relates to a method for determining the effect of at least one compound on the human gut microbiome, wherein said compound is a food ingredient, a food additive, a drink additive, a food supplement, a drink supplement, a dietary supplement, a food flavor, a flavor enhancer, a nutritional product, a bioactive ingredient, a medical food, a cosmetic product, an herbal product, a therapeutic compound, a pharmaceutical compound, a pharmaceutical additive, an antimicrobial and/or immune enhancer, an antioxidant, an antibiotic, an immunosuppressant, a natural product, a bioactive compound, a protein, an amino acid, a manufactured product, a processed product, a synthetic product, and/or a preservative.

The term "control culture", in the context of the present invention, shall refer to a culture of said in-vitro model, which is cultured in the absence of said compound in vitro.

Yet another aspect of the present invention relates to a method for determining a suitable dose of at least one compound for the effective treatment of a disorder in a human subject, comprising the steps of
a) providing an in-vitro model of the gut microbiome of said subject comprising a panel of bacterial species selected from *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella,* and *Bilophila*; optionally further comprising at least one bacterial species selected from *Escherichia, Akkermansia, Veillonella, Haemophilus, Desulfovibrio,* and *Butyrivibrio;*
a) providing a predetermined effective dose of said at least one compound for the effective treatment of said disorder in said subject;
b) culturing said in-vitro model in the presence of said predetermined effective dose of said compound, optionally wherein said culturing is performed using the medium kit according to claim 5;
c) determining a difference of said predetermined effective dose of said compound and said dose of said compound after said culturing from b) for a predetermined time, preferably for at least 6 hours, more preferably for at least 12 hours, most preferably for at least 24 hours, and
d) determining a suitable dose of said at least one compound for the effective treatment of said disorder in said human subject, wherein said difference is used to adjust the dose of said compound to reach said predetermined effective dose of said compound for the effective treatment of said disorder in said subject.

Further preferred is the afore-mentioned method for determining a suitable dose of at least one compound for the effective treatment of a disorder in a human subject, wherein said in-vitro model of the gut microbiome of said subject comprises species that are selected from *Bacteroides caccae, Bacteroides clarus, Bacteroides coprocola, Bacteroides dorei* or *Bacteroides vulgatus, Bacteroides eggerthii, Bacteroides fragilis, Bacteroides ovatus, Bacteroides thetaiotaomicron, Bacteroides xylanisolvens, Bacteroides stercoris, Bacteroides uniformis, Eubacterium eligens, Eubacterium rectale, Eubacterium siraeum, Alistipes putredinis, Alistipes shahii, Ruminococcus gnavus, Ruminococcus torques, Ruminoccocus bromii, Ruminococcus obeum, Roseburia hominis, Roseburia intestinalis, Parabacteroides distasonis, Parabacteroides merdae, Prevotella copri, Bifidobacterium adolescentis, Bifidobacterium longum, Coprococcus comes, Dorea formicigenerans, Blautia hansenii, Odoribacter splanchnicus, Clostridium bolteae, Clostridium leptum, Clostridium ramosum, Streptococcus parasanguinis, Streptococcus salivarius, Collinsella aerofaciens, Bilophila wadsworthia, Escherichia coli, Akkermansia muciniphila, Veillonella parvula, Haemophilus parainfluenzae, Desulfovibrio piger,* and *Butyrivibrio crossotus.*

An additional embodiment relates to the afore-mentioned method for determining a suitable dose of at least one compound for the effective treatment of a disorder in a human subject, wherein said compound is selected from the group consisting of psycholeptics, antivirals, cardiac therapeutics, antirheumatics, anti-diabetics, antibiotics, antihelmintics, analgesics, lipid modifying agents, antidiarrheals, psychoanaleptics, drugs for obstructive airway disease, drugs for acid related disorders, antidepressants, chemotherapeutic agents, antineoplastic drugs, bronchodilators, anti-inflammatory agents, antifungal agents, anti-infectious agents, and immunosuppressants, optionally wherein said disorder is selected from the group consisting of depression, a psychological disorder, a gastrointestinal disorder, a proliferative disorder, a metabolic disorder, a cardiovascular disorder, an immunological disorder, an infectious disease, a neurological disorder, a neurodegenerative disorder, a rheumatic disorder, arteriosclerosis, asthma, cancer, anaphylactic shock, anemia, angina, diarrhea, obesity, diabetes, a bacterial infection, a viral infection, a fungal infection, and a parasitic infection.

A further embodiment of the invention pertains to a method for diagnosing a disorder in a human subject, comprising a) providing an in-vitro model of the gut microbiome of said subject comprising a panel of bacterial species selected from *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella,* and *Bilophila*; optionally further comprising at least one bacterial species selected from *Escherichia, Akkermansia, Veillonella, Haemophilus, Desulfovibrio,* and *Butyrivibrio;* b) providing an in-vitro model of the gut microbiome according to the present invention;

c) culturing said in-vitro model from a) and culturing said in-vitro model from b), optionally wherein said culturing is performed using the medium kit according to claim 5;

d) determining the bacterial growths in said in-vitro models; and e) comparing said bacterial growths, wherein a difference in said bacterial growths is indicative for a disorder in said subject.

In the context of the present invention, the "in-vitro model of the gut microbiome according to the present invention" in step b) shall be preferably provided by a healthy human being or by multiple healthy human beings.

Yet another embodiment of the invention pertains to the afore described method for diagnosing a disorder in a human subject, wherein said in-vitro model comprises species that are selected from *Bacteroides caccae, Bacteroides clarus, Bacteroides coprocola, Bacteroides dorei or Bacteroides vulgatus, Bacteroides eggerthii, Bacteroides fragilis, Bacteroides ovatus, Bacteroides thetaiotaomicron, Bacteroides xylanisolvens, Bacteroides stercoris, Bacteroides uniformis, Eubacterium eligens, Eubacterium rectale, Eubacterium siraeum, Alistipes putredinis, Alistipes shahii, Ruminococcus gnavus, Ruminococcus torques, Ruminoccocus bromii, Ruminococcus obeum, Roseburia hominis, Roseburia intestinalis, Parabacteroides distasonis, Parabacteroides merdae, Prevotella copri, Bifidobacterium adolescentis, Bifidobacterium longum, Coprococcus comes, Dorea formicigenerans, Blautia hansenii, Odoribacter splanchnicus, Clostridium bolteae, Clostridium leptum, Clostridium ramosum, Streptococcus parasanguinis, Streptococcus salivarius, Collinsella aerofaciens, Bilophila wadsworthia,*

*Escherichia coli, Akkermansia muciniphila, Veillonella parvula, Haemophilus parainfluenzae, Desulfovibrio piger,* and *Butyrivibrio crossotus.*

In particular embodiments, said disorder to be diagnosed using the method according to the present invention is selected from a gastrointestinal disorder, a proliferative disease, a metabolic disorder, a cardiovascular disease, an immunological disease, and an infectious disease, preferably wherein said gastrointestinal disorder is selected from the group consisting of a gastrointestinal motility disorder, irritable bowel syndrome, constipation, a functional gastrointestinal disorder, gastroesophageal reflux disease, functional heartburn, dyspepsia, functional dyspepsia, nonulcer dyspepsia, gastroparesis, chronic intestinal pseudo-obstruction, colonic pseudo-obstruction, Crohn's disease, colitis, ulcerative colitis, inflammatory bowel disease, diverticulitis, gluten and/or lactose intolerance, stomach rumble, meteorism, and flatulence, and/or wherein said proliferative disease is selected from the group consisting of atherosclerosis, rheumatoid arthritis, and a cancer disease, such as, for example, colorectal cancer.

Another aspect of the invention is directed at the use of the in-vitro model of the human gut microbiome according to the present invention for determining the effect of at least one compound on the human gut microbiome, or for determining a suitable dose of at least one compound for the effective treatment of a disorder in a human subject, or for diagnosing a disorder in a human subject.

The afore described use of the in-vitro model of the human gut microbiome according to the present invention for determining the effect of at least one compound on the human gut microbiome relates to a compound selected from a food ingredient, a food additive, a drink additive, a food supplement, a drink supplement, a dietary supplement, a food flavor, a flavor enhancer, a nutritional product, a bioactive ingredient, a medical food, a cosmetic product, an herbal product, a therapeutic compound, a pharmaceutical compound, a pharmaceutical additive, an antimicrobial and/or immune enhancer, an antioxidant, an antibiotic, an immunosuppressant, a natural product, a bioactive compound, a protein, an amino acid, a manufactured product, a processed product, a synthetic product, and a preservative.

The disorder to be diagnosed using the in-vitro model of the human gut microbiome according to the present invention for determining the effect of at least one compound on the human gut microbiome is selected from a gastrointestinal disorder, a proliferative disease, a metabolic disorder, a cardiovascular disease, an immunological disease, and an infectious disease, preferably wherein said gastrointestinal disorder is selected from the group consisting of a gastrointestinal motility disorder, irritable bowel syndrome, constipation, a functional gastrointestinal disorder, gastroesophageal reflux disease, functional heartburn, dyspepsia, functional dyspepsia, nonulcer dyspepsia, gastroparesis, chronic intestinal pseudo-obstruction, colonic pseudo-obstruction, Crohn's disease, colitis, ulcerative colitis, inflammatory bowel disease, diverticulitis, gluten and/or lactose intolerance, stomach rumble, meteorism, and flatulence, and/or wherein said proliferative disease is selected from the group consisting of atherosclerosis, rheumatoid arthritis, and a cancer disease, such as, for example, colorectal cancer.

The present invention shall now be further described in the following examples with reference to the accompanying figures, nevertheless, without being limited thereto. For the purposes of the present invention, all references as cited herein shall be incorporated by reference in their entireties. In the Figures, FIGS. 1A-1B show selected species in the microbiome core. A species core of the human gut microbiome was estimated on 364 fecal metagenomes of pooled asymptomatic individuals from three continents (see inset for country codes). For inclusion in the core the inventors required a minimum prevalence of 10% and a relative abundance of 1% or more in at least one sample. (1A-1B) Boxplots show species colored by phylum (see box for color key); the inner box indicates the inter-quartile range, with the median as black vertical line; the outer bars extend to the 5th and $95^{th}$ percentiles.

FIG. 2 shows the species and media selection. a, Overview of selected bacterial strains. b, Species core of the human gut microbiome based on fecal metagenomes collected from 364 healthy individuals in four countries and their representation in this resource. Boxplots show selected core species grouped by genus (according to NCBI taxonomy) and colored by phylum (see box for color key); the inner box indicates the inter-quartile range, with the median as black vertical line; the outer bars extend to the 5th and 95th percentiles. Prevalence of individual genera across 364 metagenomics datasets is depicted in gray on the right within the same panel. Species diversity across 364 metagenomics datasets within each genus and their relative abundances are depicted in the middle panel with gray boxes indicating species represented in this screen. Cumulative fraction of relative abundance of represented species normalized by the total assignable metagenomics read abundance is shown in the colored right panel for each country separately (see inset). The last panel shows cumulative enzyme coverage relative to the core microbiome (see b). c, Overview of selected growth media. d, Comparison of nutrient group representation across all newly compounded media. Circle size correlates linearly with the quantity of the respective nutrient group. Changes in medium M4-11 compared to the basis medium M3 dGMM+LAB are additionally marked with a white dot.

FIG. 3 shows the growth profiles of 96 gut bacterial strains across 19 media. a, Heat map showing growth capacity of 96 gut bacterial strains across minimal (M1, M13-M16), defined (M2-M11) and rich media (GMM, BHI++, WCA, mGAM). Shown values are averages over up to 7 biological replicates (median 3) of maximum OD reached. b, Growth supporting capacity of 19 tested media; median as dotted gray vertical line. c, Media preference frequency for 96 tested bacteria; median as dotted gray vertical line. d, Clustering of tested gut bacteria by their growth profiles across 19 media (Methods). Colors mark different phyla. e, Distribution of growth capacity dissimilarity (MaxOD; Euclidian distance) within different taxonomic ranks.

FIG. 4 shows that the species growth patterns provide insights into microbiota ecology. a, Distribution of correlations between bacterial growth in tested media and their relative abundance within gut metagenomes of 364 healthy individuals compared to random background. b, Stratification of bacterial species according to preferential growth in defined media compared to rich media or no preference. c, Species with preference for defined media show significantly higher prevalence (p-value 0.00019). Only 8 out of 10 species that could be uniquely mapped in the metagenomics data are included.

FIG. 5 shows the novel metabolic characteristics of gut bacteria. a, Gut bacteria inhibited or boosted in absence of SOFA (M5), aromatic amino acids (M11) or when amount of amino acids was reduced to 10% (M10) compared to basis medium (M3). b, Overlap of species growing in presence of mucin as sole carbohydrate source (M9 hits), species with improved growth in presence of additional mucin (M8 hits) (>2-fold improvement compared to the basis medium M3), and species with 3 known mucin degradation enzymes (based on mapping to CAZy database). Strains benefiting in presence of mucin (M8 or M9) are shown in the heatmap; * marks strains previously known to degrade mucin.

Figure 8A:
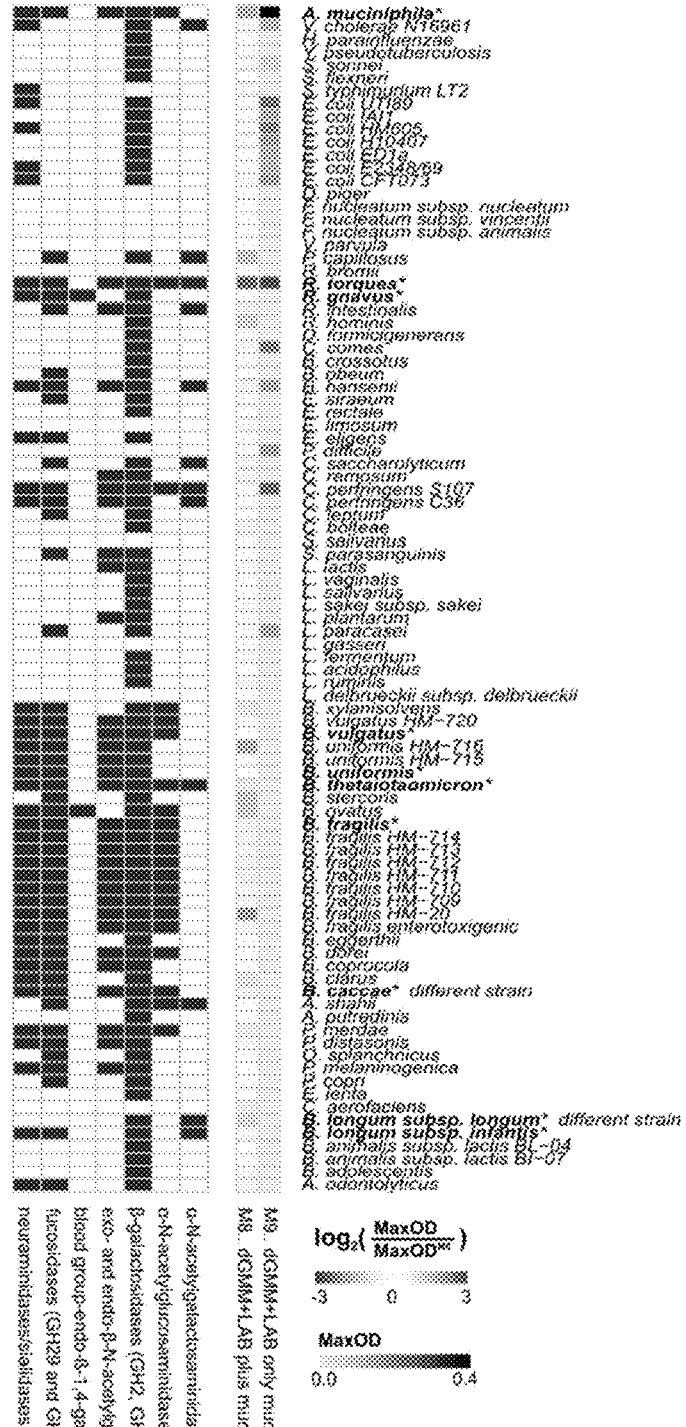
Figures 8B, 8C:
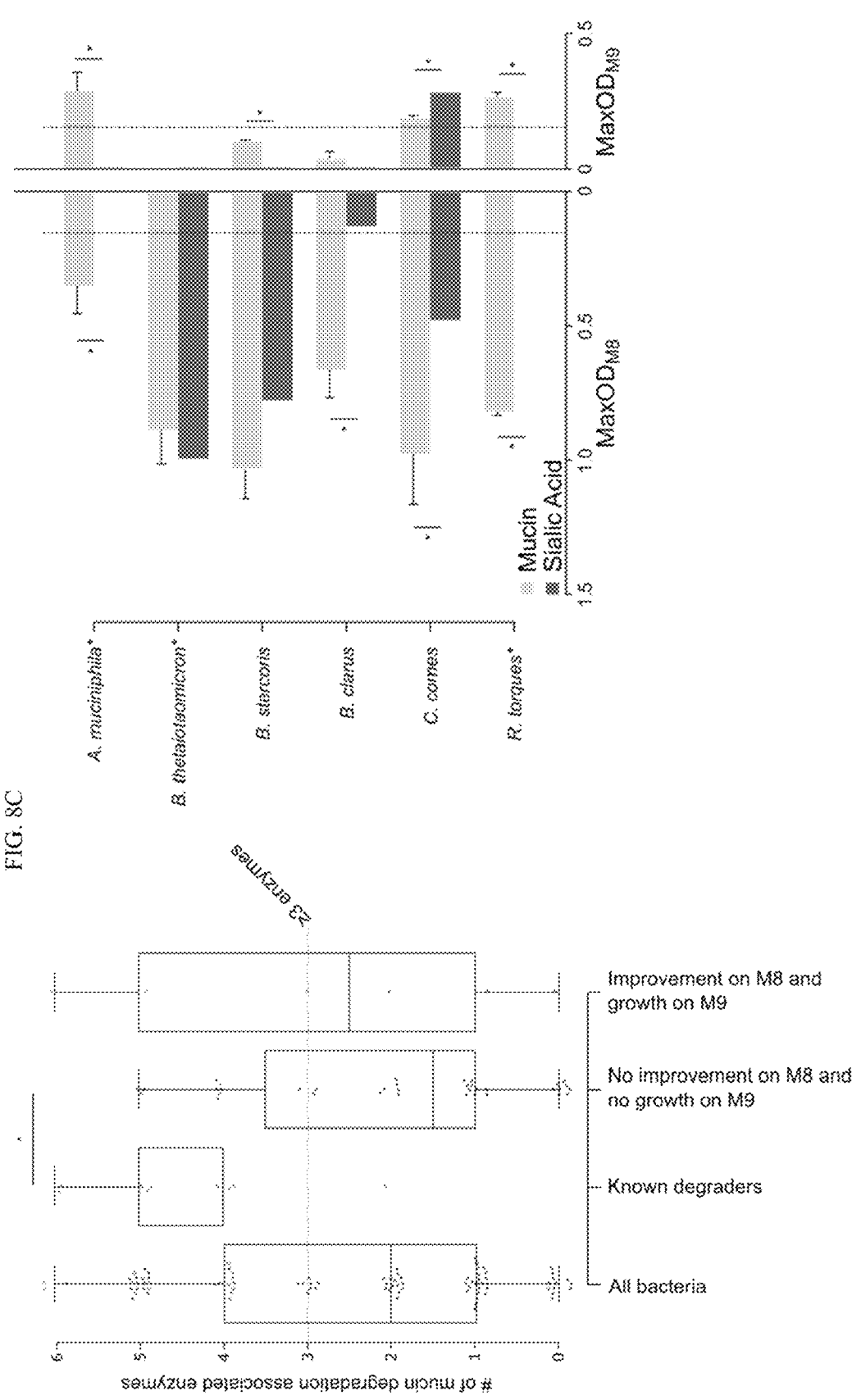

FIG. 8 shows growth of gut bacteria in presence of mucin. a, Presence of enzymes involved in mucin degradation, relative growth in medium containing additional mucin (M8/M3 fraction; $\log_2$ transformed), and growth in medium with mucin as sole carbohydrate source (M9). * marks strains known to degrade mucin. b, Mucin-degrading CAZy enzyme count for all bacteria in our screen, known degraders, species with no improvement on M8 and no growth on M9 vs. species with improvement on M8 and growth on M9. The box is showing the interquartile range, the median is displayed as black horizontal line; known degraders in red, species not described to utilize mucin in black. c, Growth of selected mucin-utilizing species in conventional mucin-containing M8 or M9 medium compared to M8 or M9 medium containing 0.075 mg/mL sialic acid instead of mucin. * marks strains known to degrade mucin.

Figure 9D:
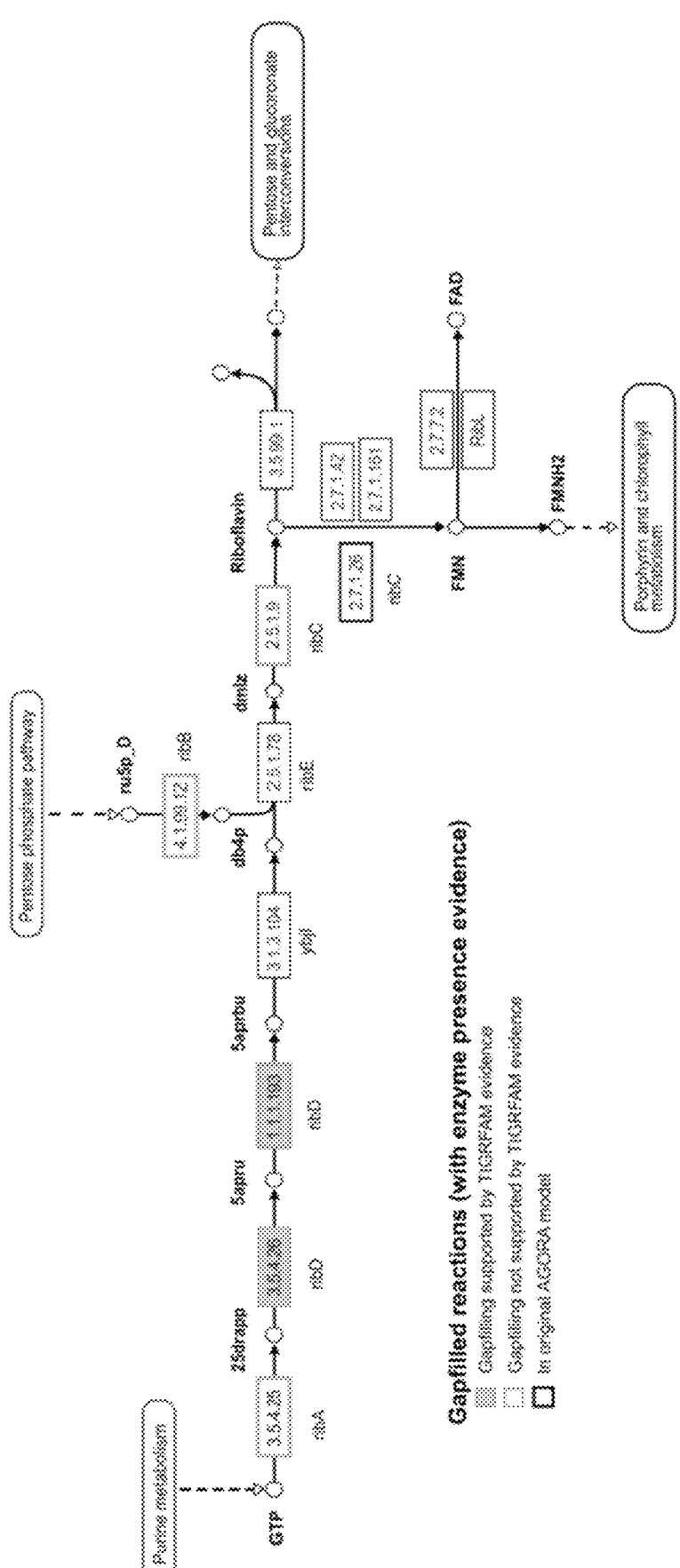

FIG. 9 shows Gap-filled reactions confirmed by TIGR-FAM. a, Improvement of AGORA models by gap-filling using data of growth in defined media. b, Gap-filled reactions stratified by subsystems; text annotation displays percentage of reactions confirmed with TIGRFAM. c, Overlap of gap-filled reactions with reactions found in TIGRFAM database; percentages inside the cell indicate proportion of reactions having evidence in TIGRFAM. d, Exemplified gap-filling of riboflavin pathway. Boxes with orange border indicate gap-filled reactions; filled boxes indicate evidence from TIGRFAM database.

Figure 10A:
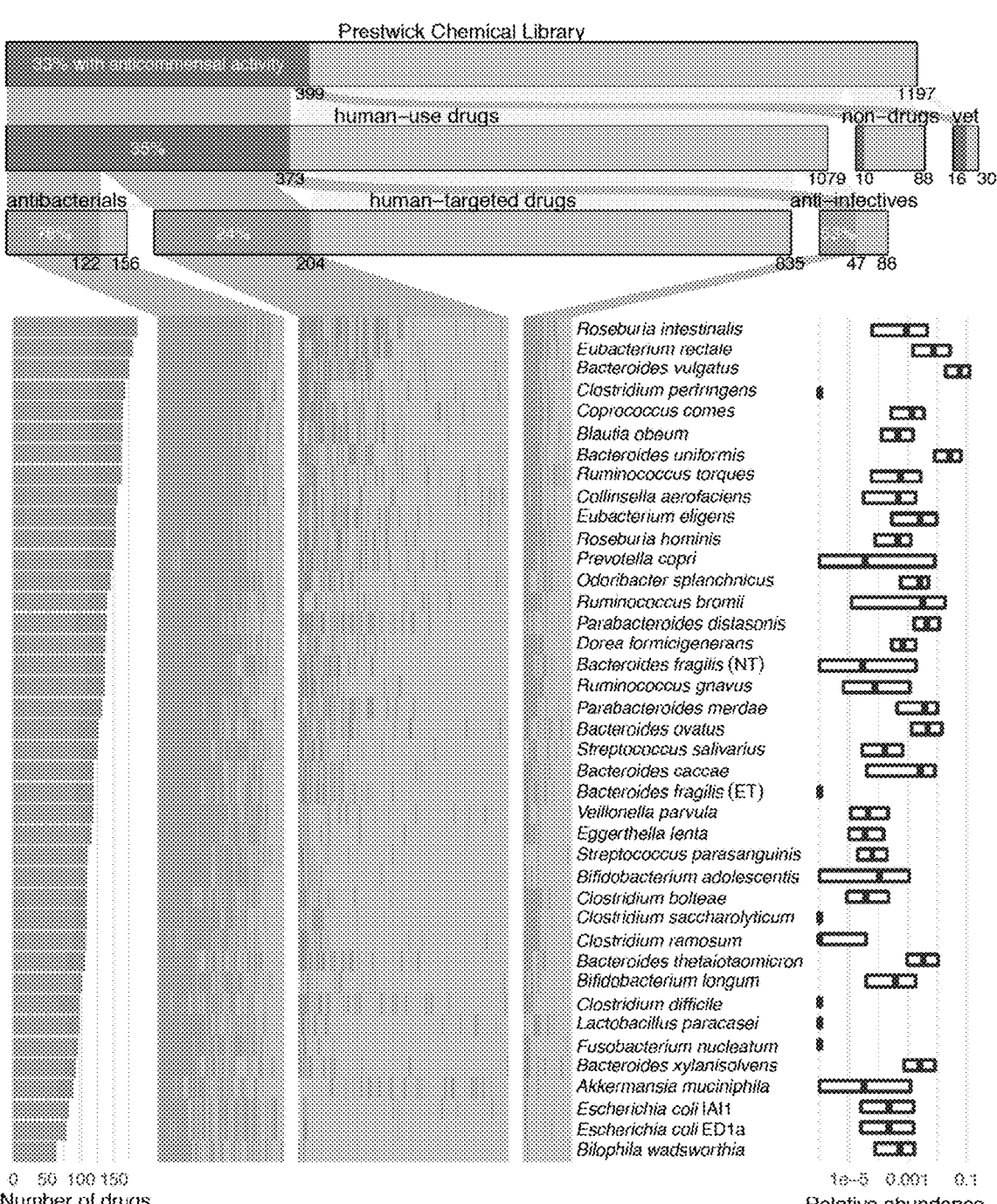

FIG. 10 shows the systematic profiling of the effects of marketed drugs on a representative panel of human gut microbial species. a, Broad impact of pharmaceuticals on the human gut microbiota. Compounds of the Prestwick Chemical Library are divided into drugs used in humans, exclusively in animals (veterinary) and compounds not primarily used for medical/veterinary purposes (non-drugs). Human-use drugs are further categorized according to their target organism: bacteria (antibacterial drugs—green), other pathogens (viruses, fungi and protozoan/metazoan parasites, summarized as other anti-infective drugs—blue) and human (human-targeted drugs—orange). When a drug significantly reduced the growth of a specific strain within a set of 40 representative gut microbiome strains, the strain-drug pair in the matrix is highlighted with a vertical colored bar. Bacterial strains are sorted on the y-axis according to their drug sensitivity, increasing from bottom to top. Relative abundances of each strain in four cohort studies of healthy individuals are displayed on the right. b, Fraction of drugs with anticommensal activity. The four main drug categories from a (same color code) are further subdivided according to human and veterinary use, and the anti-infectives further according to target or use. Grey scale within bars denotes inhibition spectrum, that is the number of affected strains per drug; each bar is subdivided in as many parts as drugs with anticommensal activity within that group. c, Correlation between species abundance in the human microbiome and species sensitivity to drugs. For each strain, the number of drugs from each of the three medically relevant categories impacting its growth is plotted against its median relative abundance in the human gut microbiome (colors as in a & b). Lines depict the best linear fit, rS the Spearman correlation and grey shade the 95% confidence interval of the linear fit. All drugs, and in particular human-targeted drugs, inhibit abundant species more.

Figures 11A, 11B, 11C:
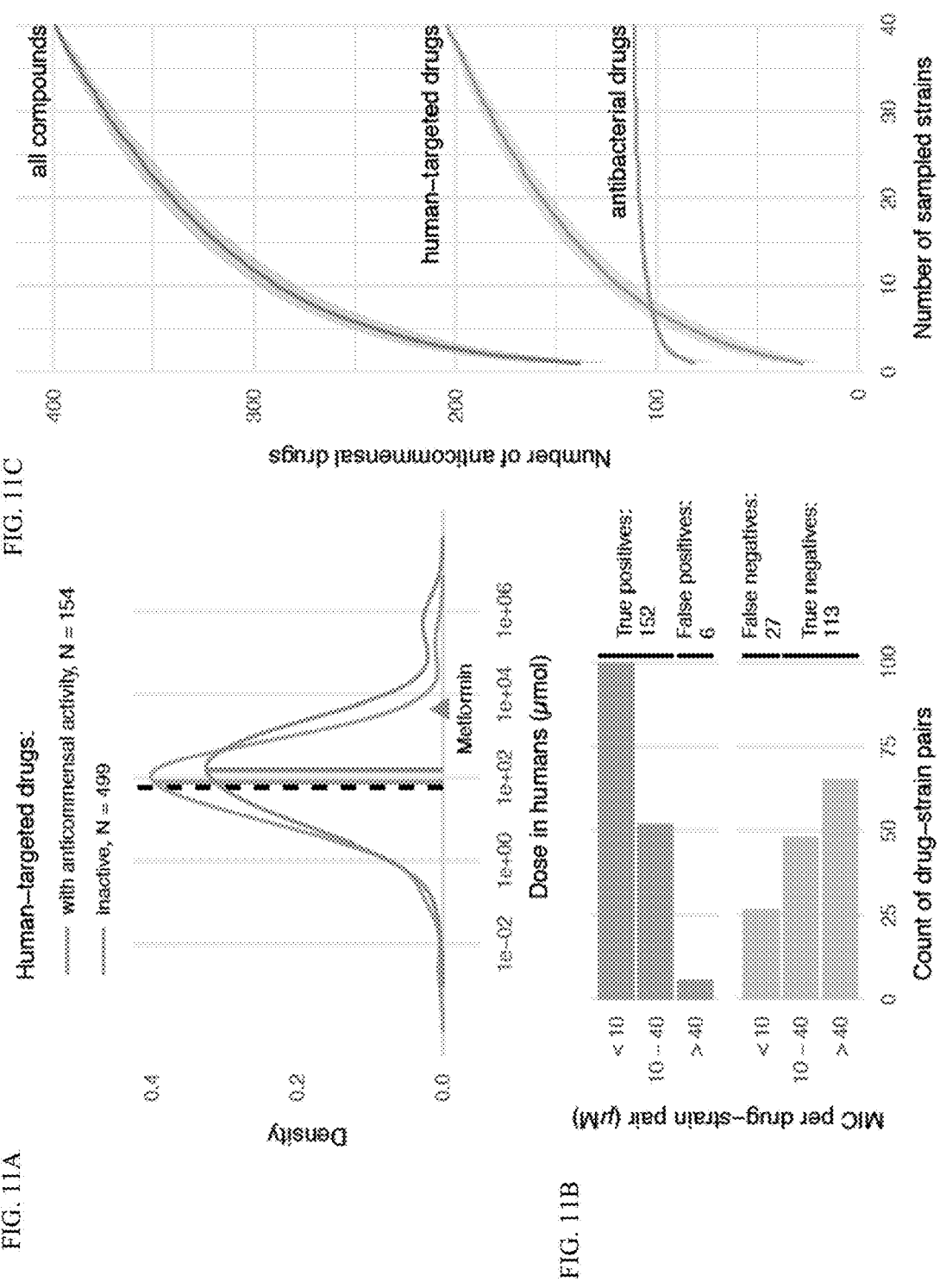

FIG. 11 shows the conservative estimate of human-targeted drugs with anticommensal activity. a, Recommended single drug doses for human-targeted drugs with (orange) and without (grey) anticommensal activity in our screen, converted to drug intestinal concentrations based on detailed measurements made for posaconazole. Doses were extracted from Drugs@FDA and Daily Defined Dose (DDD) of the ATC. For both active and inactive compounds, the median drug doses (orange and grey vertical lines) are slightly higher than the dose equivalent to the screen concentration (dashed black line). Non-hits in our screen are generally taken at higher doses (p=0.001, Wilcoxon rank sum test), implying that if the inventors screened at higher, more physiological concentrations, further drugs would have activity. Metformin, a drug known to be administered at much higher concentrations and to actually accumulate in the gut is shown as example (arrow for estimated intestinal concentration). Its suspected anticommensal activity is verified when testing higher concentrations than the 20 μM used in the screen. b, MIC determination for 22 selected drugs, purchased from independent vendors, in a subset of 15 strains validates quality of the screen: precision (96%) and recall (85%). The inventors considered MIC as the lowest concentration that reduces growth by >25% (Methods). Since MIC calculation is known to have a two-fold error margin and our hit-calling in screen and MIC validation are slightly different (Methods), the inventors considered an MIC of 10-40 μM as being in agreement with the screening result. Higher number of false negatives implies that likely more human-targeted drugs have anticommensal activity. c, Rarefaction analysis indicates that anticommensal activity would be discovered for more human-targeted drugs if the inventors screened additional strains to the 40 probed here. In contrast, all antibiotics with anticommensal activity in the Prestwick Chemical Library have likely been identified.

Figure 12A:
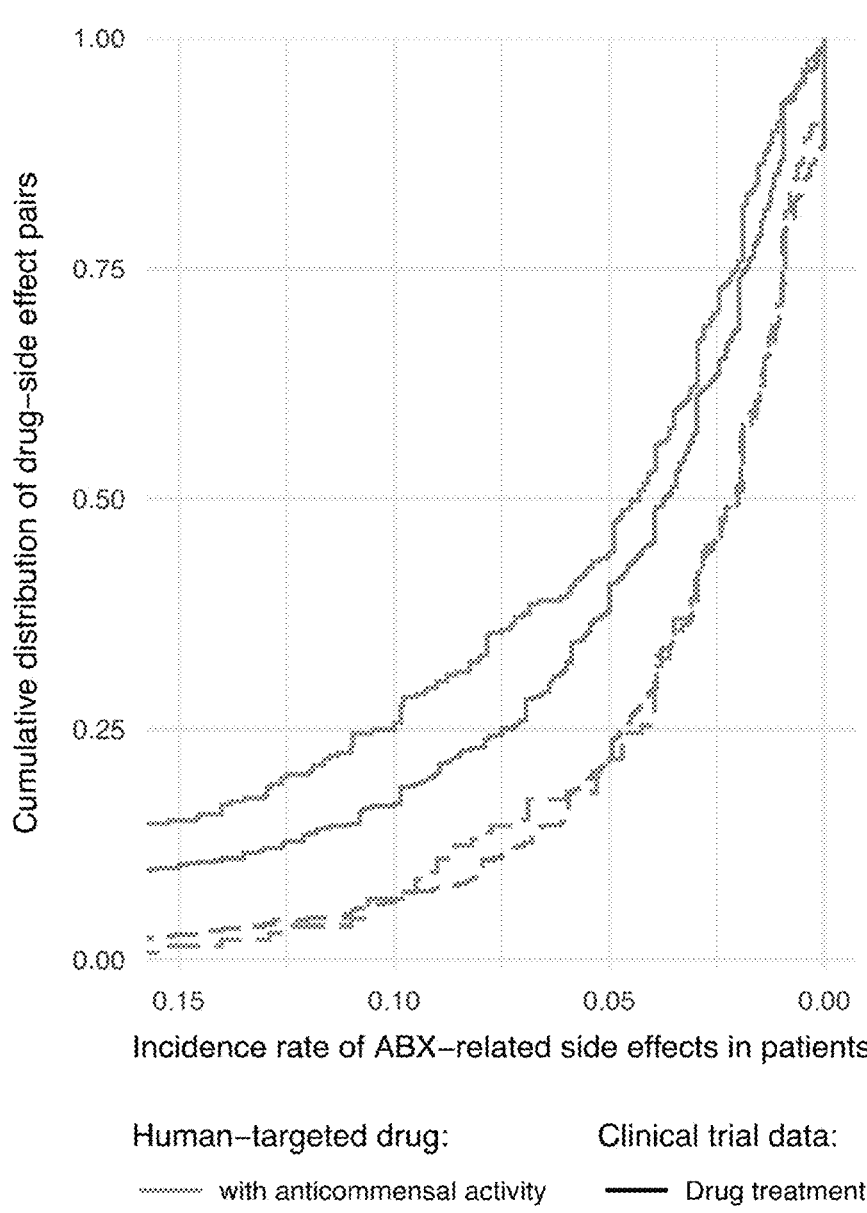

FIG. 12 shows side effect patterns confirm anticommensal activity of human-targeted drugs. a, Human-targeted drugs with anticommensal activity in our screen had a significantly higher incidence of antibiotic-related side effects (orange trace shows cumulative distribution) in clinical trials compared to drugs without activity (grey trace; p=0.002, Wilcoxon rank sum test). Thus, anticommensal activity captured by our screen manifests as microbiota-related side effects in humans. Dashed lines indicate the incidence of the same side effects upon placebo treatment, for which no significant difference could be observed. b, Recommended single drug doses of human-targeted drugs with no anticommensal activity in our screen plotted against enrichment in antibiotic-related side effects (n=338). The inventors selected 26 candidate and 16 control drugs for testing for anticommensal activity at higher concentrations, based on similarity to antibiotic-related side effects (vertical black line depicts prediction threshold) and aiming at drugs used at higher doses than concentration in our screen (horizontal dashed line). Purple and dark grey triangles indicate hits and non-hits from this validation effort, respectively. c, Although both candidate and control drugs inhibit bacterial growth at higher concentrations, candidate drugs have anticommensal activity at significantly lower doses than control drugs (p=2e-6, one-sided Wilcoxon rank sum test). This demonstrates that anticommensal activity can be predicted from side effects.

Figures 13A, 13B, 13C:
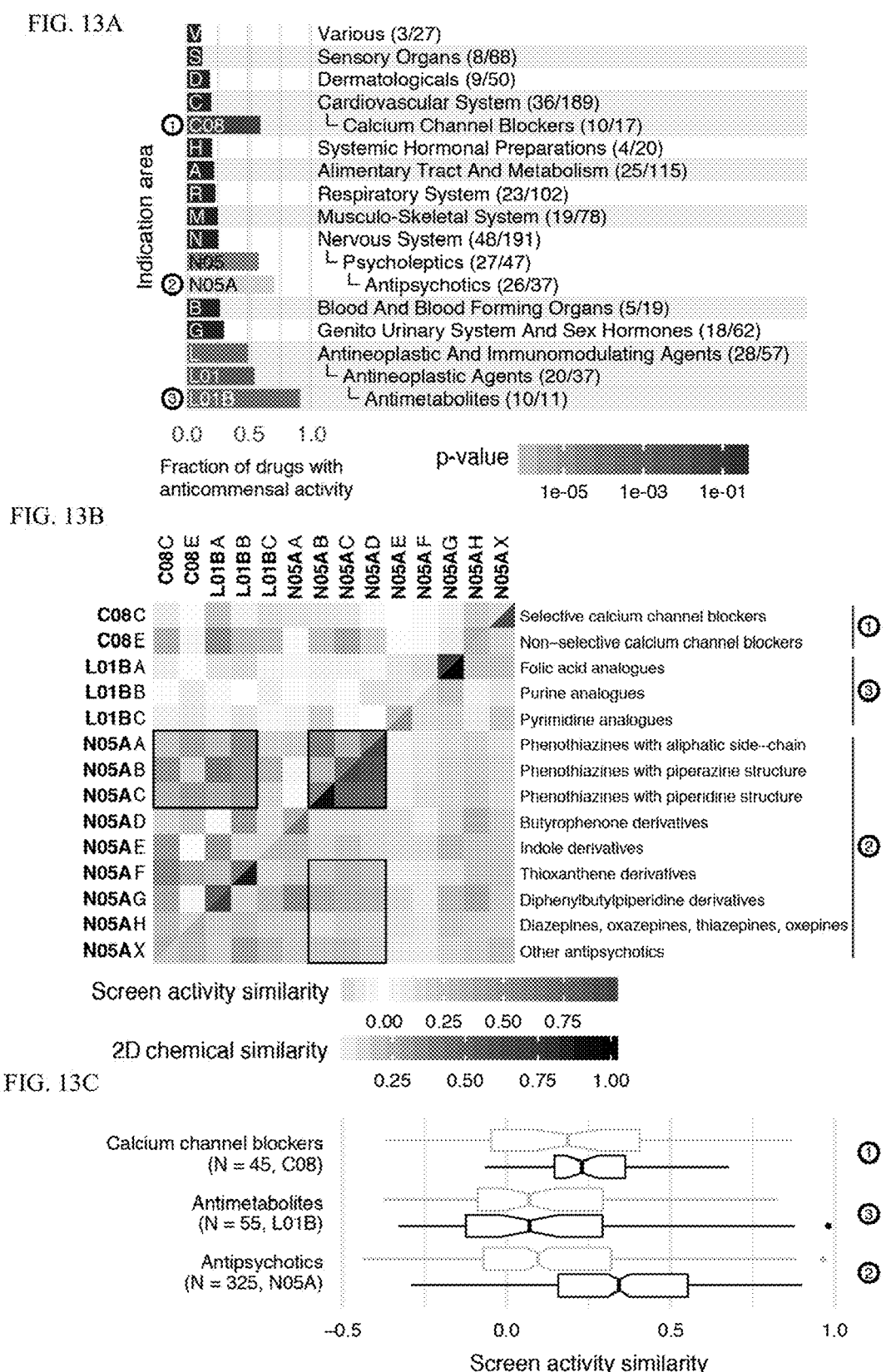

FIG. 13 shows that drug therapeutic class and chemical properties influence anticommensal activity. a, Fraction of drugs with anticommensal activity by indication area according to the ATC classification scheme (bars). All first-level indication areas and significantly enriched lower levels are shown. Significance (p-value, Fischer's exact test) is indicated by the bar color and controlled for multiple hypothesis testing (Benjamini-Hochberg) independently at each hierarchy level of the ATC. b, Heat map of anticommensal activity and chemical similarities of human-targeted drugs within the three significantly ATC indication levels from a. Colors represent the median of drug pairwise Spearman correlations within and between subgroups depicted, calculated from the growth profiles of the 40 strains in each drug (p-values) or their Tanimoto scores. Examples of structurally similar (phenothiazines; N05AA-AC) and diverse (N05AF-AX) antipsychotics that all elicit similar responses in our screen are marked. c, Antipsychotics exhibit higher similarity in gut microbes they target than that expected based on their structural similarity (p-value=2e-19; other classes depicted show no significance difference).

Figure 14A:
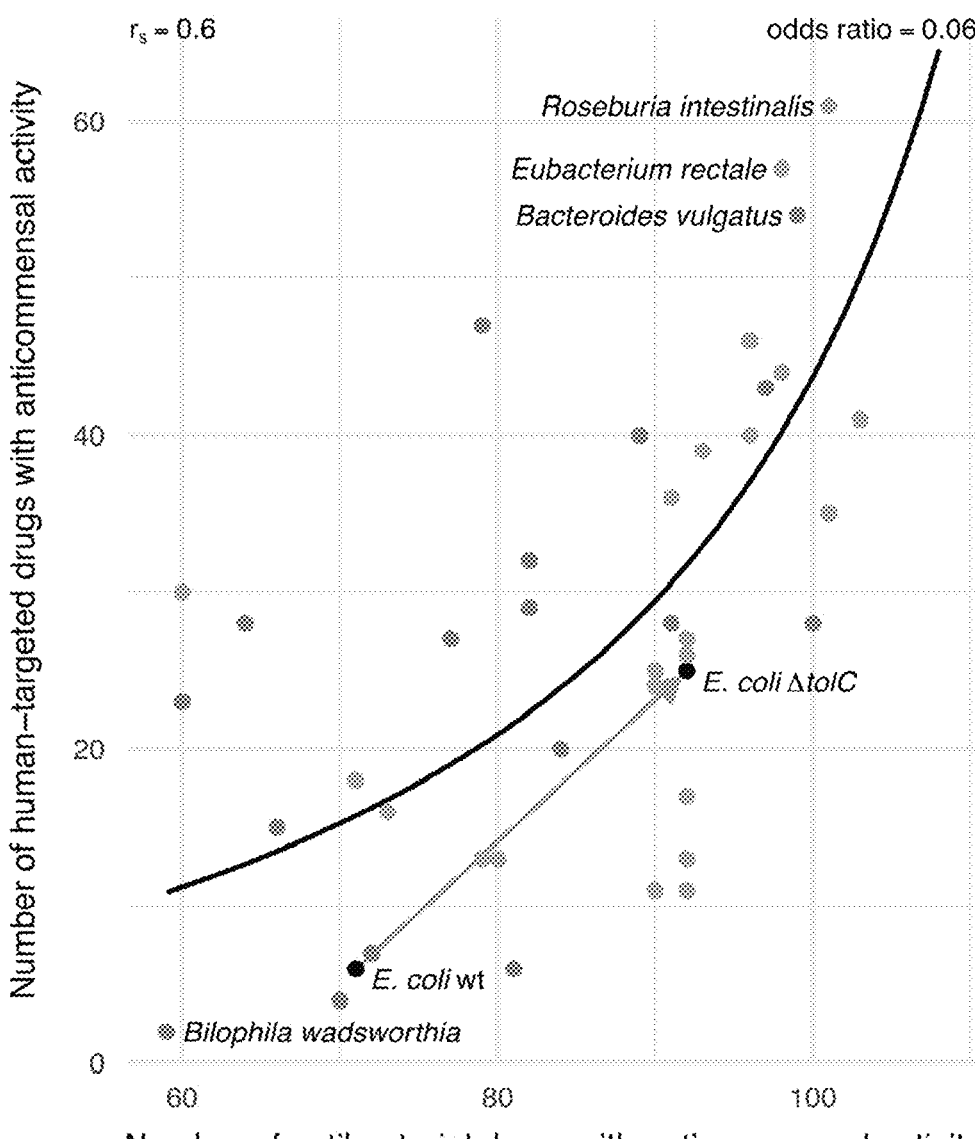
Figure 14B:
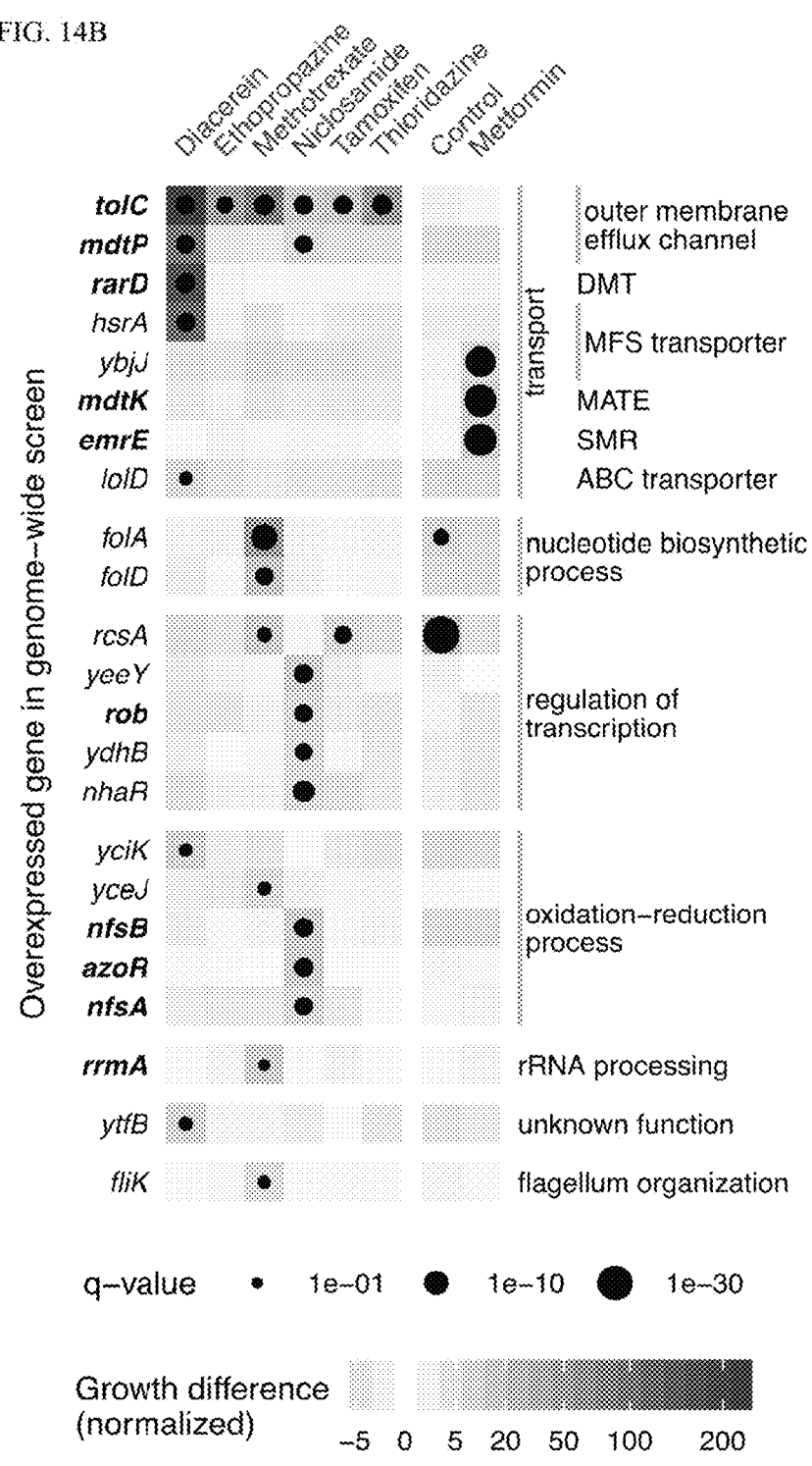

FIG. 14 shows that antibiotic resistance mechanisms protect against human-targeted drugs. a, For each of the 40 strains tested, colored here according to Gram-staining, number of human-targeted drugs that inhibit its growth are plotted against the number of antibiotics the strain is sensitive to. Susceptibility to antibacterials and human-targeted drugs correlates across species (Spearman correlation, rS=0.6 and a line depicting the nonlinear least-squares estimate of the odds ratio, OR=0.06), suggesting common resistance mechanisms against both types of drugs. Black dots denote the lab *E. coli* strain, BW25113 (behaving similar with the other 2 commensal *E. coli* strains, which are part of the screen), and its ΔtoIC derivative. Knocking out this major antibiotic efflux pump, toIC, makes *E. coli* equally more sensitive to both antibacterials and human-targeted drugs. b, Chemical genomics of an *E. coli* genome-wide overexpression library in 6 human-targeted drugs and the antiparasitic niclosamide; all screens except for metformin were performed in ΔtoIC background to sensitize *E. coli* to these drugs. Genes that when overexpressed, improve significantly the growth of *E. coli* to at least one of the drugs are shown here. Genes previously associated with antibiotic resistance are shown in bold. Among them, genes encoding for transporters from different families are illustrated—abbreviations for families are as following: DMT (drug metabolite transporter), MFS (major facilitator superfamily), MATE (multidrug and toxin extrusion), SMR (small multidrug resistance) and ABC (ATP-binding cassette). Growth is measured by colony size, color depicts the normalized size difference from the median growth of all strains in the drug, and dot size the significance of effect (FDR-corrected p values). Control denotes the growth of the library without drug.

FIG. 15 shows: a, Drug selection started with approximately 1000 annotated drugs from the SIDER side effect database, which were filtered for their gut related side effects. Drug selection was enriched from another database for known or suspected interactions with the gut microbiome, before filtered for oral administration and manually curated for overall interest. Final selection was filtered for availability from vendors and establishment of UPLC methods. Pie chart classifying selected compounds by therapeutic area. b, Cumulative abundance from a metagenomic dataset of healthy individuals. * indicates strains from the same SpecI cluster. Pie chart classifying selected bacterial strains by Genus. c, Experimental setup of bacteria-drug interaction. After 48 h anaerobic cultivation with OD growth detection and subsequent ACN:MethOH extraction of supernatant, drug concentration was measured with UV-UPLC detection. Interactions were screened in technical triplicates and biological duplicates. d, Density distribution of drug depletion in comparison to bacteria-free control for each drug respectively. Ticks in the rug below indicate different biological replicates. Background colors indicate positive (red) and negative (blue) drug controls for depletion. Dashed lines in each plot mark a 30% threshold for bacteria-drug interaction hits. e, Drug depleting bacteria per drug (minimum of 30% depletion in both biological replicates). f, Drug depletions per bacterial strain (minimum of 30% depletion in both biological replicates).

FIG. 16 shows: a, Experimental setup of depletion-mode assay for hits from bacteria-interaction screen with 30% cutoff in both biological replicates. Bacteria were grown 48 h anaerobically, split in half, subsequently either the supernatant or the total fraction was ACN:MethOH extracted and the concentration was measured with UV-UPLC detection. Samples were tested in triplicates. b, Correlation between bacteria-drug interaction: corrected AUC of drug peaks from supernatant extractions from interaction screen with supernatant extractions from depletion-mode assay. Lines indicate standard error of the mean. Dotted line indicates pearson correlation of 0.4 c, Scatter plot of depletion-mode assay: Supernatant extractions vs. Total extractions. Dashes line indicates perfect correlation. Interactions above dashed line suggest higher bioaccumulation then biotransformation. d, Barplot comparing strength of accumulated bacterial interactions, respectively from supernatant or total extractions for each tested drug. e, Barplot showing cumulative abundance of bacteria depleting drugs (minimum 10% depletion, biodegradation: ≥70% of bioaccumulated drug is transformed, otherwise bioaccumulation) for each tested drug. * indicates strains from the same SpecI cluster. f, Bacteria-drug interactions found in the depletion-mode assay. Drug bioaccumulation: at least 20% depletion; drug biodegradation: ≥70% of bioaccumulated drug is degraded. Growth effect as found in the interaction screen: student's t test, alpha<0.05, hit in both biological replicates.

FIGS. 17A-17G show untargeted metabolomics: A, Log10 of significant (Student's t-test, FDR<0.05) fold changes between samples treated with duloxetine and the respective drug or bacteria control. Each dot represents an m/z feature, which is significantly differentially expressed in comparison to both controls. Features have been filtered for variation before testing: CV>0.2 between conditions, CV<0.2 within one condition. Uniqueness of features has been checked for mass features with a fold change above 10 in comparison to both controls. B, Alkynated duloxetine. C, Fold change of proteins detected in duloxetine pull down of *C. saccharolyticum* lysate. Presented values are reached after imputing for not-missing-at-random from controls and correcting for an overall higher intensity in test samples in comparison to control samples. Four replicates each were tested. Color refers to: not significantly enriched proteins (grey); significantly (FDR, alpha<0.1, log 2(Fc)>2) enriched proteins (red). D and E, KEGG maps affected metabolic processes. F, Species abundance after transfer and 48 h growth in bacterial community with and without duloxetine.

Mean of relative abundance from triplicates after 16 s DNA sequencing. G, Dilution series of duloxetine in 1% DMSO. Underlying growth curves taken for 24 h in GMM in triplicates. OD at half maximum OD time point of control used as effect response. Dashed line indicates 50% of half-maximum OD, to estimate corresponding inhibitory concentration (IC50).

In the context of the present invention, the term "microbiota" refers, collectively, to the entirety of microbes found in association with a higher organism, such as a human. Organisms belonging to a human's microbiota may generally be categorized as bacteria, archaea, yeasts, and single-celled eukaryotes, as wells as viruses and various parasites.

The term "microbiome" refers, collectively, to the entirety of microbes, their genetic elements (genomes), and environmental interactions, found in association with a higher organism, such as a human.

The microbiome comprises many probiotic bacterial strains. The term "probiotic" as used herein means living microorganisms, which, when administered in adequate amounts, confer a health benefit on the host. Probiotics may be available in foods and dietary supplements (for example, but not limited to capsules, tablets, and powders). Examples of foods containing probiotics are yogurt, fermented and unfermented milk, miso, tempeh, and some juices and soy beverages.

Some bacterial strains of the microbiome are known to have a probiotic function, such as *Lactobacillus, Bifidobacterium, Enterococcus, Streptococcus, Pediococcus, Leuconostoc, Bacillus, Escherichia,* and *Lactococcus.*

The term "subject", as used herein, preferably refers to a mammal, such as a mouse, rat, guinea pig, rabbit, cat, dog, monkey, or preferably a human. The subject of the invention may be at danger of suffering from a disease, such as a bacterial infection, a viral infection, a fungal infection, and a parasitic infection. A more detailed description of medical indications relevant in the context of the invention is provided herein elsewhere.

Two types of bacteria can be differentiated based on structural differences in their cell walls, Gram-positive and Gram-negative bacteria. In the method developed by Hans Christian Gram, some bacteria retain a crystal violet dye due to a thick layer of peptidoglycan in their cell walls. These bacteria are referred to as Gram-positive bacteria. In contrast, Gram-negative bacteria do not retain the crystal violet dye and are colored red or pink in the test developed by Gram.

*Acinetobacter* is a genus of aerobic, Gram-negative bacteria belonging to the wider class of *Gammaproteobacteria*. *Acinetobacter* species are not motile, oxidase-negative, and occur in pairs. *Acinetobacter* species are a key source of infection in debilitated patients in the hospital, in particular the species *Acinetobacter baumannii*.

*Actinomyces* is a genus of Gram-positive actinobacteri, which are facultatively anaerobic (except *A. meyeri*, a strict anaerobe). Individual bacteria are rod-shaped, while *Actinomyces* colonies form fungus-like branched networks of hyphae. *Actinomyces* species are normally present in the gums and are the most common cause of infection in dental procedures and oral abscesses. Many *Actinomyces* species are opportunistic pathogens of humans and other mammals, particularly in the oral cavity. In rare cases, these bacteria can cause actinomycosis, a disease characterized by the formation of abscesses in the mouth, lungs, or the gastro-intestinal tract. Actinomycosis is most frequently caused by *Actinomyces israelii*.

*Bacteroides* is a genus of Gram-negative, obligate anaerobic bacteria. *Bacteroide* species are non-endospore-forming bacilli, and may be either motile or non-motile, depending on the species. Some species, such as *B. fragilis*, are opportunistic human pathogens. *B. fragilis* is the main cause of infections of the peritoneal cavity, gastrointestinal surgery, and appendicitis via abscess formation. Although *Bacteroide* species are anaerobic, they are transiently aerotolerant and thus can survive in areas such as the abdominal cavity.

*Neisseria* are Gram-negative bacteria, belonging to proteobacteria. They colonize the mucosal surfaces of many animals. The main pathogenic *Neisseria* species are *N. meningitidis* and *N. gonorrhoeae*.

*Chlamydia* is a genus of pathogenic bacteria that are obligate intracellular parasites. *Chlamydia* infections are the most common bacterial sexually transmitted diseases in humans and are the leading cause of infectious blindness worldwide.

*Vibrio* is a genus of Gram-negative bacteria, possessing a curved-rod shape. Multiple *Vibrio* species can cause foodborne infections, usually associated with eating undercooked seafood.

*Treponema* is a genus of spiral-shaped bacteria. The major pathogenic *Treponema* species is *Treponema pallidum*, causing diseases such as syphilis, bejel, and yaws.

*Mycobacterium* is a genus of *Actinobacteria*, given its own family, the Mycobacteriaceae. They are aerobic and non-motile bacteria (except for the species *Mycobacterium marinum*, which has been shown to be motile within macrophages). Mycobacteria have an outer membrane, possess capsules, and most do not form endospores.

*Bordetella* is a genus of small (0.2-0.7 μm), Gram-negative coccobacilli of the phylum Proteobacteria.

*Alistipes* is a genus in the phylum Bacteroidetes.

*Borrelia* is a genus of bacteria of the spirochete phylum. *Borrelia* cause borreliosis, a zoonotic, vector-borne disease transmitted primarily by ticks and lice.

*Brucella* is a genus of Gram-negative bacteria. They are small, non-encapsulated, non-motile and facultatively intracellular coccobacilli.

*Diplococci* are round bacteria (forming a coccus) that typically occur in the form of two joined cells. *Diplococci* can be Gram-negative and Gram-positive.

*Leptospira* is a genus of *spirochaete* bacteria, including a small number of pathogenic and saprophytic species.

*Alistipes* is a genus in the phylum Bacteroidetes.

*Desulfovibrio* is a genus of Gram-negative sulfate-reducing bacteria. *Desulfovibrio* species are commonly found in aquatic environments with high levels of organic material, as well as in water-logged soils. They are major community members of extreme oligotrophic habitats such as deep granitic fractured rock aquifers.

*Listeria* are gram-positive, rod-shaped, and facultatively anaerobic bacteria, which do not produce endospores.

*Pasteurella* is a genus of Gram-negative, facultatively anaerobic bacteria. *Pasteurella* are non-motile and pleomorphic, and often exhibit bipolar staining.

*Rickettsia* is a genus of non-motile, Gram-negative, non-spore-forming, highly pleomorphic bacteria that can be present as cocci (0.1 μm in diameter), rods (1-4 μm long), or thread-like forms (10 μm long).

*Shigella* is a genus of Gram-negative, facultative anaerobic, non-spore-forming, non-motile, rod-shaped bacteria genetically closely related to *E. coli*.

*Parabacteroides* is a Gram-negative, anaerobic, non-spore-forming genus from the family of Porphyromonadaceae.

The genus *Odoribacter* derives its name from its rod shape and foul odor it produces in the mouth of dogs. Bacteria within this genus are atypical opportunistic pathogens, anaerobic, Gram-negative, non-spore-forming, and non-motile.

*Faecalibacterium* is a genus of bacteria. Its sole known species, *Faecalibacterium prausnitzii* is one of the most abundant and important commensal bacterium of the human gut microbiota.

*Collinsella* is a genus of *Actinobacteria*, belonging in the family of Coriobacteriaceae.

*Eggerthella* is a bacterial genus of *Actinobacteria*, in the family Coriobacteriaceae. Members of this genus are anaerobic, non-sporulating, non-motile, Gram-positive bacilli that grow singly, as pairs, or in short chains.

*Roseburia* is a genus of butyrate-producing, Gram-positive anaerobic bacteria that inhabit the human colon. They are members of the phylum firmicutes.

*Coliform* bacteria are defined as rod-shaped Gram-negative non-spore forming bacteria, which can ferment lactose with the production of acid and gas when incubated at 35-37° C.

*Bacillus* is a genus of gram-positive, rod-shaped bacteria and a member of the phylum Firmicutes. *Bacillus* species can be obligate aerobes, or facultative anaerobes.

*Desulfovibrio* is a genus of Gram-negative sulfate-reducing bacteria. *Desulfovibrio* species are commonly found in aquatic environments with high levels of organic material, as well as in water-logged soils. They are major community members of extreme oligotrophic habitats such as deep granitic fractured rock aquifers.

*Butyrivibrio* is a genus of bacteria in the class of Clostridia. Bacteria of this genus are common in the gastrointestinal systems of many animals.

*Akkermansia* is a genus in the phylum Verrucomicrobia. *Akkermansia* are oval-shaped, non-motile and Gram-negative bacteria, which are strictly anaerobic and chemo-organotrophic.

*Bilophila* are Gram-negative anaerobic rod-forming bacteria. These bacteria carry out fermentation within the gut using taurine as the final electron acceptor. They are urease-positive, bile resistant, catalase-positive, and are largely found in patients that have appendicitis.

*Blautia obeum* is a species of Gram-positive bacteria found in the gut. *B. obeum* is an anaerobe.

*Coprococcus* is a genus of anaerobic cocci, which are part of the human faecal flora.

*Dorea* is a genus of Clostridiaceae.

*Eubacterium* is a genus of Gram-positive bacteria in the family of Eubacteriaceae. These bacteria are characterized by a rigid cell wall.

*Lactobacillus* is a genus of Gram-positive, facultative anaerobic or microaerophilic, rod-shaped, non-spore-forming bacteria. Many *Lactobacilli* are known to be very effective probiotic bacterial species. *Lactobacillus acidophilus* is the most well-known probiotic and one of the most important for the health of the small intestine. Besides the lining of the intestine, *Lactobacillus acidophilus* can also take up residence in the vagina, cervix or urethra. *Acidophilus* inhibits pathogens, and produces natural antibiotics such as lactocidin and acidophilin, which enhance immunity. *Lactobacillus acidophilus* has anti-microbial effects against *Staphylococcus aureus, Salmonella, E. coli* and *Candida albicans*.

*Lactobacillus brevis* is a lactic acid producing probiotic that is helpful in synthesizing Vitamins D and K.

*Lactobacillus bulgaricus*, used in yogurt fermentation, plays a protective role by producing lactic acid, which creates a friendly environment for other species.

*Lactobacillus plantarum* makes lactolin, another natural antibiotic. *Lactobacillus plantarum* can also synthesize L-lysine, an anti-viral amino acid. This organism eliminates nitrate, promoting nitric oxide levels and decreases pathogens.

*Lactobacillus rhamnosus* has a high tolerance to bile salts, surviving in less favorable environments. This species has shown to be beneficial to the elderly and infants alike. *Lactobacillus rhamnosus* lowers the symptoms of lactose intolerance, protects the small intestine, and produces lactic acid in the large intestine. Other strains of *Lactobacilli* include *Lactobacillus fermentum, Lactobacillus caucasicus, Lactobacillus helveticus, Lactobacillus lactis, Lactobacillus reuteri* and *Lactobacillus casei.*

*Ruminococcus* is a genus of bacteria in the class of Clostridia. They are anaerobic, Gram-positive gut microbes. *Ruminococci* are found in significant numbers in the intestines of humans.

*Veillonella* are Gram-negative anaerobic cocci. These bacteria are well known for their lactate fermenting abilities. They are common bacteria in the intestines and oral mucosa of mammals.

*Francisella tularensis* is a pathogenic species of Gram-negative, rod-shaped coccobacillus, an aerobe bacterium. It is non-spore forming, non-motile and the causative agent of tularemia, the pneumonic form of which is often lethal without treatment.

The genus *Legionella* is a pathogenic group of Gram-negative bacteria. The species *L. pneumophila* causes legionellosis including a pneumonia-type illness called Legionnaires' disease and a mild flu-like illness called Pontiac fever.

Actinobacillus is a genus of Gram-negative, non-motile and non-spore-forming, oval-to-rod-shaped bacteria occurring as parasites or pathogens in mammals, birds, and reptiles. They are members of the Pasteurellaceae family.

*Coxiella* refers to a genus of Gram-negative bacteria in the family Coxiellaceae.

*Kingella kingae* is a species of Gram-negative aerobic coccobacilli. They cause infections such as septic arthritis, osteomyelitis, spondylodiscitis, bacteraemia, and endocarditis, and less frequently lower respiratory tract infections and meningitis.

*Haemophilus* is a genus of Gram-negative, pleomorphic, coccobacilli bacteria belonging to the Pasteurellaceae family.

*Bifidobacterium* is a genus of Gram-positive, non-motile, often branched anaerobic bacteria. They are ubiquitous, endosymbiotic inhabitants of the gastrointestinal tract, vagina and mouth of mammals, including humans. *Bifidobacteria* are one of the major genera of bacteria that make up the colon flora in mammals. Some *Bifidobacteria* are also known to be probiotic. Of these, *Bifidobacterium bifidum* is the most recognized of this category. Living within the mucus lining of the large intestine and/or vaginal tract, *Bifidobacterium bifidum* prevents pathogenic bacteria and yeast from invading. *Bifidobacterium bifidum* creates favorable changes in pH levels by producing lactic and acetic acids. In addition, this species increases absorption of iron, calcium, magnesium and zinc. *Bifidobacterium infantis* simulates the production of cytokines that affect the immune system, and can kill off pathogens such as *Clostrida, Sal-*

*monella* and *Shigella. Bifidobacterium longum* colonizes the large intestine and prevents unfriendly bacteria and yeast from taking residence. Accordingly, this can result in a reduction of the frequency of gastrointestinal problems, such as diarrhea, and nausea during antibiotic use.

*Campylobacter* is a genus of microaerophilic Gram-negative bacteria. *Campylobacter* are a significant cause of food poisoning due to handling of raw meat or undercooking meat. *Campylobacter* are motile, with either unipolar or bipolar flagella. The organisms have a characteristic spiral/corkscrew appearance and are oxidase-positive. *Campylobacter jejuni* is one of the main causes of bacterial foodborne disease in many developed countries. At least a dozen species of *Campylobacter* have been implicated in human diseases.

*Clostridium* is a genus of Gram-positive bacteria, which are obligate anaerobes capable of producing endospores. Individual bacterial cells are rod-shaped. The five main species responsible for diseases in humans are *C. botulinum* (it produces botulinum toxin in food/wound and can cause botulism), *C. difficile* (it can flourish when other bacteria in the gut are killed during antibiotic therapy, leading to pseudomembranous colitis, a cause of antibiotic-associated diarrhea), *C. perfringens* (also known as *C. welchii*, it causes a wide range of symptoms, from food poisoning to gas gangrene, and is also responsible for enterotoxemia), *C. tetani* (it is the causative organism of tetanus) and *C. sordellii* (it may cause a fatal infection in exceptionally rare cases after medical abortions).

*Corynebacterium* is a genus of Gram-positive, rod-shaped bacteria, widely distributed in nature and mostly innocuous.

*Enterococcus* is a genus of Gram-positive, lactic acid bacteria of the phylum Firmicutes. Important clinical infections caused by *Enterococcus* include urinary tract infections, bacteremia, bacterial endocarditis, diverticulitis, and meningitis. Of note, *Enterococcus faecium* has shown to have a probiotic effect. This organism can be advantagous for diarrhea, particularly by shortening the duration of symptoms. It has further been shown to kill pathogenic microbes, such as rotavirus.

*Fusobacterium* is a genus of anaerobic, Gram-negative bacteria, wherein individual cells are rod-shaped bacilli with pointed ends. *F. nucleatum* has been lately strongly associated with colorectal cancer, and there is now evidence that antibiotic treatment in animal models for colorectal cancer reduces its load and delays disease.

*Helicobacter* is a genus of Gram-negative bacteria having a characteristic helix shape. *Helicobacter pylori* is a causative agent of gastric cancer.

*Mobiluncus* is a genus of gram-positive, anaerobic, rod-shaped bacteria. They are found in the human vagina, particularly in association with *Gardnerella vaginalis* in cases of bacterial vaginosis.

*Prevotella* is a genus of Gram-negative bacteria. *Prevotella* bacteria are members of the oral and vaginal flora and are recovered from anaerobic infections of the respiratory tract.

*Pseudomonas* is a genus of Gram-negative aerobic gammaproteobacteria.

*Staphylococcus* is a genus of Gram-positive bacteria, with round appearance, so-called cocci. *Staphylococcus* bacteria form in grape-like clusters.

*Streptococcus* is a genus of spherical Gram-positive bacteria belonging to the phylum Firmicutes and the lactic acid bacterial group. Some *Streptococci* are probiotic. For example, *Streptococcus thermophilus* is a probiotic used to make yogurt. Breaking down lactose to create lactase, the enzyme that digests milk sugars, this species can help with lactose intolerance. Other important *Streptococcus* strains include *cremoris, faecium* and *infantis*.

*Citrobacter* is a genus of Gram-negative coliform bacteria in the Enterobacteriaceae family. The species *C. amalonaticus, C. koseri*, and *C. freundii* can use citrate as a sole carbon source.

*Enterobacter* is a genus of common Gram-negative, facultatively anaerobic, rod-shaped, non-spore-forming bacteria of the family Enterobacteriaceae. Examples of *Enterobacter* are *Escherichia coli, Salmonella typhimurium, Pseudomonas aeruginosa, Acinetobacter baumannii, Klebsiella pneumonia*, and *Stenotrophomonas maltophilia*.

*Escherichia* is a genus of Gram-negative, non-spore forming, facultatively anaerobic, rod-shaped bacteria from the family Enterobacteriaceae.

*Klebsiella* is a genus of non-motile, Gram-negative, oxidase-negative, rod-shaped bacteria with a prominent polysaccharide-based capsule, from the family Enterobacteriaceae.

*Proteus* is a genus of Gram-negative Proteobacteria, from the family Enterobacteriaceae.

*Salmonella* is a genus of rod-shaped, Gram-negative bacteria, from the family Enterobacteriaceae. There are only two species of *Salmonella, Salmonella bongori* and *Salmonella enterica*, of which there are around six subspecies. *Salmonella* cause illnesses such as typhoid fever, paratyphoid fever, and food poisoning. *Salmonella* species are facultative intracellular pathogens.

*Yersinia* is a genus of Gram-negative rod shaped bacteria from the family Enterobacteriaceae, which are facultative anaerobes. Some members of *Yersinia* are pathogenic in humans. In particular, *Y. pestis* is the causative agent of the plague. Rodents are the natural reservoirs of *Yersinia* and, less frequently, other mammals serve as the host. Infection may occur through blood, or via consumption of food products contaminated with infected urine or feces.

The term "MDR" as used in accordance with the present invention, refers to a multi drug resistant bacterial strain.

The term "disease" in the context of the present invention shall refer to any disease or condition indicated as negatively affecting, in any kind of way, a human being. The term "dysbiosis" (also called dysbacteriosis) shall refer to any kind of imbalance of the microbiome. For example, species that are normally underrepresented in the microbiome of a healthy human being become overrepresented during the condition of dysbiosis, whereas normally dominated species of a healthy human being become underrepresented during the condition of dysbiosis. Most often, dysbiosis is a condition in the gastrointestinal tract, particularly during small intestinal bacterial overgrowth (SIBO) or small intestinal fungal overgrowth (SIFO). Dysbiosis has been reported to be associated with illnesses, such as inflammatory bowel disease, bacterial vaginosis, and colitis.

The term "gastrointestinal disorder" shall include any disturbance of the gastrointestinal tract. Examples of gastrointestinal disorders are, without being limited thereto, gastrointestinal motility disorder, irritable bowel syndrome, constipation, a functional gastrointestinal disorder, gastroesophageal reflux disease, functional heartburn, dysbiosis, dyspepsia, functional dyspepsia, nonulcer dyspepsia, gastroparesis, chronic intestinal pseudo-obstruction, colonic pseudo-obstruction, Crohn's disease, colitis, ulcerative colitis, inflammatory bowel disease, diverticulitis, gluten and/or lactose intolerance, obesity, stomach rumble, small intestinal bacterial overgrowth (SIBO), small intestinal fungal overgrowth (SIFO), meteorism, and flatulence.

A "proliferative disease" in the context of the present invention shall preferably refer to a disease such as a cancer or a tumor disease. Cancer diseases that can be treated by the compound of the present invention include, but are not limited to, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma, pleomorphic adenoma, hepatocellular carcinoma, and/or adenocarcinoma.

The term "commensal" refers to organisms that are normally harmless to a host, and can also establish mutualistic relations with the host. The human body contains about 100 trillion commensal organisms, which have been suggested to outnumber human cells by a factor to 10.

The term "compound" as used herein is used to describe any specific compound or bioactive agent disclosed herein, including any and all stereoisomers (including diasteromers) if applicable, individual optical isomers (enantiomers) or racemic mixtures, pharmaceutically acceptable salts, prodrug forms, including hydrates and solvates of these compounds. The term compound herein refers to stable compounds. Within its use in context, the term compound may refer to a single compound or a mixture of compounds as otherwise described herein.

In the context of the present invention the term "subject", as used in certain embodiments, preferably refers to a mammal, such as a mouse, rat, guinea pig, rabbit, horse, cattle, cow, cat, dog, monkey, or preferably a human. The subject of the invention may be at danger of suffering from a disease, such as a bacterial infection, a viral infection, a fungal infection, and a parasitic infection. A more detailed description of medical indications relevant in context of the invention is provided herein elsewhere.

Treatment is meant to include, e.g., treating, delaying or alleviating disease progression, reducing the symptoms of, or curing the disease or condition. An "effective amount" is an amount of the compound(s) or the pharmaceutical composition as described herein that alleviates symptoms as found for the disease to be treated, such as a cancer disease. Alleviating is meant to include, e.g., preventing, treating, reducing the symptoms of, or curing the disease or condition. The invention also includes a method for treating a subject at risk for a development and/or progression of a cancer disease, wherein a therapeutically effective amount of a compound as described above is provided. Being at risk for the disease can result from, e.g., a family history of the disease, a genotype, which predisposes to the disease, or phenotypic symptoms, which predispose to the disease. In one embodiment, as used herein, the term "prevention" or "preventing" when used in the context of a subject refers to stopping, hindering, and/or slowing down the development or onset of a proliferative disease and in in particular the symptoms associated with the proliferative disease.

The term "effective" is used herein, unless otherwise indicated, to describe an amount of a compound or component, which, when used within the context of its use, produces or effects an intended result, whether that result relates to the prophylaxis and/or therapy of a disease state, a secondary disease state or condition thereof or as otherwise described herein. The term effective subsumes all other effective amount or effective concentration terms (including the term "therapeutically effective") which are otherwise described or used in the present application.

The dosage regimen of a compound will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

The term "antibiotic", as used herein, relates to a chemical substance, which at low concentrations kills or prevents the growth of certain microorganisms, generally bacteria, although some antibiotics are also used for the treatment of infections by fungi or protozoa. Antibiotics are used in human, animal or horticultural medicine to treat infections caused by microorganisms. Antibiotics included in the present invention are, without being limited thereto, aminoglycoside antibiotics, ansamycins, carbacefems, carbapenems, cephalosporins, glycopeptides, glycylcyclines, macrolides, monobactams, penicillins, polypeptides, quinolones, fluoroquinolones, sulphonamides, beta-lactams, tetracyclines and others such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide antibiotics, polymixins, quinupristin/dalfopristin, rifampin, rifampicin, tinidazole, viomycin and capreomycin.

EXAMPLES

The inventors explored the media growth profiles of a large, phylogenetically representative panel of human gut bacteria across 4 rich and 15 defined media. This allowed the inventors to characterize their nutritional selectivity of different gut microbiome species, the inventors analyzed the preferences, accurately mapped their biosynthetic capabilities, discovered hitherto unknown metabolic features of several bacteria, and contextualized growth characteristics in terms of gut microbiota ecology.

For measuring and/or detecting of the species as described herein, standard methods can be used, such as, for example, a method selected from the group of PCR, high-throughput sequencing, metatranscriptomic sequencing, antibodies, and 16S rDNA analysis.

Selection of Representative Gut Bacterial Species

Figure 1A:
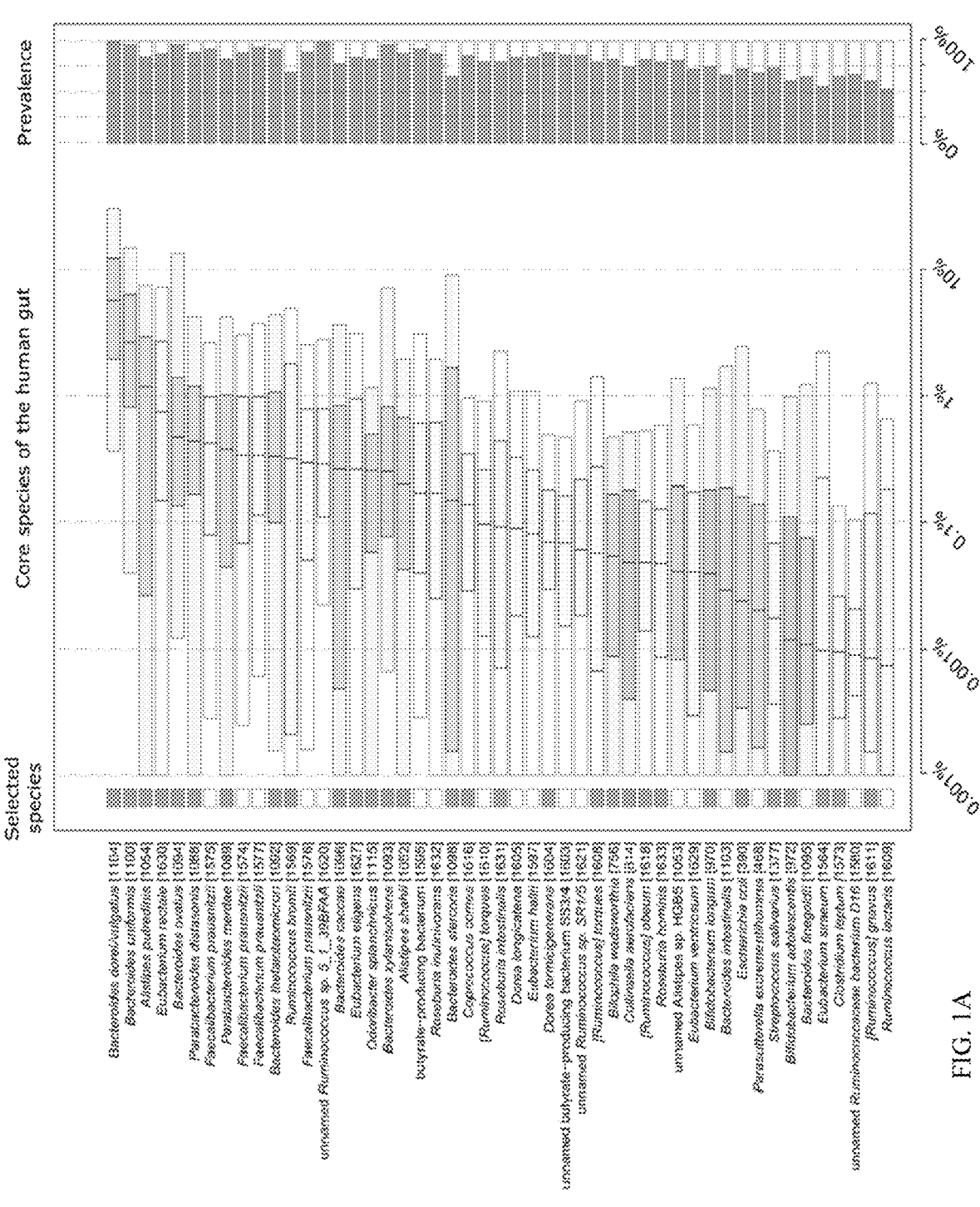
Figure 1B:
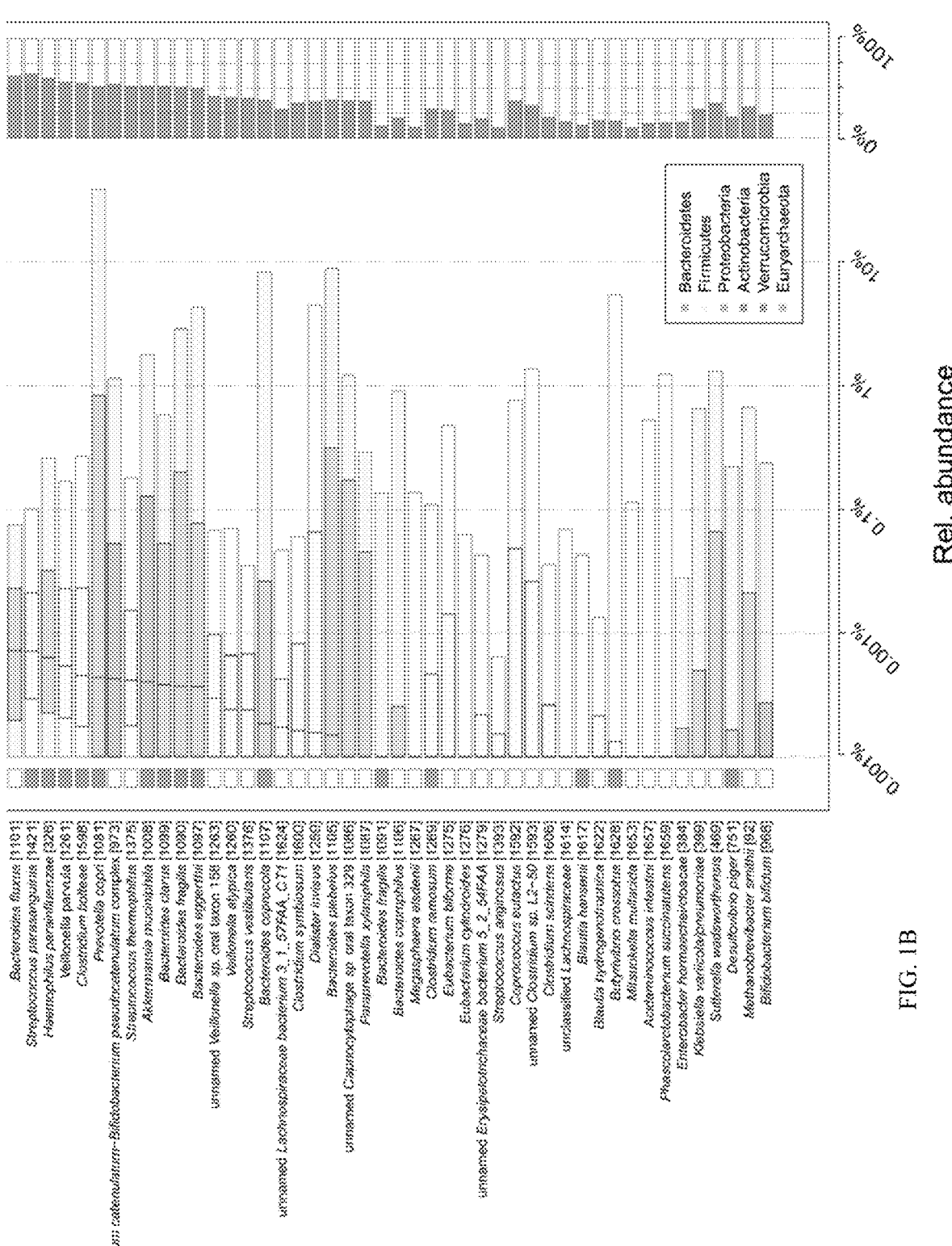
Figures 2A, 2B, 2C, 2D:
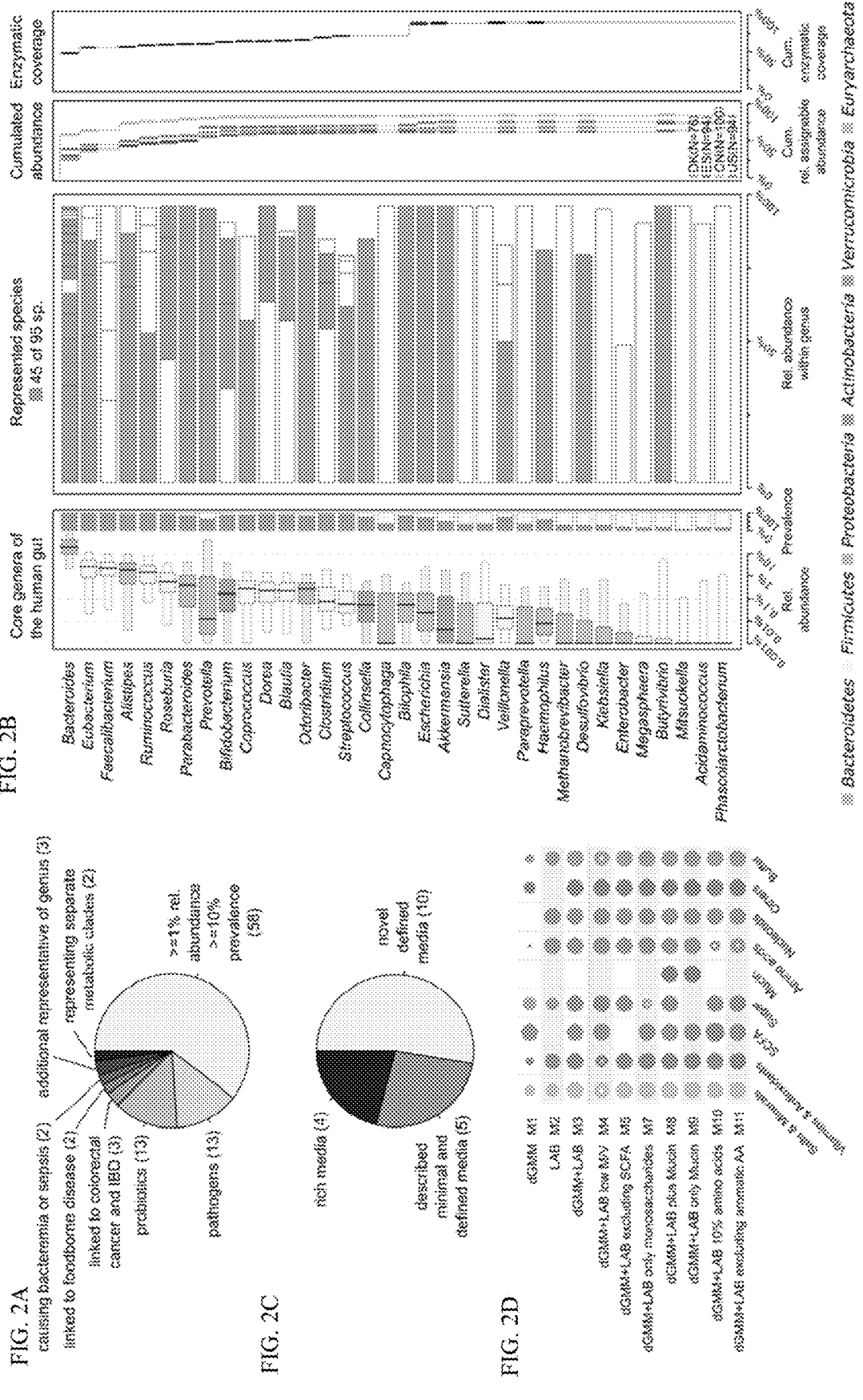

To cover a wide range of phylogenetically as well as metabolically diverse representatives of a healthy human gut flora, the inventors selected a total of 96 bacterial strains from 72 species. First, 57 species commonly occurring within the human population—meeting the criteria of relative abundance of 1% or more in at least one sample and a prevalence of more than 10%—were preselected from published metagenomics datasets collected in four countries from a total of 364 healthy humans (FIG. 1, FIG. 2b). From these, 58 cultivable bacterial strains from 45 species preferably with publicly available and annotated genomes were selected. The inventors further added thirteen probiotics from the genera *Lactobacillus* and *Lactococcus*, thirteen pathogens (from the genera of *Salmonella, Shigella, Vibrio* and *Yersinia* plus enteropathogenic *Escherichia*), three *Fusobacterium* strains linked to colorectal cancer and inflammatory bowel disease (IBD), one additional representative of the *Coprococcus, Eubacterium* and *Prevotella* genus and six species possessing uncommon metabolic pathways such as *Eggerthela lenta* (EC numbers 1.3.99 and 2.1.4; known for digoxin inactivation), *Pseudoflavonifractor capillosus* (EC numbers 2.7.10, 6.1.2 and 1.5.98), *Clostridium saccharolyticum* (EC number 1.11.2) and *Clostridium perfringens* (EC numbers 1.3.99 and 1.7.7). The final species collection thus represents not only highly abundant and prevalent genera but also important species linked to colorectal cancer, IBD, infectious disease and taxa of beneficial probiotics (FIG. 2a). The selected bacteria, taking into account the so far sequenced species, represent a cumulative enzyme coverage, at EC level 4, of close to 90% when mapping to 364 human gut metagenomes of healthy individuals and cumulative abundance coverage of 72% on average across metagenomics 75 datasets (FIG. 2b).

Importantly, a panel consisting of *Bacteroides, Eubacterium, Faecalibacterium, Alistipes, Ruminococcus, Roseburia, Parabacteroides, Prevotella, Bifidobacterium, Coprococcus, Dorea, Blautia, Odoribacter, Clostridium, Streptococcus, Collinsella, Capnocytophaha,* and *Bilophila* represents a cumulative enzyme coverage of close to 85% when mapping to 364 human gut metagenomes of healthy individuals (FIG. 2).

Media Selection and Design

For the vast majority of the selected 96 strains, neither growth characterization data nor defined growth media were previously available. To our knowledge, only 6 defined or minimal media had so far been established for a subset of bacterial strains, namely for *Escherichia coli, Bacteroides thetaiotaomicron, Veillonella parvula, Clostridium perfringens, Bacteroides caccae* and *Lactobacillus rhamnosus*. To enable detailed metabolic characterization of all 96 strains, the inventors designed several defined media by taking into account various known metabolic requirements of gut bacterial species. The inventors developed a chemically defined version of the gut microbiota medium (GMM) by excluding all non-defined compounds such as yeast and meat extract. Another defined medium was prepared by combining the Zhang-Mills-Block and a chemically defined medium described by Wegkamp et al. supporting growth of various lactic acid bacteria (hereafter referred to as LAB medium). A mixture of the defined GMM (dGMM) and the LAB medium supplemented with 1 g/L lactose, 0.5 mg/L hemin and 2 mg/L ß-NAD, named dGMM+LAB, formed the basis for all other newly compounded media. These were obtained by excluding either short chain fatty acids (SOFA) or aromatic amino acids, by lowering the amounts of minerals and vitamins or by reducing the amounts of amino acids to 10%. Three more media either contained additional mucin, mucin as the sole carbohydrate source, or monosaccharides as carbohydrate source (FIG. 2d). The inventors further expanded the media set by including defined and minimal media (MM) previously described for *Bacteroides thetaiotaomicron, Clostridium perfringens* and *Veillonella parvula* and two modified versions of the *E. coli* MM (FIG. 2c). To allow for the growth of more fastidious organisms, four rich media used for cultivation of gut microbial communities or individual species were also included: GMM, mGAM (modified Gifu anaerobic medium broth, HyServe), WCA (Wilkinson Chalgren anaerobic agar, Sigma-Aldrich) and BHI (brain heart infusion broth, Sigma-Aldrich) supplemented with 0.5 mg/L hemin and 2 mg/L ß-NAD (BHI++). Together, the final set consisted of 15 defined and 4 rich media (FIG. 2c).

Growth Profiles Reveal Complex Evolution of Nutritional Preferences

Figure 3A:
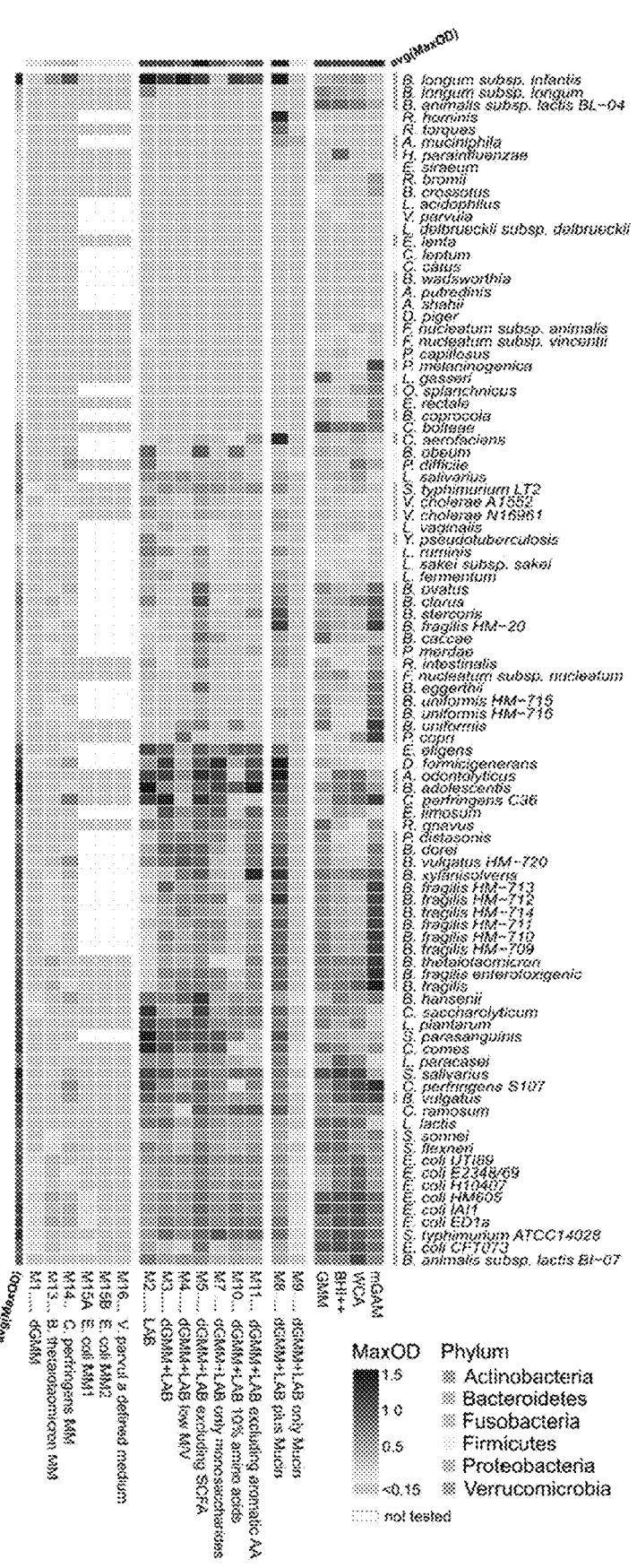
Figures 3B, 3C:
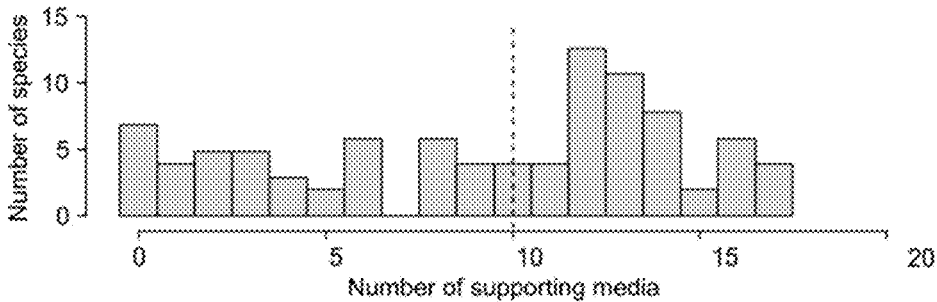

The inventors evaluated the selected bacterial strains for their growth performance across all 19 media. All cultivations were carried out under anaerobic conditions and growth was monitored by measuring optical density for up to 48 hours. Notably, the vast majority of the strains, 86 out of 96, grew in at least one defined medium. The median number of growth-enabling media across different species is 13, and the median number of species supported across different media is 63 (FIG. 3a-c). Altogether, our media set allowed growth of phylogenetically as well as functionally diverse gut bacteria in complex as well as defined media. Fastidious behavior was observed for many species. Interestingly, this is not confined to any particular phylogenetic division: thirteen species growing in four or less media are from ten different genera (five phyla), while other tested members of the same genera act more like generalists showing growth in five or more media. For example, while one of the two *Coprococcus* species, *C. catus*, is clearly very fastidious and could not grow in any of the here tested media, *C. comes* grew in fourteen different media within our screen. Such divergent growth patterns are observed across most genera.

Figure 3D:
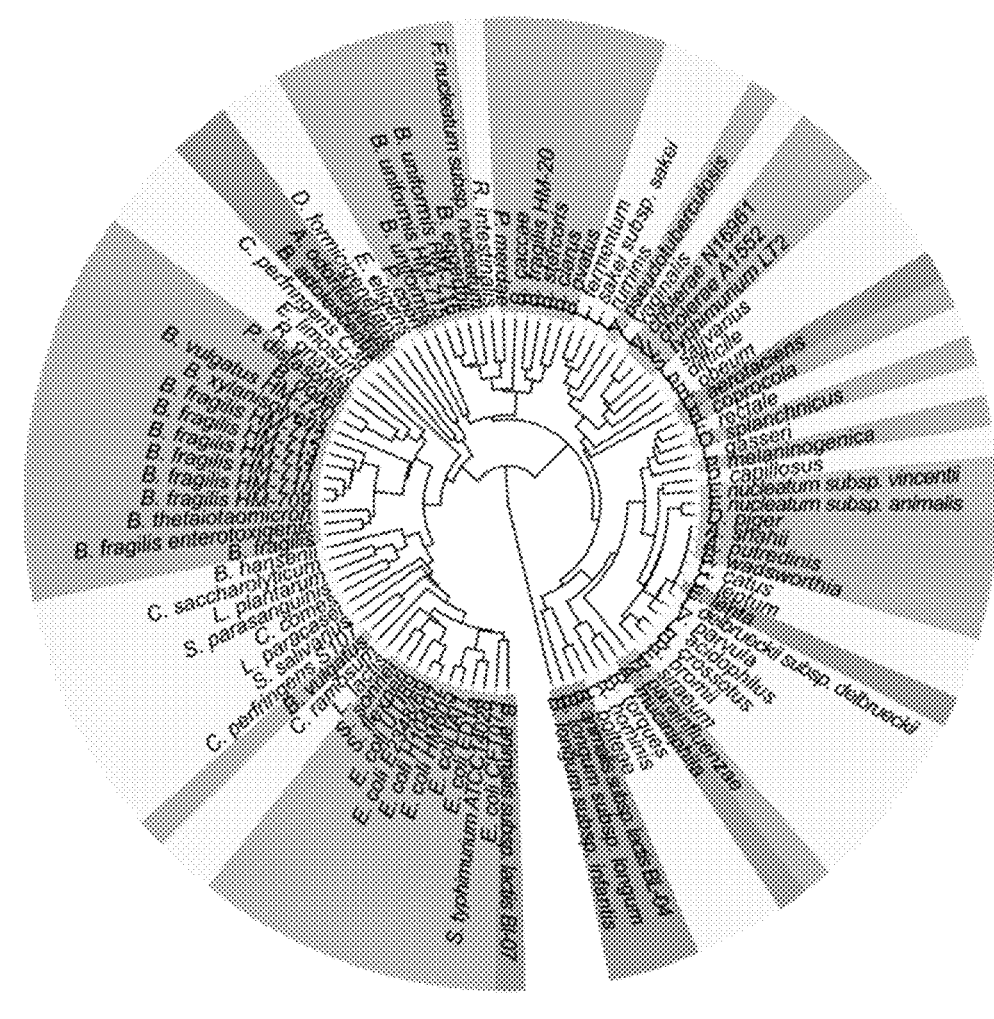
Figure 3E:
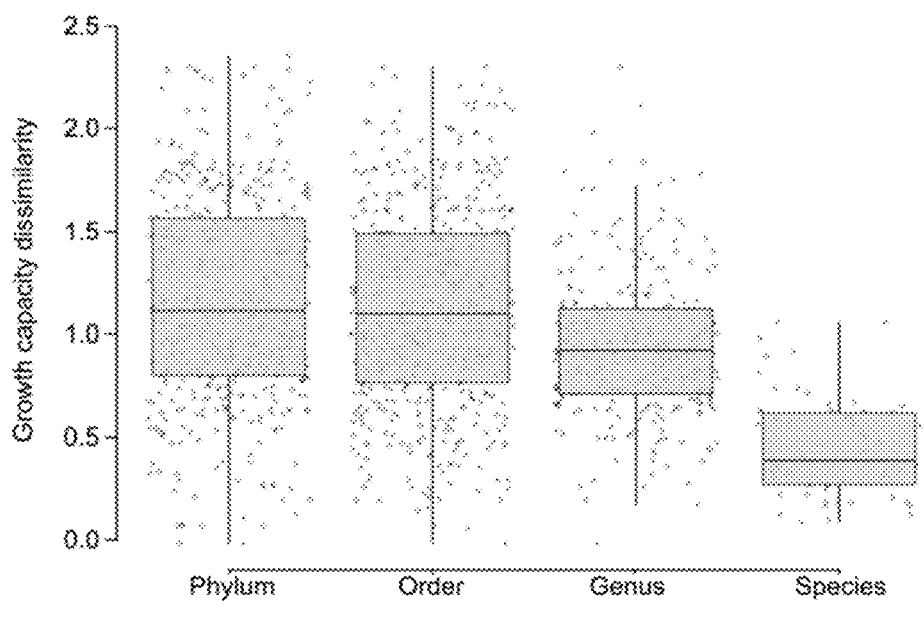
Figure 6A:
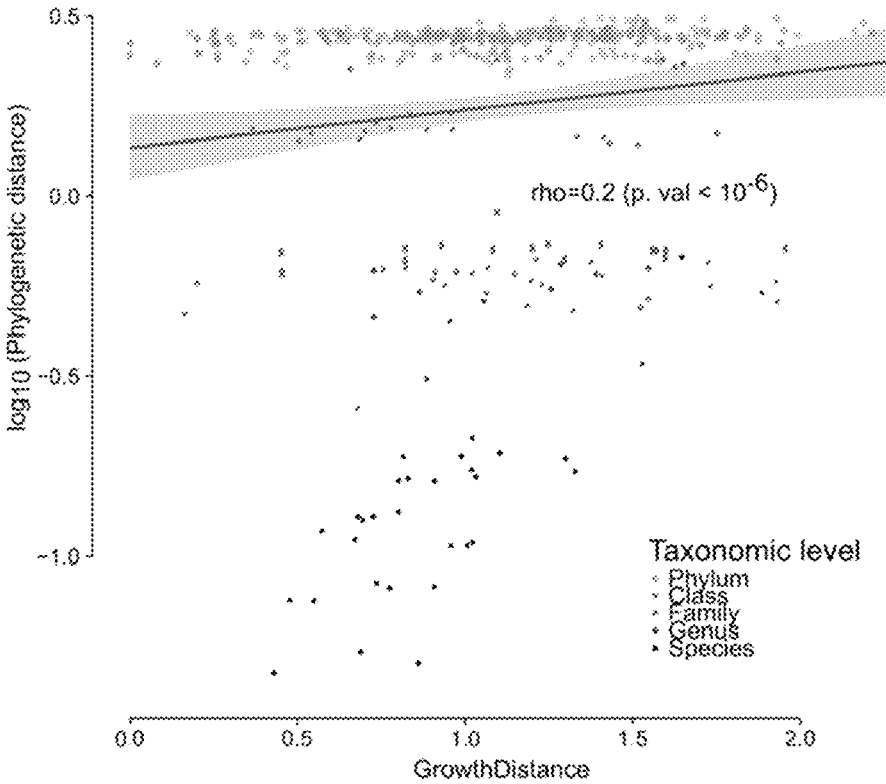
FIG. 6 shows the correlation between phylogenetic distance versus growth similarity. a, Correlation between phylogenetic distance and growth distance for all strains included in the inventor's study. b, Spearman's rho and corresponding p-values when comparing phylogenetic distance and growth distance within different taxonomic ranks.
Figure 6B:
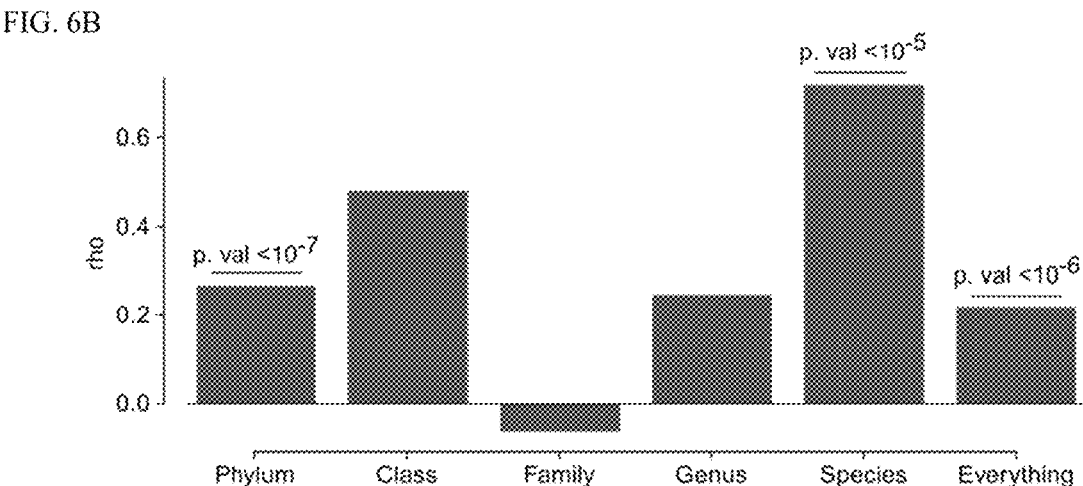

In case of *Bacteroides*, the most represented genus in this study, *B. coprocola*, *B. eggerthii*, *B. uniformis* HM-715 and HM-716 grew only in rich or specialized media. In contrast, *B. fragilis*, *B. thetaiotaomicron*, *B. vulgatus* and *B. uniformis* display generalist behavior growing in at least ten minimal or defined media and all four rich media. Similarly, among the *Bifidobacteria* strains, while *B. longum* subsp. *Longum* being very fastidious, *B. longum* subsp. *infantis* grew in ten defined media. The three strains of *Fusobacterium nucleatum* also show, despite being the same species, a very distinct growth pattern. While *Fusobacterium nucleatum* subsp. *nucleatum* and subsp. *animalis* grew in eleven and fifteen media respectively, *Fusobacterium nucleatum* subsp. *vincentii* only grew in four. Conversely, similar growth patterns were found between higher taxonomic ranks. For example, *Veillonella parvula* and *Blautia obeum*, two species from different classes, show similar preference for scarce nutritional conditions. Another pair of species, *Akkermansia muciniphila* and *Ruminococcus torques*, which have been previously described to compete for a similar ecological niche in the mucus layer, displayed a noticeably similar growth pattern in our screen. Even from different phyla, both species were growing under three particular media conditions, namely mGAM and the two defined media containing mucin. Overall, growth patterns reflecting phylogeny as well as those implying parallel or convergent evolution towards the same metabolic niche are apparent across most taxonomic clades from order to strain level (FIG. 3d, e; FIG. 6).

In Vitro Growth Correlates with Abundance in the Human Gut Microbiome

Figure 4A:
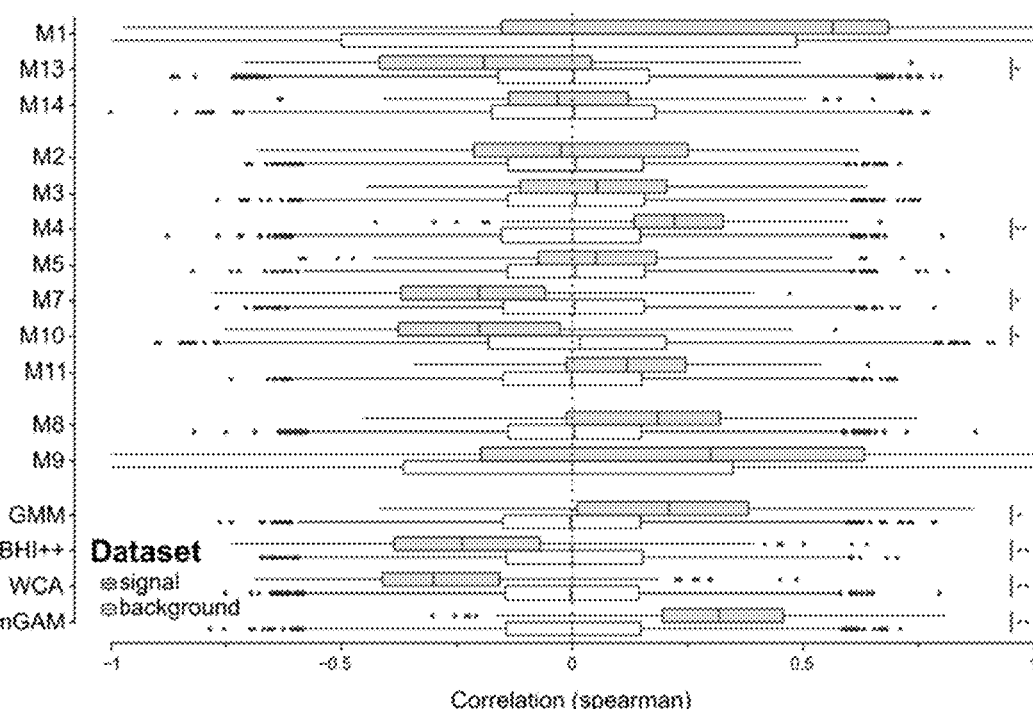
Figure 4B:
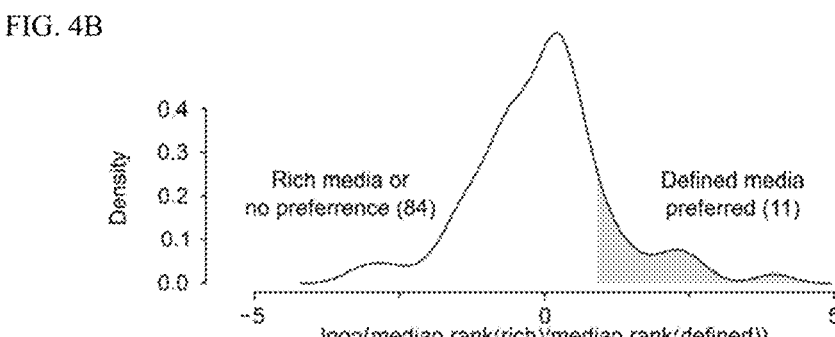
Figure 4C:
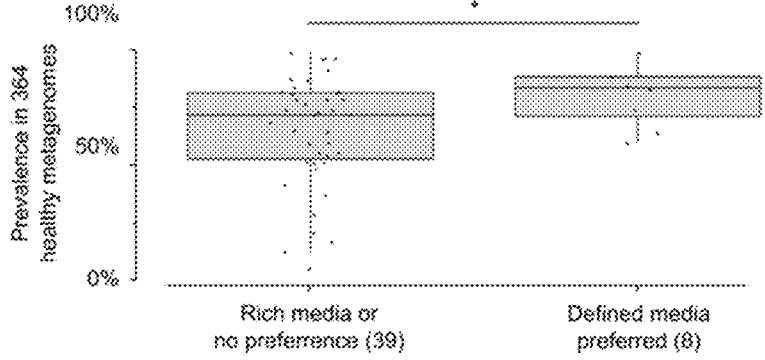
Figure 7:
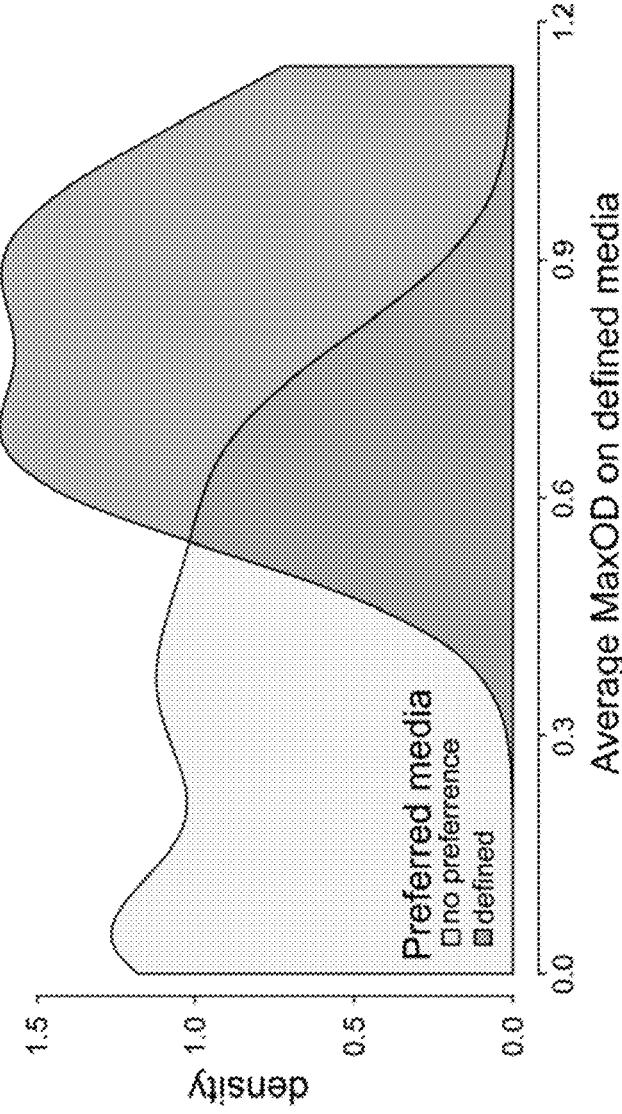
FIG. 7 shows the distribution of Average Maximum OD in defined media. Shown is a comparison between species preferring defined media and others (p-value 3.048e-06).

The inventors next analyzed growth characteristics of bacteria in context of their standing in the gut microbiota community. For this, the inventors correlated growth capacity of the species (maximum OD reached) in each of the 19 media with their abundance in the gut metagenomes 166 of each of the 364 healthy individuals. Indeed, several of the tested media showed a significant positive correlation (FIG. 4a). Among these, mGAM and M4 displayed the highest frequency of positive correlations suggesting that these more closely mimic growth conditions in the gut and hence making them the media of choice for in vitro studies. Furthermore, as many as 10 species grow better in defined media than in rich (FIG. 4b), and within defined media show stronger growth than the others (FIG. 7). The inventors hypothesized that the metabolic robustness of these species would enable survival in limiting environments. Indeed, the inventors find that these species are more prevalent in the gut metagenomes of healthy individuals, likely representing diverse gut environments with different nutrient limitations (FIG. 4c).

Community Study

The inventors found that a sub-community of the initial inoculum mix (up to 20 or more bacteria depending on conditions) is surviving passaging as a community. In the context of this invention, a species is considered to be a "community member" above a threshold of 0.01% abundance. The inventors identified in vitro assembly of a stable bacterial community within 4 to 5 passages. Interestingly, different nutritional and pH environments lead to the assembly of different communities. Sequencing results and data obtained from metabolomics shows that variance between samples is dependent on nutritional and pH conditions. This method is useful in identifying interspecies interactions by rank correlation between monoculture growth and species abundance within the community. While ranks of species grown in monoculture/community in rich media correlate well, media scarce in nutritional compounds result in no or low correlation, implying to support interspecies interactions.

Short Chain Fatty Acids and Amino Acids Inhibit Growth of Several Gut Bacteria

The screen also allowed the inventors to assess inhibitory effects of SCFAs and amino acids, known to influence microbiome dynamics. SCFAs, especially acetate, propionate and butyrate, are major by-products of complex carbohydrate breakdown processes carried out by the gut bacterial community. SOFA play a major role in bacterial cross feeding, but are also linked to various host health conditions. Furthermore, SOFA are known to be toxic to both commensals and pathogens at low pH. The inventors observed that several species are also affected at the circumneutral pH relevant for the colorectal environment. Physiological levels of SOFA affected growth of fifteen species (FIG. 5a) in comparison to growth in standard dGMM+LAB medium. While SOFA boosted the growth of one species (*Lactobacillus vaginalis*), their presence considerably inhibited several phylogenetically diverse gut bacteria (FIG. 5a). To our knowledge, the growth inhibition of these species by SOFA has not been described before. The inventors also evaluated the inhibitory effect of amino acids on growth, as several gut commensals are known to be sensitive to (specific) amino acids. The inventors identified two strains, *B. fragilis* HM-20 and *B. xylanisolvens*, being sensitive to presence of aromatic amino acids while other species, such as *C. perfringens* C36, *R. hominis* and several *Lactobacillus* species, depended on these amino acids for robust growth (FIG. 4a). Furthermore, most tested species perform less well when total amino acid levels were reduced by 90%. In contrast, *Blautia obeum* and *Veillonella parvula* exhibited increased growth upon amino acid reduction (FIG. 5a). These two species also generally show better growth in defined media than in rich, and prefer media with nutrient exclusions (FIG. 3a), suggesting sensitivity towards nutrient excess.

Novel Mucin-Metabolizing Capability of Gut Bacteria

Only about a dozen species from four genera have, to our knowledge, so far been described as mucin degraders. Within the screen, a much larger number of species thrived in the presence of this biopolymer. The growth of 27 species was boosted in media supplemented with mucin and 36 species could survive with mucin as the sole carbohydrate source; 8 species overlapped between these two categories (FIG. 5b; FIG. 8). Among these, only three have previously been reported to metabolize mucin44. Furthermore, the newly identified degraders are likely to use yet unknown enzymes as only few or no known genes involved in mucin degrading pathways could be identified in the genomes of these species (FIG. 8a,b). The here identified mucin degraders include three strains from the *Bacteroides* genus, one strain from the family of Lachnospiraceae and one from the phylum Fusobacteria. The latter two phylogenetic groups have not yet been associated with mucin degradation. The inventor's data suggests more widespread mucin utilization capabilities among gut bacteria than currently appreciated.

Defined Media Resource Improves Prediction of Biosynthetic Capabilities of Gut Bacteria Defined media, in addition to permitting controlled cultivations, are a fundamental requirement for assessing biosynthetic capabilities of microorganisms. Genome-scale metabolic models can formalize this in a structured manner and allow studying effects of genetic and environmental perturbations as well as community behavior. Recently, a resource of 773 genome-scale metabolic models (AGORA models) of human gut bacteria was reported. These include 47 of the 96 strains tested in the inventor's screen. However, only four of these models could recapitulate growth on the inventor's experimentally validated media (FIG. 9a), suggesting that currently the information used to reconstruct these models (genome sequences and literature data, with defined media available for only a few species) is insufficient for capturing major metabolic capabilities of gut bacteria. Indeed, when the inventors used their defined media resource to improve these models (by filling the gaps in the network; FIG. 9b), the inventors could successfully recapitulate growth on experimentally observed media for 38 species (FIG. 9a). The remaining five bacteria may use yet unknown pathways or the model reconstruction may require extensive re-annotation to identify the missing functions. The gap-filled reactions in the improved models span several metabolic pathways ranging from central carbon metabolism to vitamin biosynthesis (FIG. 5c; FIG. 9b,d), many of which the inventors could additionally validate using genomic evidence from the TIGRFAM gene family database (FIG. 9c). The corresponding TIGRFAM sequence match scores are, however, only moderate—most likely due to annotation bias towards model organisms in the databases—and thus may explain why these reactions were missed in the original reconstruction. A comprehensive resource on defined media and growth requirements is thus indispensable for accurate reconstruction of metabolic models of gut bacteria.

Bacterial Depletion of Therapeutic Drugs is Widespread

Figures 15A, 15B:
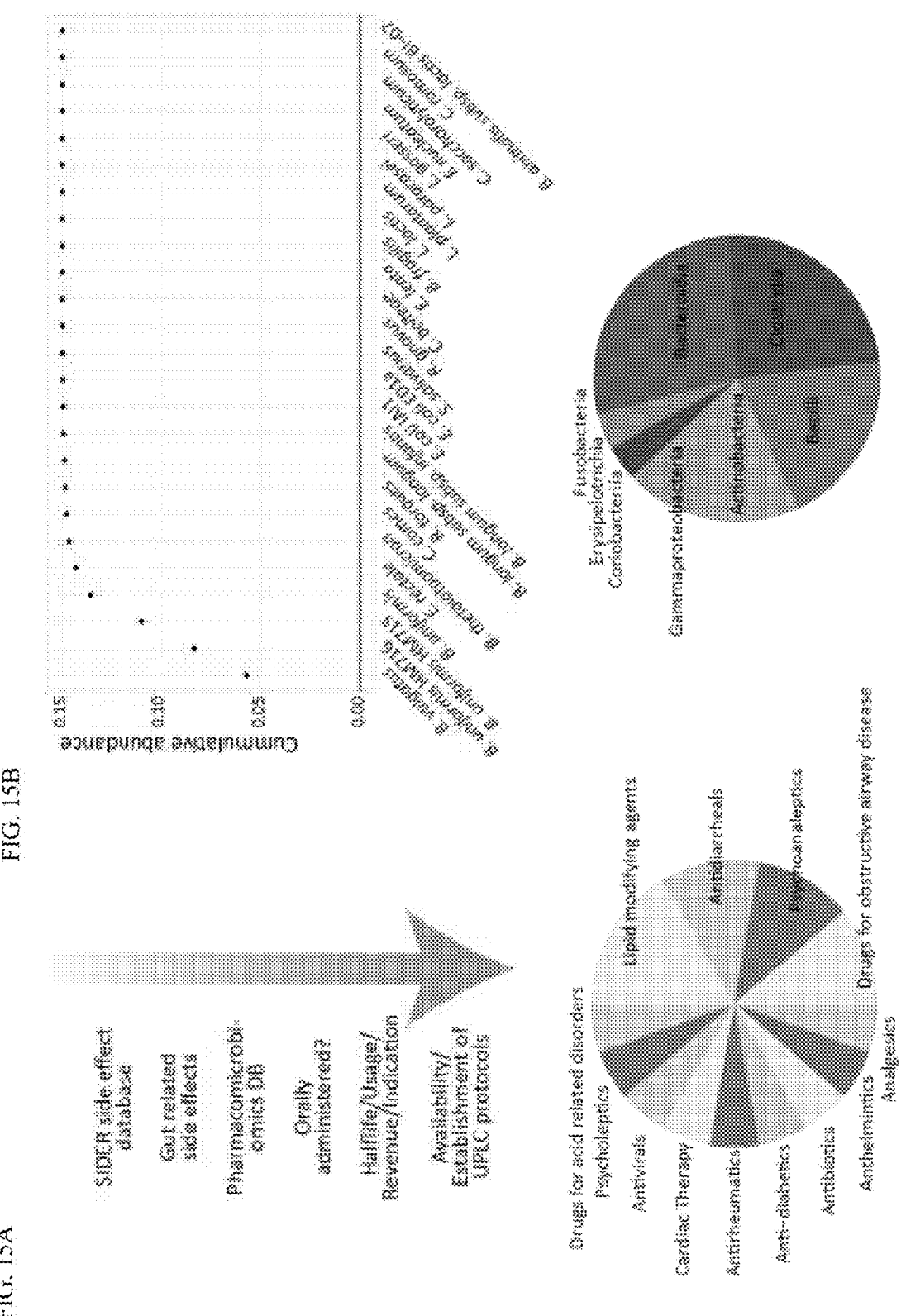
Figure 15C:
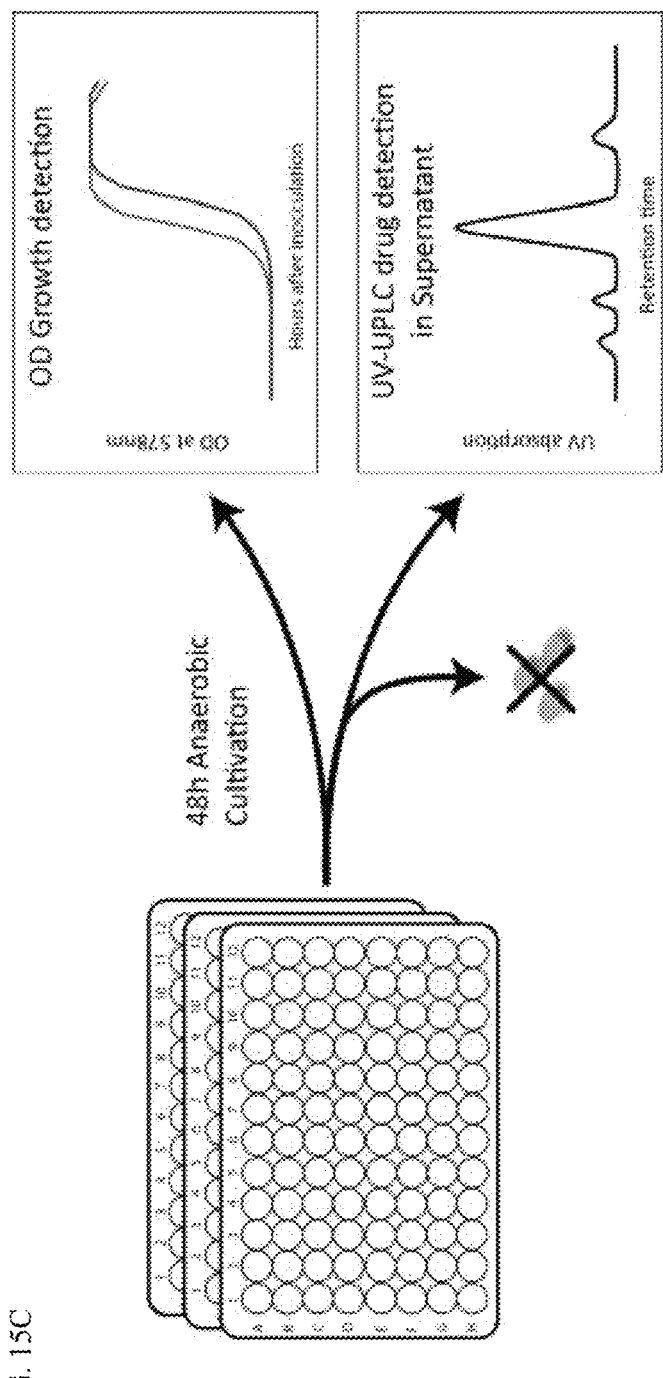

The inventors aimed to investigate the interactions between 15 human-targeted therapeutic drugs (FIG. 15a) and 25 gut bacterial strains (FIG. 15b). Orally administered small molecule drugs (MW<500 Da) were rationally selected to cover diverse areas of indication and both—gut related and unrelated—side effect profiles (FIG. 15a). The inventors screened for depletion of 50 µM of drug from the supernatant after 48 h anaerobic growth (FIG. 15c). As expected, the inventors found that metronidazole and sulfasalazine were depleted from the medium by most bacterial strains, whereas digoxin was only depleted by *E. lenta* (FIG. 15d). 6 out of 15 drugs (duloxetine, levamisole, montelukast, roflumilast, simvastatin, aripiprazole) were depleted around 50-60% by several strains and showed an overall shift towards depletion, indicating that many strains might deplete the drug slightly. Three additional drugs (loperamide, ranitidine and rosiglitazone) showed a similar trend but overall interactions were less strong for these. Interestingly, only two drugs (ezetimibe and acetaminophen) showed a high degree of specificity, interacting only with a few bacterial strains. Only 4 out of 15 drugs did not show any depletion in the screen. In summary, from 375 tested bacteria-drug interactions 49 revealed a depletion of a drug in the medium. The single tested *Fusobacterium F. nucleatum* accounts for 15% of the found drug depletion interactions. Bacteroidetes phyla on the other hand accounts for 24% of the interactions tested, but only for 16% of the depletion interactions found. Approximately 70% of tested human targeted drugs were depleted in the growth medium of at least one bacterial strain.

Figure 15D:
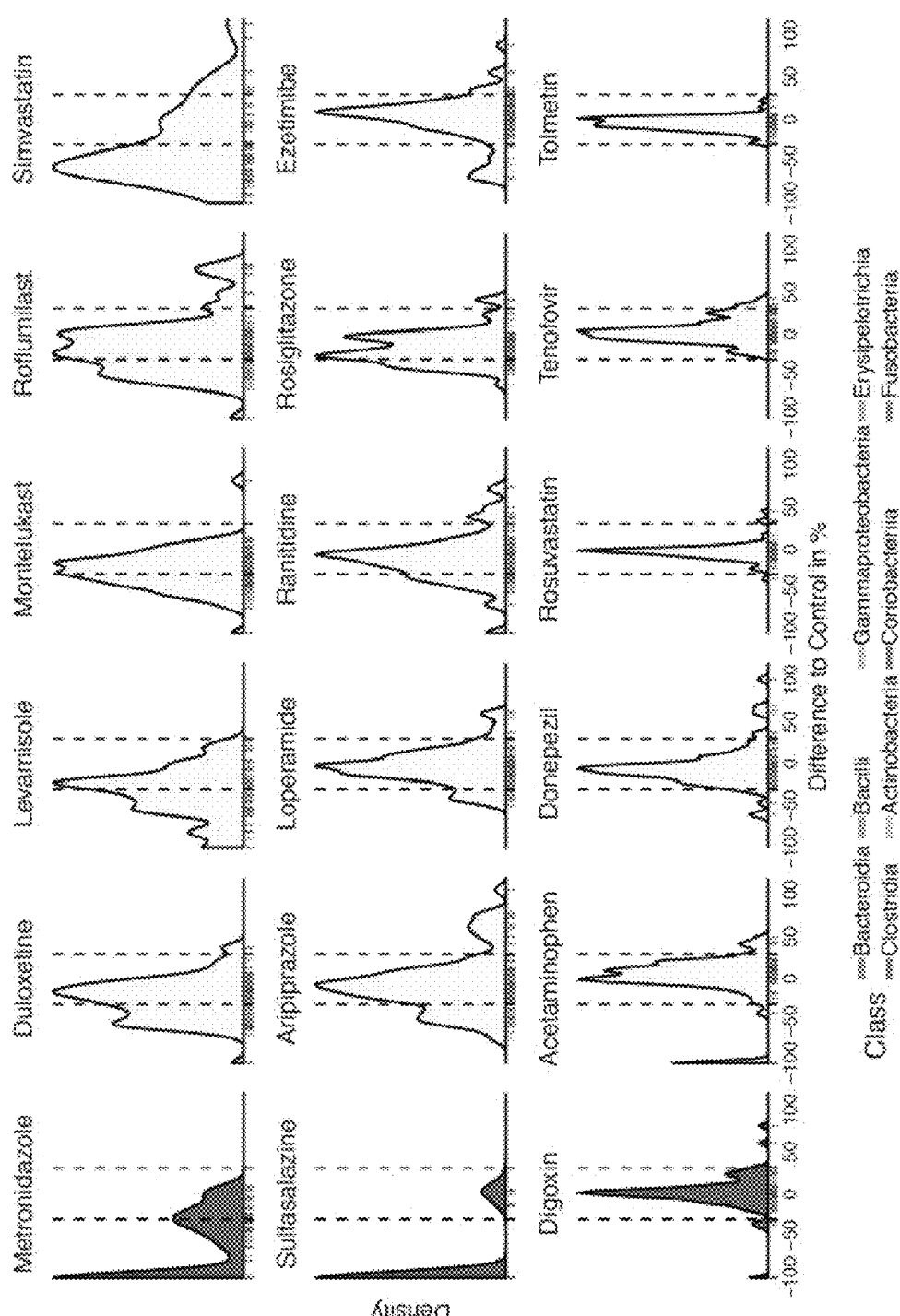
Figure 15E:
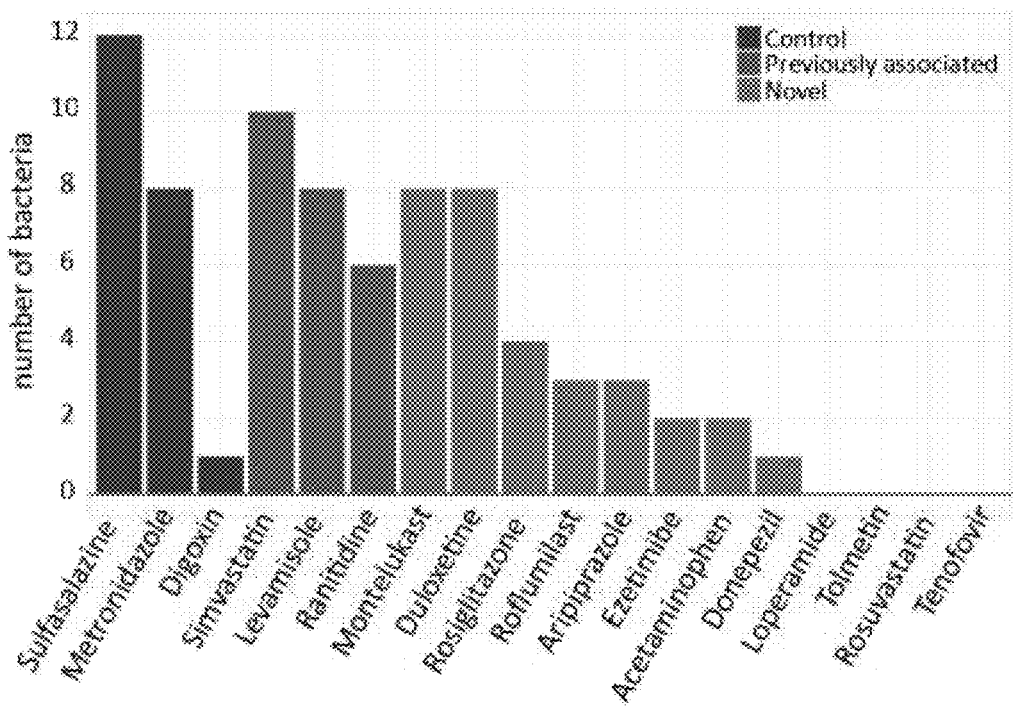
Figure 15F:
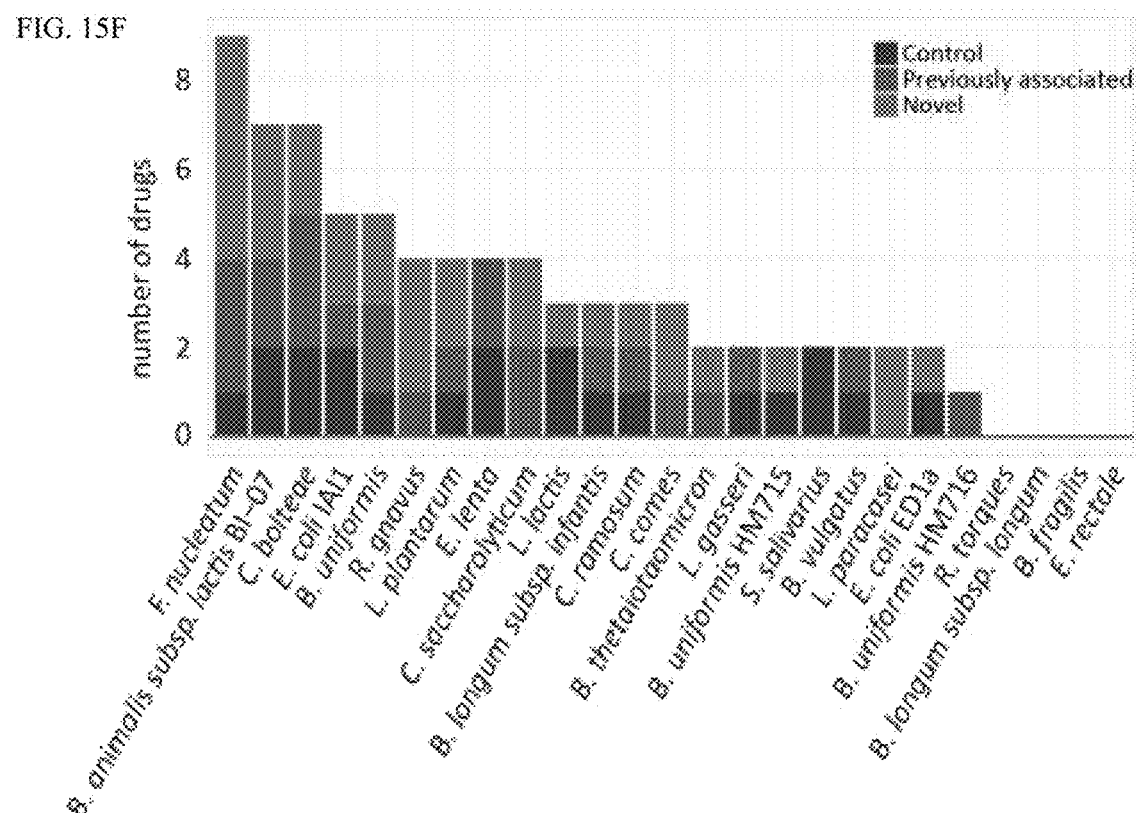

As digoxin is solely depleted by specific strains of *E. lenta* possessing a crg operon, the inventors applied a threshold of depletion at a minimum of 30% in both biological replicates (FIG. 15d). The inventors found that drugs which have been previously associated with bacterial metabolism are commonly depleted by 6-9 bacterial strains, whereas unassociated drugs are depleted by 1-4 different strains (FIG. 15e). Remarkably, in two cases the inventors found that also previously unassociated drugs can be depleted by up to eight bacterial strains. The inventors did not find that bacterial strains associated with diseases like *F. nucleatum* (colon cancer) or disease-associated *E. coli* strains are depleting more drugs than commensal bacteria like *C. bolteae* or *B. uniformis*. Also, common probiotics like *B. animalis* subsp. *lactis* or *L. plantarum* deplete several drugs from their growth medium (FIG. 15f). Remarkably, drug depletion seems to be a strain rather than species depending trait as different *E. coli* and *B. uniformis* strains show different tendencies to interact with drugs. 80% of the tested bacterial strains deplete at least one human-targeted drug.

Bioaccumulation is the Predominant Mode of Bacterial Drug Depletion

Figure 16B:
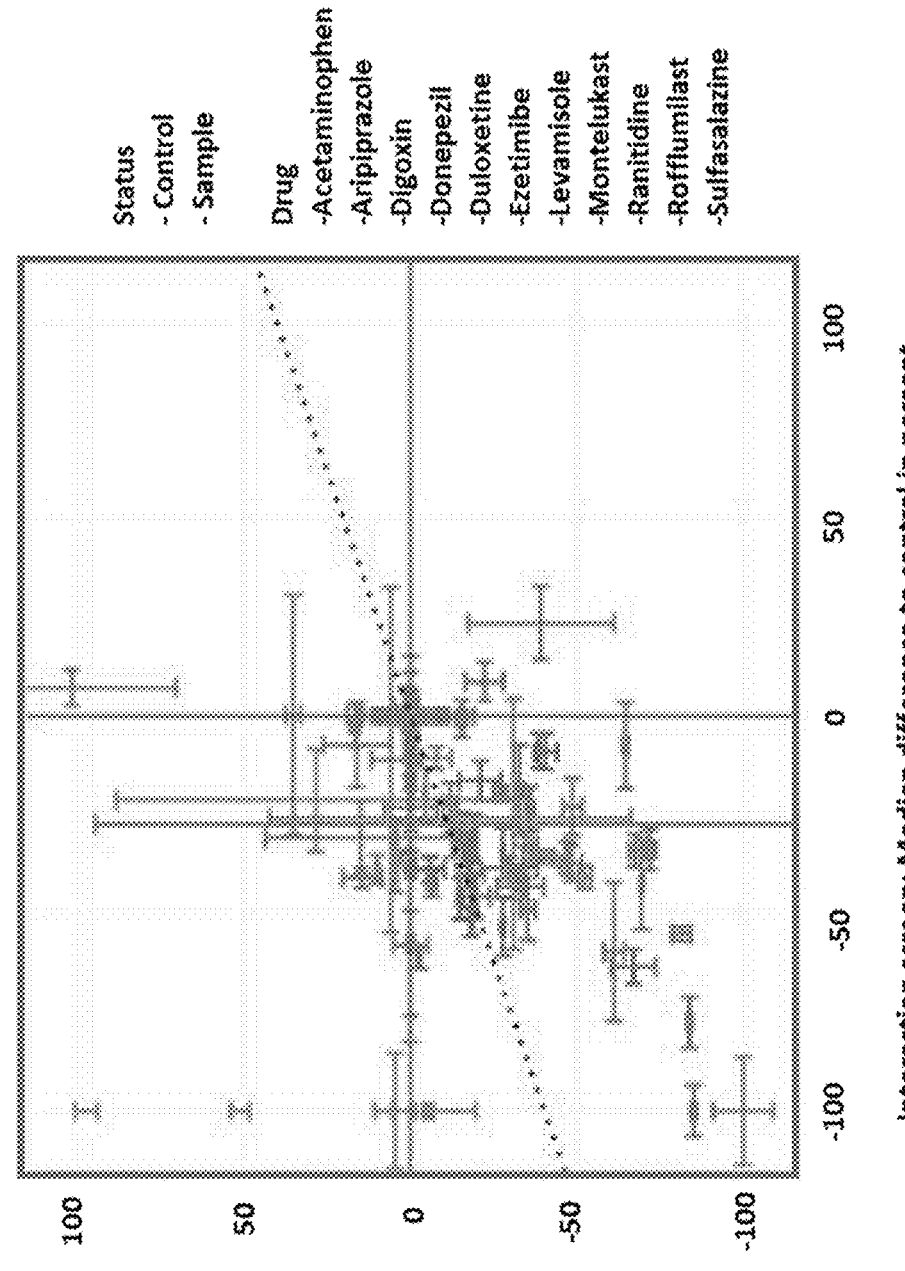
Figure 16C:
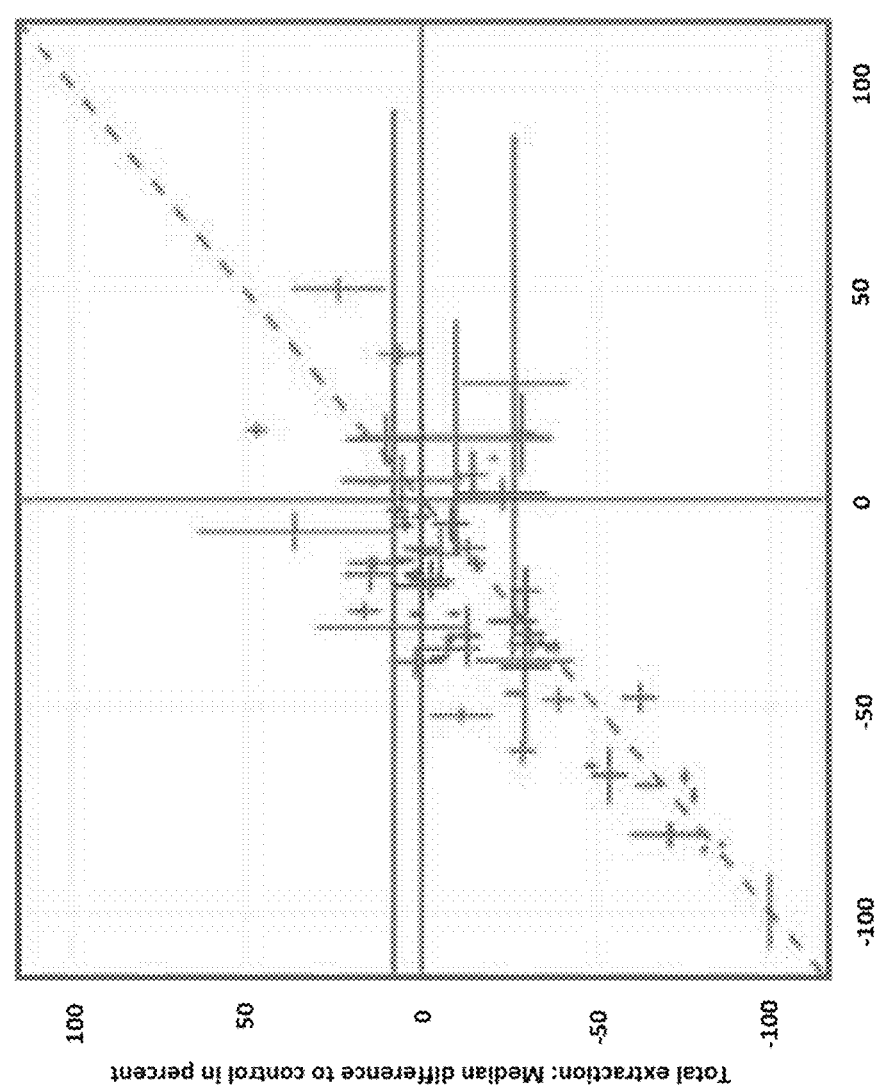
Figure 16D:
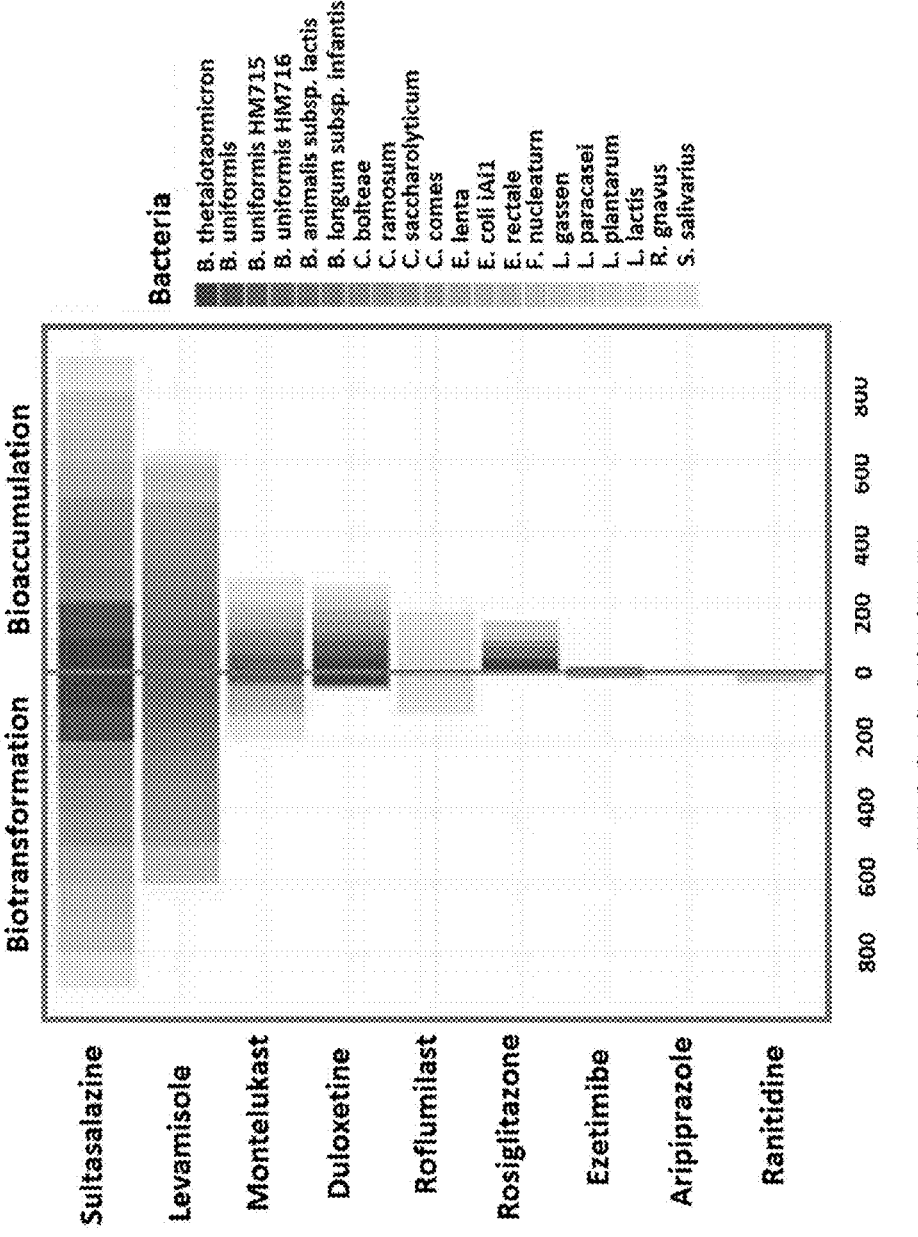
Figure 16E:
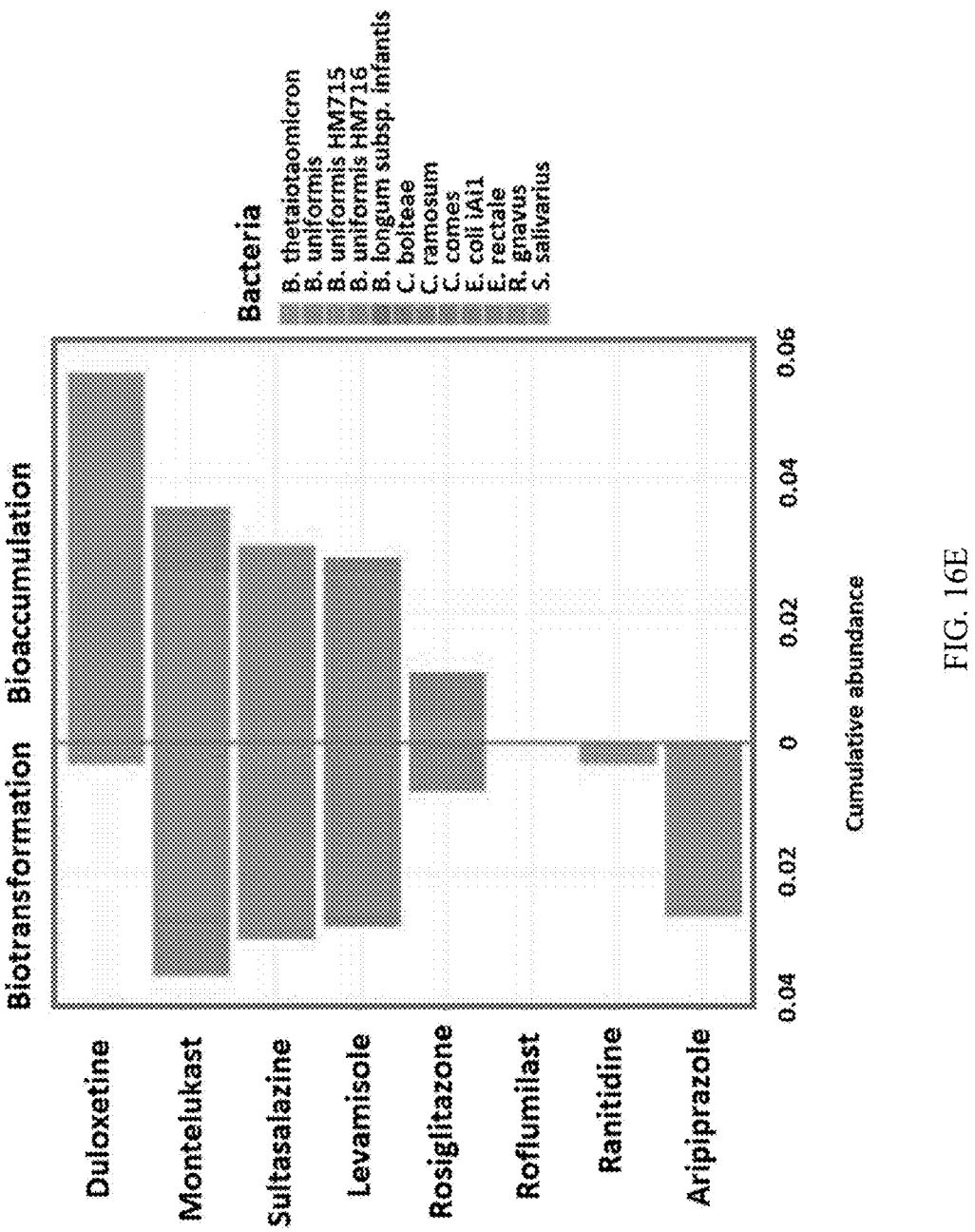
Figure 16F:
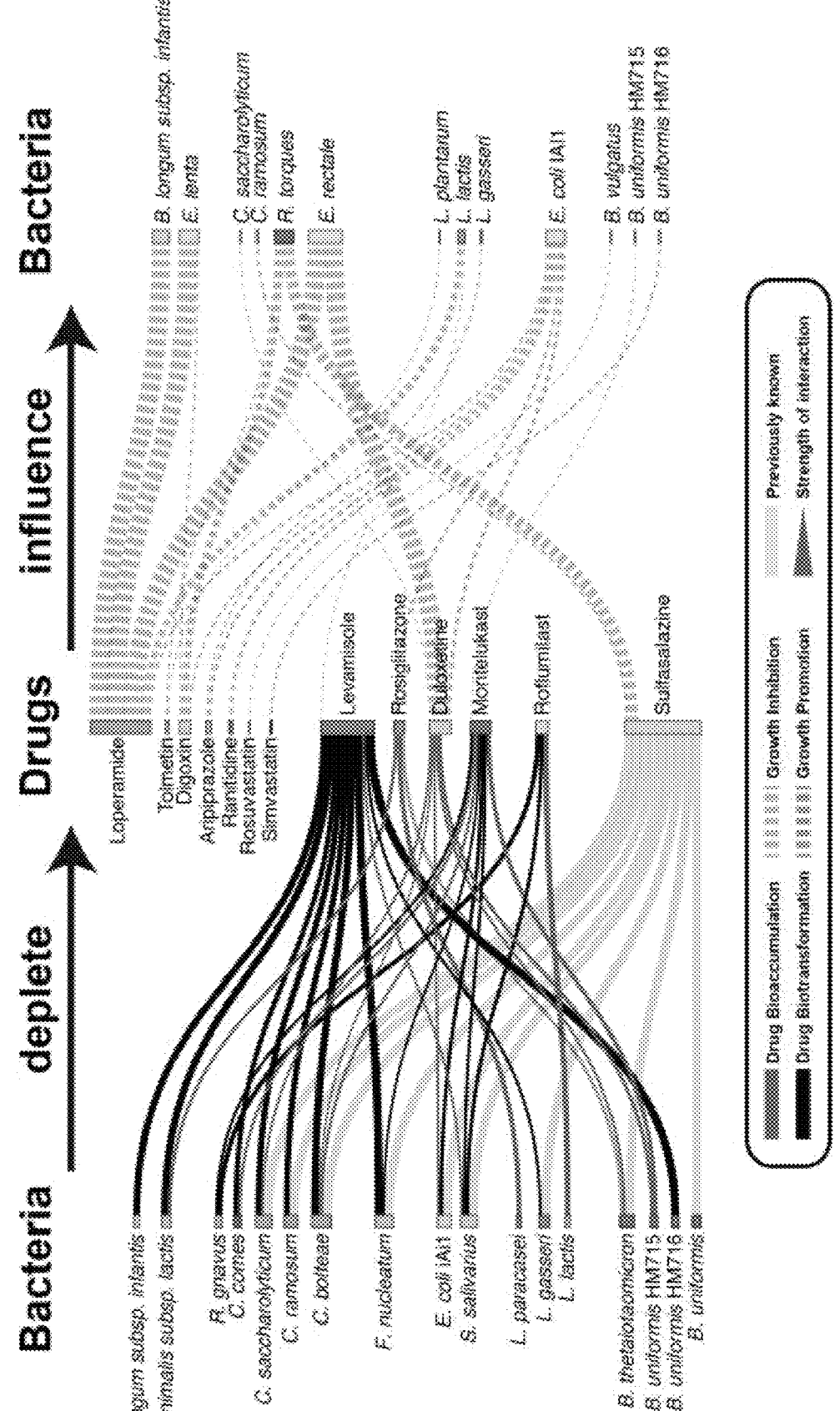
Figure 17D:
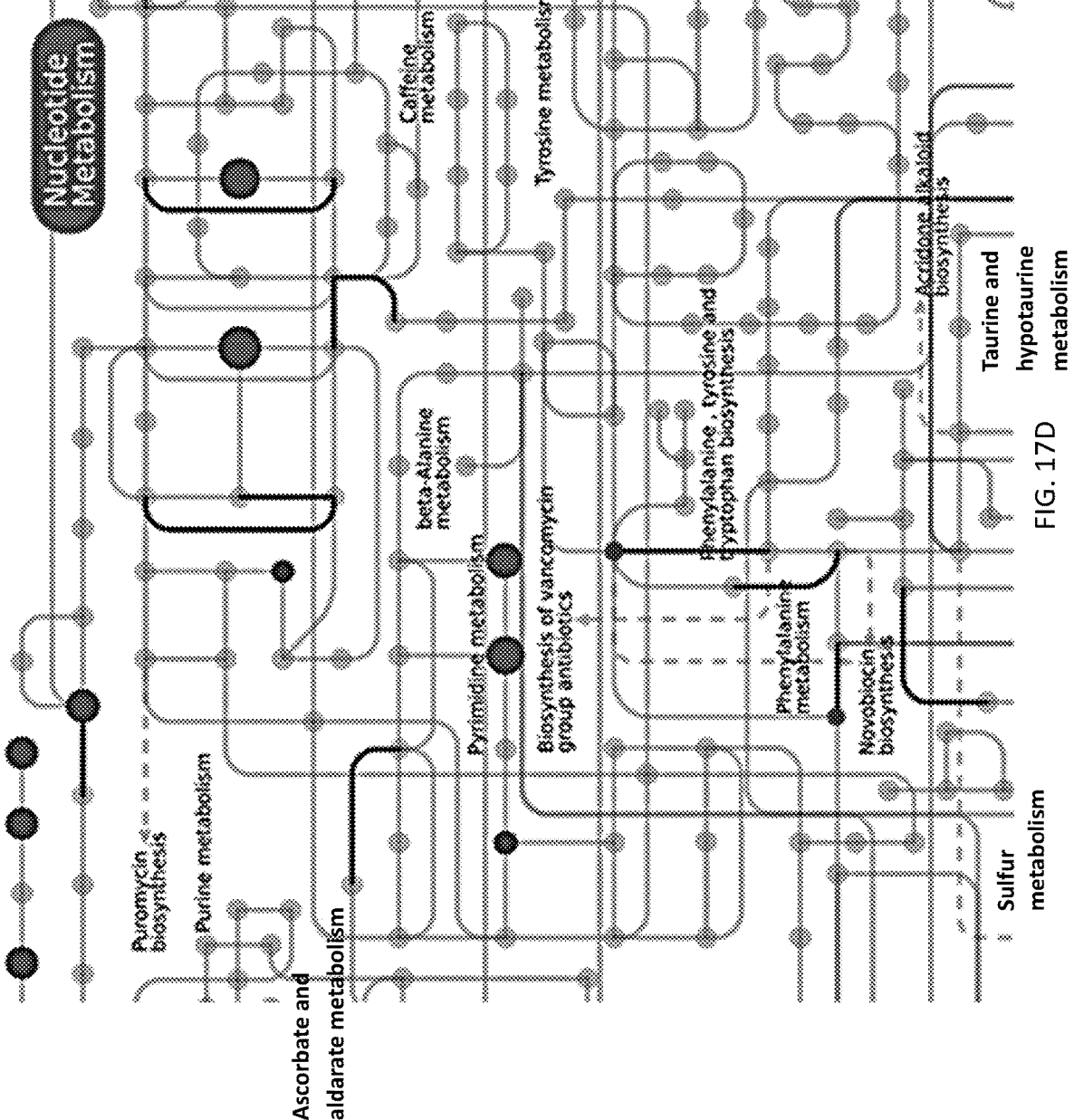
Figure 17E:
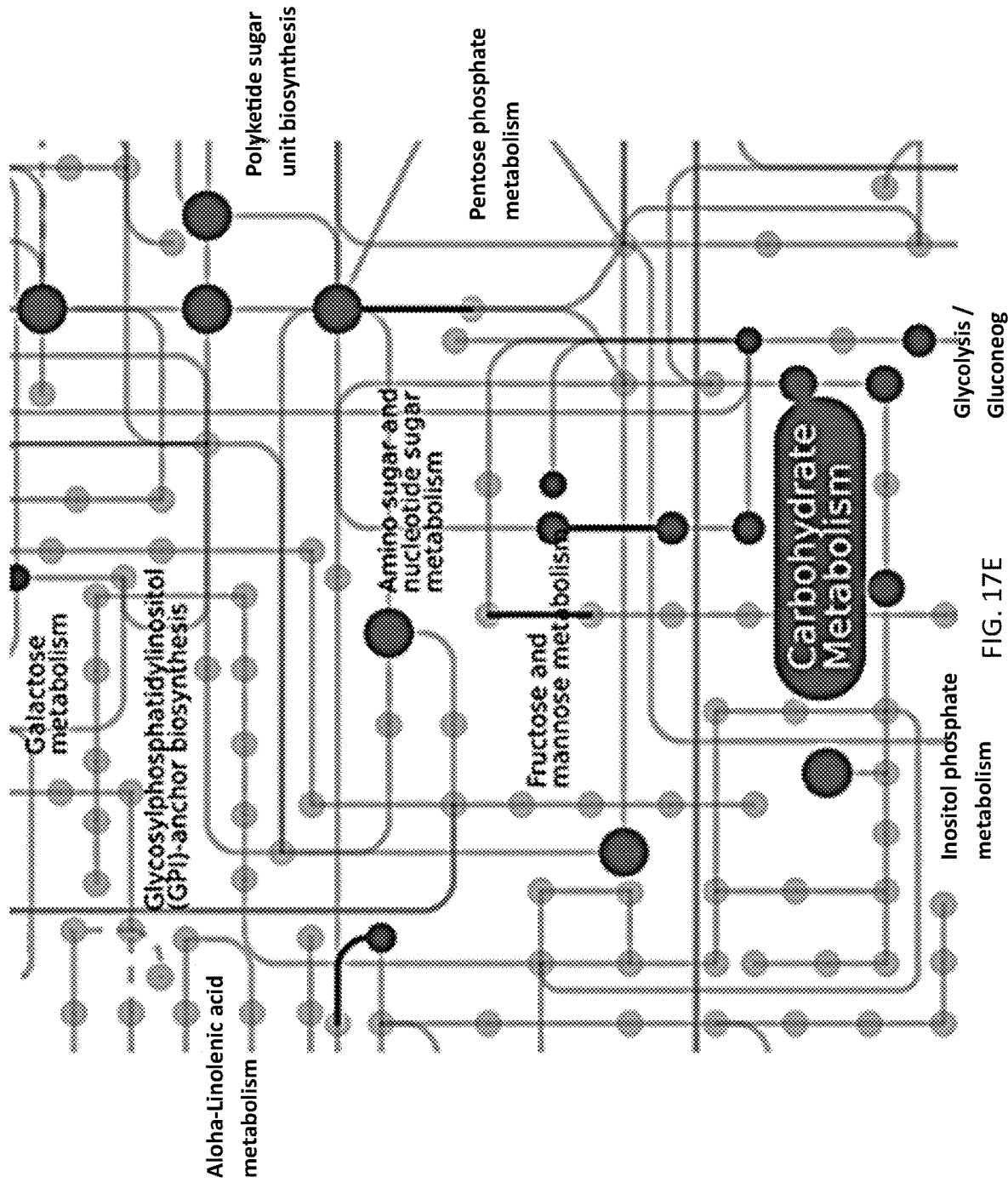
Figure 17F:
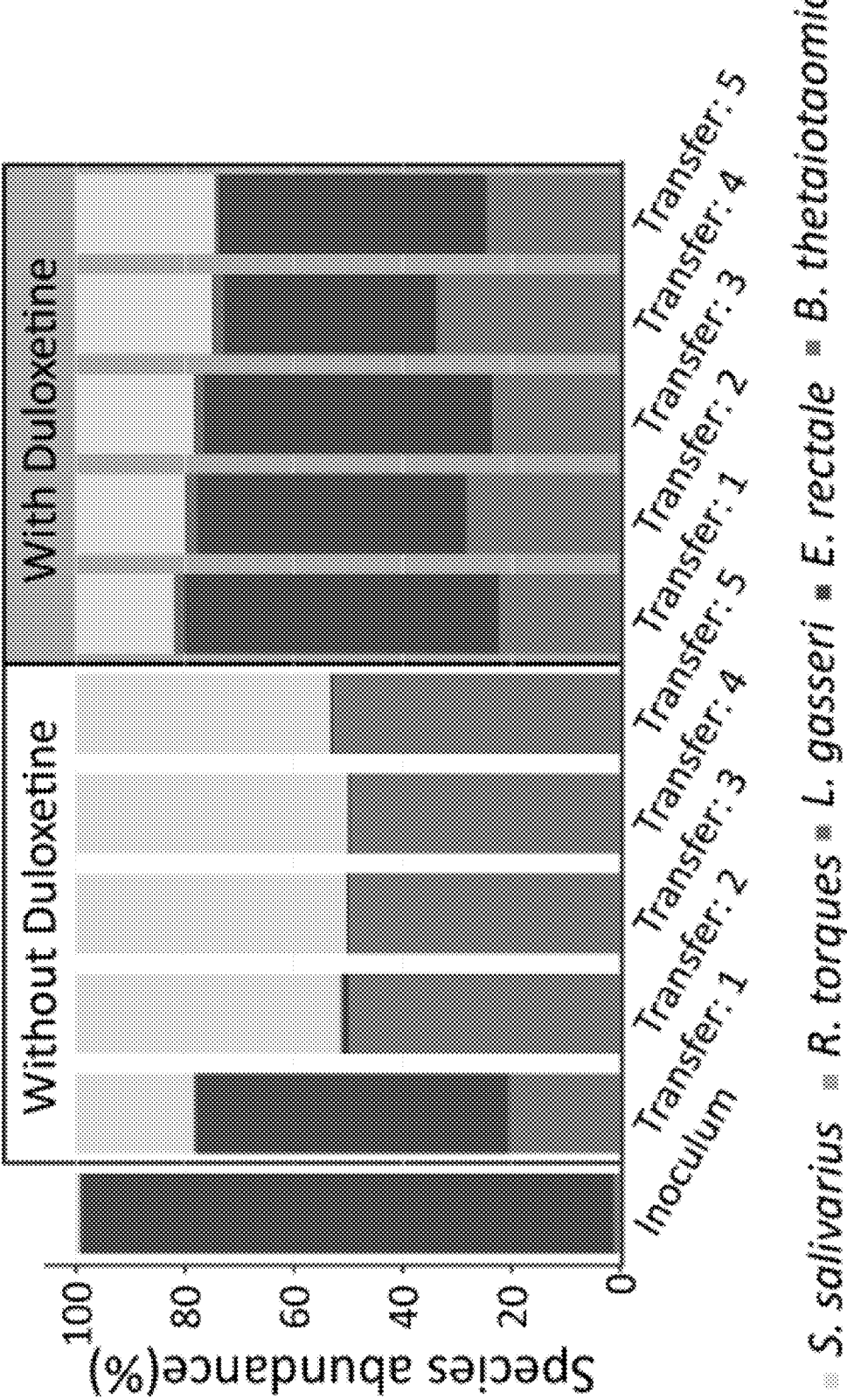
Figure 17G:
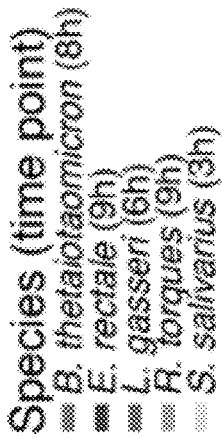

The inventors also tested the depletion-mode of bacterial drug depletion hits from the screen (FIG. 16a). Drug concentrations of extractions from the supernatant in the assay correlate reasonably well with screen concentrations (FIG. 16b). If the drug is only depleted in the supernatant, the drug is likely a bioaccumulated, whereas if the drug is also depleted in the extraction of the total fraction a biodegradation is likely. While some drugs like levamisole show a strong propensity for biodegradation, drugs like duloxetine and rosiglitazone are predominantly bioaccumulated (FIG. 16c,d). Biodegradation and bioaccumulation are not mutually exclusive even within the same strain, as e.g. for the case of montelukast or roflumilast, which were bioaccumulated and then partially degraded by several bacterial strains. For other drugs the predominant mode of depletion was either biodegradation, e.g. the antihelminthic, experimental cancer drug levamisole, or bioaccumulation, e.g. the antidepressant duloxetine and the antiasthmatic drug montelukast. Often specific bacterial drug depletion interactions were not strong, however their accumulated depletion potential across many strains could be ample reaching up to 600% of the original 50 µM dose (FIG. 16d). While drugs like sulfasalazine and levamisole are strongly degraded by many strains, those strains are not in high abundance in the gut of healthy human individuals (FIG. 16e). On the other hand, drugs like duloxetine are depleted by highly abundant bacterial strains like two *B. uniformis* strains, and thus their depletion even though moderate in the screen might have a strong clinical impact. Interestingly, only in a few interactions the same drug, which is depleted from the medium, affects also the growth of the respective bacterium (FIG. 16f). Montelukast is promoting *B. uniformis* HM715 growth and duloxetine is inhibiting growth of *C. saccharolyticum* and *E. coli* IAI1. *E. coli* IAI1 is relatively sensitive to both kinds of drug interaction, especially in comparison to *E. coli* ED1a, for which the inventors found no kind of drug interaction (FIG. 16f). The only drug neither being depleted nor affecting bacterial growth in the inventor's screen is the antiviral drug tenofovir.

Methods

Species Selection

A species core of the human gut microbiome was estimated on 364 published fecal metagenomes of pooled asymptomatic individuals from three continents and four countries (see FIG. 2). Species were defined and their abundance quantified as previously described. For inclusion in the core the inventors required a minimum prevalence of 10%, estimated by rarefying to 10,000 reads mapping to taxonomic markers, and a relative abundance of 1% or more in at least one sample. Out of 95 remaining species, the inventors selected 45 species preferably with an annotated genome. This equates to 58 of the selected strains. Additionally, the inventors selected thirteen probiotics, thirteen pathogens, three strains linked to colorectal cancer, one additional representative of the *Coprococcus, Eubacterium* and *Prevotella* genus and six metabolically unique strains.

Enzyme Coverage Estimation

The enzyme coverage of the selected species was estimated as a proportion of EC numbers mapping to the selected species to the EC numbers mapping to the core gut microbiome species. The EC number mapping was performed using KEGG database (KEGG Release 79.1, Sep. 1, 2016).

Characterization of Bacterial Growth

Bacteria were cultivated at 37° C. under anaerobic conditions in a vinyl anaerobic chamber (COY) inflated with a gas mix of approximately 15% carbon dioxide, 83% nitrogen and 2% hydrogen. Prior to the experiment, bacteria were pre-cultivated twice using one of the following media: modified Gifu anaerobic medium broth (mGAM33, HyServe), gut microbiota medium (GMM), brain heart infusion broth (BHI, Sigma-Aldrich) supplemented with 2 mg/L ß-NAD and 0.5 mg/L hemin (BHI++), MRS (de Man, Rogosa and Sharpe, Sigma-Aldrich)+0.05% (w/v) cysteine (MRS+), mGAM supplemented with 10 mM taurine and 60 mM sodium formate (mGAM++) or a 1:1 mixture of GMM and mGAM (GMM+mGAM). For long-term storage, cryovials containing freshly prepared bacterial cultures plus 7% DMSO were tightly sealed and frozen at −80° C.

A combination of dGMM and LAB served as the basic medium (dGMM+LAB). For SCFA-containing media, most abundant SCFA were added in physiological concentrations, like observed in the colon: namely acetate (30 mM), propionate (8 mM) and butyrate (4 mM), plus isovalerate (1 mM), plus a branched-chain fatty acid (BCFA) and product of leucine catabolism. For preparation of mucin-containing media, 20 g porcine gastric mucin (M1778, Sigma-Aldrich) was dissolved per L of 10 mM phosphate buffer (pH 7.5) and autoclaved for 20 min at 121° C. After standing over night at room temperature, the precipitate was removed by centrifugation, and the supernatant was added to the medium 343 to reach a final concentration of 5 g mucin per L medium. PH of all defined media was adjusted to 7.

To monitor bacterial growth, pre-cultures of individual strains were diluted in PBS to obtain an OD of 0.5 and subsequently inoculated at OD 0.01 in 100 μL of the respective media in a 96 Micro Well plate with NUNCLON Delta Surface (NUNC) sealed with a Breathe-Easy® sealing membrane (SIGMA-ALDRICH). Growth was monitored by hourly OD measurement for up to 48 h until stationary phase, using an Eon microplate spectrophotometer equipped with BioStack microplate stacker (BIOTEK) and a surrounding self-designed incubator.

Statistical Analysis

All analysis was performed using R (3.2.2) and python (2.7.6).

Growth Curves Analysis

After raw growth curves were normalized with inoculum OD to correct for medium turbidity, the inventors determined shape of the curve (to classify between growth or non-growth), maximal OD value reached (MaxOD), OD at stationary phase (StatOD), growth rate (Rate) and area under the curve (AUC) at 8, 12, 18 and 24 h. Where needed, relative growth was assessed as MaxOD on particular medium divided by MaxOD on dGMM+LAB. Furthermore, for qualitative analysis, a minimal MaxOD of 0.15 was used to determine successful growth. Quality of the data was checked by correlating measures from corresponding biological replicates: R2 (MaxOD)=0.55; R2 (StatOD)=0.35.

Species Clustering by Growth Profiles

Dissimilarity between species growth profiles were calculated using average of Euclidean distance between vectors of MaxOD values on defined media (M2-8 and M10-11), and rich media (GMM, BHI++, WCA, and mGAM). The resulting distance matrix was used for clustering with average linkage method.

Preferential Media Analysis

The inventors calculated media preference as log 2 transformation fraction of median rank of species growth on rich and defined media. Preference towards defined media was stated where preference value was bigger than 1. When the inventors required species level resolution the inventors averaged MaxOD values at species taxonomic rank.

Community Study

The inventors tested the growth of different mixtures of gut bacteria in 15 defined media. The conditions were expanded to screen growth in each media at pH 7 and at pH 5.5, both of which are within the range of the pH in the intestines. After mixing up to around 40 bacteria 1:1, the bacteria were inoculated at an overall OD of 0.01 under 30 different experimental conditions (different media, different pH), cultivated unshaken at 37° C. in an anaerobic environment, and passaged every 48 h with a ratio of ~1:50 to fresh medium. This was repeated for up to 9 passages. At the time of passaging, the inventors additionally measured the OD and pH, and took samples (bacterial cell pellets) for 16S rRNA barcode sequencing (performed by GENECORE) as well as untargeted metabolomics (performed by CELL-ZOME). The inventors established the DNA extraction protocol using the GNOME DNA Isolation Kit (MP Bio-medicals, 112010400), an additional bead beating step and the BIOMEK FXP Automated Workstation (Beckman Coulter). The library preparation for subsequent 16S rRNA barcode sequencing with miSeq was performed according to the protocol of Caporaso et al., 2010, PNAS.

Mucin Degradation Genes Analysis

List of HMM models representing carbohydrate-active enzyme families (CAZy) involved in mucin degradation was obtained from dbCAN63 on 17 Dec. 2017. HMMSCAN with default parameters was executed to check the presence of mucin genes in studied organisms (e-value<10-5 as suggested by the dbCAN).

Gap-Filling of Genome-Scale Metabolic Models

Metabolic models of the gut bacteria used in this study were obtained 378 from Magnúsdóttir et al. The inventors then used linear programming to identify minimal number of reactions missing in the model to satisfy growth phenotype (biomass yield constraint >0.1) in defined media wherein growth was experimentally observed. To further characterize the gap-filled reactions, the inventors used EC numbers provided by the TIGRFAM (release 15) protein families annotation. The inventors used HMMSCAN with default parameters to search for families present in organisms (e-value <10-5) and filtered matched protein families that had complete EC number assigned.

Correlation of Growth with In Vivo Abundance

Spearman's rank correlation coefficient was used to assess correlation between core microbiome species abundances in 364 individuals and growth in 18 tested media (M16 was excluded because it did not have enough observations). Significance was assessed by calculating Wilcoxon two-sample rank sum test against subject-wise abundance permutation background.

Genomes

Translated protein sequences of studied organisms were downloaded from NCBI on 21 Nov. 2016. For the species that did not have available genome assembly, the inventors performed whole genome sequencing on a Illumina HiSeq 2500, with paired end reads. The inventors removed sequencing adapters using cutadapt60 (1.11). The inventors assembled the resulting sequencing reads into contigs using the Spades assembler61 (3.5.0), with k-mers sizes of 21, 33, 55 and 77. The inventors excluded contigs with length below 200 base pairs. The inventors annotated the resulting contigs using Prokka (1.11). Sequencing reads and annotated contigs are available in ENA with accession number PRJEB19875.

Preparation of Screening Plates

The PRESTWICK CHEMICAL Library was purchased from Prestwick Chemical Inc. (Illkirch, France) with compounds coming dissolved in dimethyl sulfoxide (DMSO) at a concentration of 10 mM. Compounds were re-arrayed to redistribute the DMSO control wells in each plate and to minimize the total number of 96- and 384-well plates (4×384-well plates or 14×96-well plates). At the same time, drugs were diluted to a concentration of 2 mM to facilitate further aliquoting, and these plates were stored at –30° C. For each experimental batch (10 replicates in 96-well plates; 20 replicates in 384-well plates) the inventors prepared drug plates in the respective growth medium (2× for 96-well plates, 1× for 384-well plates), and stored at –30° C. until use (max 2 months). Before inoculation, plates were thawed and pre-reduced in the anaerobic chamber overnight. The BIOMEK FXP (Beckman Coulter) liquid handling system was used for all rearranging and aliquoting of the library compounds.

Inoculation (Screen of the PRESTWICK CHEMICAL Library)

Strains were grown twice overnight to make sure the inventors had a robustly and uniformly growing culture before inoculating the screening plates. For 96-well plates, the second overnight culture was diluted to fresh medium in order to reach a 2× of the aimed starting optical density (OD) at 578 nm. Next, 50 μL of this diluted inoculum was added to wells containing already 50 μl of 2× concentrated drug in the respective culture medium using a multichannel pipettor. Final drug concentration was 20 μM and each well contained 1% DMSO. For 384-well plates, the inventors inoculated with a 384 floating pin replicator VP384FP6S (V&P Scientific, Inc.), transferring 1 μl of appropriately diluted overnight culture to wells containing 50 μl of growth media, 1% DMSO and 20 μM drug. For bacterial species that reached lower OD in overnight cultures the inventors transferred twice 1 μl of appropriately adjusted OD culture. Both for 96- and 384-well plates, the starting OD was 0.01 or 0.05 depending on the growth preference of the species.

Screening Conditions During the Screen of the PRESTWICK CHEMICAL Library

After inoculation, plates were sealed with breathable membranes (Breathe-Easy®) to prevent evaporation and cross-contamination between wells, and incubated at 37° C. without shaking. Growth curves were acquired by tracking OD at 578 nm with a microplate spectrophotometer (EON, Biotek). Measurements were taken every 1-3 hrs after 30-60 seconds of linear shaking, initially manually but later automatically using a microplate stacker (Biostack 4, Biotek), fitted inside a custom-made incubator (EMBL Mechanical Workshop). The inventors collected measurements for 16-24 hrs. Each strain was screened in at least three biological replicates.

Normalization of Growth Curves and Quantification of Growth

Growth curves were analyzed by plate. All growth curves within a plate were truncated at the time of transition from exponential to stationary. The end of exponential phase was determined automatically by finding the peak OD (using the median across all compounds and control wells, and accounting for a small increase during stationary phase) and verified by inspection. Using this timepoint allowed the inventors to capture effects of drugs on lag phase, growth rate and stationary phase plateau. Timepoints with sudden spikes in OD (e.g. caused by condensation) were removed, and a growth curve was discarded completely if there were too many missing timepoints. Similarly, growth curves were discarded if the OD fell too far outside the normal range (e.g. caused by compounds that are strongly absorbing). Three compounds had to be completely excluded from the analysis, as they mostly caused aberrant growth curves: Chicago sky blue 6B, mitoxantrone, and verteporfin. Growth curves were processed by plate to set the median OD at the start and end timepoints to 0 and 1, respectively. Then, the inventors determined reference compounds across all replicates that did not reduce growth significantly for most drugs: that were compounds for which measurements were available for >95% of replicates, and for which final OD was >0.5 for more than 122 out of 132 replicates. The inventors used these reference compounds as representatives of uninhibited growth. Since wells containing reference compounds outnumbered control wells within a plate, the inventors used control wells only later to verify the p691 value calculation. After determining reference compounds, the inventors rescaled growth curves such that the median growth of reference compounds at the end point is 1.

While growth curves in control wells and most wells with reference compounds followed the expected logistic growth pattern, a variety of deviations were observed for drugs that influenced growth. To quantify growth without relying on assumptions about the shape of the growth curve, the inventors calculated the area under the curve (AUC) using the trapezoidal rule. While the inventors set the median starting OD to 0, the OD of individual wells deviated from this. The inventors used two different methods to correct for this and determine the baseline for each growth curve. First, a constant shift was assumed, subtracting the same shift to all timepoints of the growth curve such that the minimum is zero. Second, an initial perturbation was assumed that affects initial timepoints more than later timepoints (e.g. condensation). To correct this, the inventors first subtracted a constant shift as above, and then rescaled the curve such that a timepoint with an uncorrected OD of 1 also has an OD of 1 after correction. AUCs were calculated for both scenarios, rescaled such that the AUC of reference compounds is 1, and then for each compound the baseline correction that yielded an AUC closest to 1 (i.e. normal growth) was selected. AUCs are highly correlated to final ODs, with a Pearson correlation of 0.95 across all compounds and replicates. Nonetheless, the inventors preferred to use AUCs to decrease the influence of the final timepoint, which will contain more noise than a measurement based on all time-points.

Identification of Drugs with Anticommensal Activity

The inventors detected hits from normalized AUC measurements using a statistical method that controls for multiple hypothesis testing and varying data quality. The inventors fitted heavy-tailed distributions (scaled Student's t-distribution) to the wells containing reference compounds for each replicate and, separately, to each individual plate. These distributions captured the range of AUCs expected for compounds that did not reduce growth, and represented the null hypothesis that a given drug did not cause a growth defect in the given replicate or plate. The inventors calculated one-sided p-values from the cumulative distribution function of the fitted distribution. Within a replicate, each compound was associated with two p-values: one from the plate on which it was measured, and one for the whole replicate. Of those two, the highest p-value was chosen (conservative estimate) to control for plates with little or high noise, and varying levels of noise within the same replicate. The resulting p-values were well-calibrated (i.e. the distribution of p-values is close to uniform with the exception of a peak at low p-values) and captured the distribution of controls, which were not used for fitting the distribution and kept for validation. The inventors then combined p-values for a given drug and strain across replicates using Fisher's method. Lastly, the inventors calculated the False Discovery Rate (FDR) using the Benjamini-Hochberg method over the complete matrix of p-values (1197 compounds by 40 strains). After inspecting representative AUCs for compound—strain pairs at different FDR levels, the inventors chose a conservative FDR cut-off of 0.01.

Drug Indications, Dose, and Administration

The inventors annotated drugs by their primary target organism on the basis of their WHO Anatomical Therapeutic Chemical (ATC) classification, or, if there were uncertainties, based on manual annotation. Compounds were classified as: antibacterial drugs (antibiotics, antiseptics), anti-infective drugs (acting against protozoa, fungi, parasites or viruses), human-targeted drugs (i.e. drugs whose mechanism of action affects human cells), veterinary drugs (used exclusively in animals), and finally non-drugs (which can be drug metabolites, drugs used only in research, or endogenous substances). If a human-use drug belonged to several classes, the drug class was picked according to this order of priority (from high to low): antibacterial, anti-infective, and human-targeted drug. This ensured that drugs used also as antibacterials were not classified in other two categories.

Drugs from the Prestwick Chemical Library were matched against STITCH 4 identifiers using CART. Identifiers that could not be mapped were annotated manually. Information about drug indications, dose and administration was extracted from the ATC classification system and Defined Daily Dose (DDD) database. Dose and administration data were also extracted from the Drugs@FDA resource. Doses that were given in grams were converted to mol using the molecular weight stated in the Prestwick library information files. When the dose guidelines mentioned salt forms, the inventors manually substituted the molecular weight. Dose data from Drugs@FDA stated the amount of drug for a single dose (e.g. a single tablet).

Analyzing the intersection between Drugs@FDA and DDD, the inventors found that the median ratio between the single and daily doses is two. To combine 758 the two datasets the inventors therefore estimated the single dose as half of the daily dose.

In general, it is difficult to estimate intestinal drug concentrations, since those depend on the dose, the speed of dissolution, uptake and metabolization by human cells and by bacteria, binding to proteins, and excretion mechanisms into the gut. To estimate gut concentrations of drugs based on their dose, the inventors relied on the only in situ study known to us. When 40 mg (57 μmol) of posaconazole are delivered to the stomach in either an acidic or neutral solution, the maximum concentration in the duodenum reaches 26.3±10.3 and 13.6±5.8 μM, respectively. The ratio between the dose and the duodenal concentration corresponds to a volume estimate of roughly three liters.

MIC Determination/Screen Validation

To validate the inventors' screen, the inventors selected 22 drugs including human-targeted drugs (16), anitprotozoals (3), one antiparasitc, one antiviral and one 'no-drug' compound. The human targeted drugs spanned 5 therapeutic classes (ATC codes A, G, L, M, N). The inventors' selection comprised mostly drugs with broad-spectrum activity in the inventors' screen (19 drug hits >10 strains). This bias was for ensuring that the inventors can also evaluate false positives. The inventors chose 15 strains to test MICs, spanning different phyla (5) and including both sensitive (E. rectale, R. intestinalis) and resistant species (E. coli ED1a). Compounds of interest were purchased from independent sources and dissolved at 100× starting concentration in DMSO. 2-fold serial dilutions were prepared in 96-well U-bottom plates (same as screen). Each row contained a different drug at eleven 2-fold dilutions and a control DMSO well in the middle of the row (in total 8 drugs per plate). These master plates were diluted to 2× assay concentration and 2% DMSO in mGAM medium (50 μl) and stored at −30° C. (<1 month). For the assay, plates were pre-reduced overnight in the anaerobic chamber, and mixed with equal volume (50 μl) of appropriately diluted overnight culture (prepared as described for screening section) to reach a starting OD578 of 0.01 and a DMSO concentration of 1% across all wells. OD578 was measured hourly for 24 hrs after 1 min of shaking.

Growth curves were converted to AUCs as described above, using in-plate control wells (no drug) to define normal growth. For each concentration, the inventors calculated the median across the two replicates. The inventors further enforced monotonicity to conservatively remove noise effects: if the AUC decreased for lower concentrations, it was set to the highest AUC measured at higher concentrations. The MIC was defined as the lowest concentration for which a median AUC of 0.75 was measured.

Analysis of Side Effects

Side effects (SEs) of drugs were extracted from the SIDER 4.1 database using the mapping between Prestwick compounds and STITCH 4 identifiers described above. In SIDER, SEs are encoded using the MedDRA terminology, which contains lower-level terms and preferred terms. Of these, the inventors used the preferred terms, which are more general. The inventors excluded rare SEs that occurred for less than five drugs from the analysis. Drugs with less than seven associated SEs were discarded. In a first pass, the inventors identified SEs associated with antibiotics in SIDER, by calculating for each SEs its enrichment for systemic antibiotics (ATC code J01) versus all other drugs using Fisher's exact test (p-value cut-off: 0.05, correcting for multiple hypothesis testing using the Benjamini-Hochberg method). Antibiotics are typically administered in relatively high doses, and some of the enriched SEs might therefore be caused by a dose-dependent effect (e.g. kidney toxicity). The inventors therefore used an ANOVA (Type II) to test if the presence of SEs for a drug is more strongly associated with it being an antibiotic or with its (log-transformed) dose. SEs that were more strongly associated with the dose were excluded from the list of antibiotics-related SEs.

Data on the incidence rates of SEs in patients was also extracted from SIDER 4.1. As different clinical trials can report different incidence rates, the inventors computed the median incidence rate per drug-SE pair. As SIDER also contains data on the incidence of SE upon placebo treatment, the inventors were able to ensure the absence of systematic biases.

Experimental Validation of Side Effect-Based Predictions

Compounds of interest were purchased from independent sources and if possible, dissolved at 5 mM concentration in mGAM. Lower concentrations were used when solubility limit was reached. Solutions were sterile filtered, and three 4-fold serial dilutions were arranged in 96 well plates, aiming at covering a broad range of drug concentrations. Inoculation and growth curve acquisition was performed as described for the MIC determination experiments.

Conjugation of the TransBac Overexpression Plasmid Library into E. coli ΔtoIC

The TransBac library, a new E. coli overexpression library based on a single-copy vector (H. Dose & H. Mori— unpublished resource) was conjugated in the BW25113 ΔtoIC::Kan strain. The receiver strain (BW25113 ΔtoIC:: kan) was grown to stationary phase in LB medium, diluted to an OD of 1, and 200 µl were spread on a LB plate supplemented with 0.3 mM diaminopimelic acid (DAP). Plates were dried for 1 hour at 37° C. and then a 1536 colony array of the library carried within a donor strain (BW38029 Hfr (CIP8 oriT::cat) dap-75) was pinned on top of the lawn. Conjugation was carried out at 37° C. for ~6 hours, and the first selection was done by pinning on LB plates supplemented with tetracycline only (10 µg/ml) and growing overnight. Two more rounds of selection followed on LB plates containing tetracycline (10 µg/ml) and kanamycin (30 µg/ml) to ensure killing of parental strains and select only for toIC mutants carrying the different plasmids.

Chemical Genomics Screen

The screen was carried out under aerobic conditions on solid LB Lennox medium (DIFEQ), supplemented with 30 µg/ml kanamycin, 10 µg/ml tetracycline, the appropriate drug, and 0 or 100 µM IPTG. Drugs were used at the following sub-inhibitory concentrations for the toIC mutant: diacerein 20 µM, ethopropazine hydrochloride 160 µM, tamoxifen citrate 20 µM, niclosamide 1.25 µM, thioridazine hydrochloride 40 µM, methotrexate 320 µM, or for the wildtype: metformin 100 mM. The 1536 colony array of BW25113 ΔtoIC::kan mutant carrying the TransBac collection was pinned on the drug-containing plates, and plates were incubated for 16-38 hours at 37° C. In the case of metformin the inventors used the version of the TRANS-BAC library, in which each plasmid complements its corresponding barcoded single-gene deletion mutant, since the inventors did not need to use the ΔtoIC background for sensitizing the cell. Growth of this library was determined at 0 and 100 mM metformin (both in the presence of 0, 50 and 100 Mm IPTG). All plates were imaged using an 18 mega-pixel Canon Rebel T3i (Canon inc USA) and images were processed using the Iris software.

Liquid Chromatography

All liquid chromatography methods are run on a Waters Acquity UPLC H-Class instrument with a PDA detector and a quaternary solvent system. All established methods are 5 minutes long, have a flow rate of 0.5 ml/min and run on a CSH C18 column (Waters, Part number 186005297) in reverse mode. The column is heated to 40° C. and samples are kept at 6° C. All methods use 50% acetonitrile (Biosolve, ULC grade) for washing buffer, and 50% methanol (Bio-solve, ULC grade) for purging buffer. As organic mobile phase acetonitrile was used. The assay was optimized using only two buffers besides water as hydrophilic mobile phase: 5 mM formic acid (Biosolve, ULC grade) of pH 3.2 and 5 mM ammonium formate (Ammonium hydroxide, ACS grade, Sigma) with pH adjusted to 8.3 using the formic acid buffer. Table 10 lists the five different chromatographic methods established for the different drugs. The specific chromatographic method and detection wavelength used for identification of each drug compound can be found in Table 11.

Depletion-Mode Assay

Bacteria from second passage culture are inoculated with an OD578 of 0.01 in 1 mL GMM containing 50 µM drug of interest in 2 mL eppendorf tubes and incubated for 48 h while shaking. After finishing growth, the cultures were removed from the anaerobic chamber. 800 µl of each sample was transferred to a new eppendorf tube, while the remaining 200 µl were directly extracted by adding 600 µl ice-cold acetonitrile:methanol solution and incubated for 15 min at 4° C. For supernatant extraction, the transferred culture was centrifuged for 5 min at 14.000 rpm to pellet the bacteria, and 200 µl of the bacteria-free supernatant was extracted in a new eppendorf tube respectively. After the 15 min 4° C. incubation period, all samples were centrifuged for 10 min, 14.000 rpm at 4° C. and 700 µl of the supernatant was transferred to a new eppendorf tube. Samples were dried for 5-7 h at 30° C. in a speedvac (Eppendorf Vacuum Concentrator Plus, V-AL mode) and stored at −20° C. until used for UPLC measurement. Samples were reconstituted in 116 µl 20% acetonitrile containing 250 µM caffeine. All interactions and controls were tested in triplicates.

Bacteria-Interaction Screen

For all drugs, a fixed concentration of 50 UM was used, which in most cases approximates the concentration of one pill (0.02-3 mmol) diluted in the volume of the gut (approx. 2.5 L). One bacteria-free control per plate and drug, but triplicates for each bacteria-drug interaction was screened. The screen was carried out under anaerobic conditions in 96-well plates (NUNCLON Delta Surface 163320, NUNC) with 150 µl GMM as the growth medium sealed with a Breathe-Easy® sealing membrane (Z380059, SIGMA-AL-DRICH). Plates containing 100 µl of the medium and 75 µM of the drug were prepared beforehand, stored at −20° C. and used as needed. Frozen plates were introduced into the anaerobic chamber the evening before inoculation. Wells were inoculated with 50 µl of a second passage culture with an end OD578 of 0.01. Growth was monitored with measurements of the optical density at 578 nm using an Eon Microplate Spectrophotometer (BIOTEK) approximately every 2 h for the first 10 h, then approximately every 6 h. After 48 h, plates were removed from the anaerobic chamber and the bacteria spinned down (4000 rpm, 10 min). Then, 100 µl of the supernatant was extracted in 300 µl ice cold acetonitrile:methanol (Biosolve, ULC grade) in 500 µl poly-propylene plates (Corning Costar 3957) to remove compounds interfering with liquid chromatography. Plates were closed with a lid (Corning, storage mat 3080) and after shaking and 15 minutes incubation at 4° C., samples were centrifuged at 4000 rpm for 10 min at 4° C. and 300 µl of the supernatant were transferred to a new plate (Corning Costar 3362). All liquid handling outside of anaerobic chamber was done using a liquid handling robot (FXp, BIOMEK). Sample plates were then left overnight in a chemical hood to evaporate the organic phase, before being stored at −20° C. For estimating the drug concentration in the samples with the UPLC, samples were reconstituted in 50 µl 20% acetonitrile solution containing 250 µM caffeine (SIGMA) as an internal standard. The bacteria-drug interaction screen was conducted with two biological replicates.

Data Analysis

The inventors used colony size to measure the fitness of the mutants on the plate. For standardization of colony sizes, the inventors subtracted the median colony size and then divided by a robust estimate of the standard deviation (removing outliers below the 1st and above the 99th percentile). The inventors found edge effects affecting up to five rows and columns around the perimeter of the plate. The inventors therefore first standardized colony sizes across the whole plate using only colony sizes from the inner part of the plate as reference. To remove the edge effects, the inventors subtracted from each column its median colony size, and then from each row its median colony size. Finally, the inventors standardized the adjusted colony sizes using the whole plate as reference. The distribution of adjusted colony sizes was right-skewed (i.e. more outlier colonies with larger size), suggesting a log-normal distribution. At the same time, the presence of outliers suggested that a logarithmic equivalent of the Student's t-distribution with variable degree of freedom would be more suitable. The inventors fitted such a distribution for each plate and calculated p-values for both tails of the distribution. This approach assumes that the overexpression of most genes does not affect growth in response to drug treatment. p-values were combined using Fisher's method across replicates and IPTG concentrations (since the inventors noticed that different IPTG concentrations resulted to largely the same results—i.e. plasmids are leaky). The inventors corrected for multiple hypothesis testing for each drug individually using the Benjamini-Hochberg method. Analysis of common resistance mechanisms: To determine a relationship between the number of human-targeted drugs (h) and the number of antibacterial drugs (a) that affect each strain, the inventors determined the odds ratio (OR):

$$OR = \frac{\dfrac{h}{H - h}}{\dfrac{a}{A - a}}$$

Where H=204 and A=122 are the numbers of human-targeted and antibacterial drugs that show activity, respectively. The inventors computed the nonlinear least-squares estimate for OR based on the following equation:

$$\frac{h}{H - h} = OR \cdot \frac{a}{A - a}$$

Table 1 shows selected gut bacteria of the in-vitro model of the human gut microbiome.

| Designation in screen | Strain | TaxID | Metabolic model | Assembly | Pre-inoculation media |
|---|---|---|---|---|---|
| A. muciniphila | Akkermansia muciniphila Muc, DSM 22959, ATCC BAA-835, CIP 107961 | 349741 | Akkermansia_muciniphila_ATCC_BAA_835 | GCA_000020225.1_ASM2022v1 | mGAM |
| A. putredinis | Alistipes putredinis DSM 17216, CCUG 45780, CIP 104286, ATCC 29800, Carlier 10203, VPI 3293 | 445970 | Alistipes_putredinis_DSM_17216 | GCA_000154465.1_ASM15446v1 | GMM + mGAM |
| A. shahii | Alistipes shahii WAL 8301, DSM 19121, ATCC BAA-1179, CCUG 48947 | 717959 | Alistipes_shahii_WAL_8301 | GCA_000210575.1_ASM21057v1 | GMM + mGAM |
| B. caccae | Bacteroides caccae DSM 19024, ATCC 43185, CCUG 38735, CIP 104201, JCM 9498, NCTC 13051, VPI 3452A | 411901 | Bacteroides_caccae_ATCC_43185 | GCA_000169015.1_ASM16901v1 | mGAM |
| B. clarus | Bacteroides clarus A 20, YIT 12056, DSM 22519, JCM 16067 | 762984 | Bacteroides_clarus_YIT_12056 | GCA_000195615.1_ASM19561v1 | mGAM |
| B. coprocola | Bacteroides coprocola M16, DSM 17136, JCM 12979 | 470145 | Bacteroides_coprocola_M16_DSM_17136 | GCA_000154845.1_ASM15484v1 | mGAM |
| B. dorei | Bacteroides dorei 175, DSM 17855, JCM 13471 | 483217 | Bacteroides_dorei_DSM_17855 | GCA_000156075.1_ASM15607v1 | mGAM |
| B. eggerthii | Bacteroides eggerthii DSM 20697, ATCC 27754, NCTC 11155 | 483216 | Bacteroides_eggerthii_DSM_20697 | GCA_000155815.1_ASM15581v1 | mGAM |
| B. fragilis | Bacteroides fragilis EN-2, VPI 2553, DSM 2151, ATCC 25285, JCM 11019, NCTC 9343 | 272559 | Bacteroides_fragilis_NCTC_9343 | GCA_000025985.1_ASM2598v1 | mGAM |
| B. ovatus | Bacteroides ovatus ATCC 8483, NCTC 11153 | 411476 | Bacteroides_ovatus_ATCC_8483 | GCA_000154125.1_ASM15412v1 | mGAM |
| B. fragilis HM-20 | Bacteroides fragilis 3_1_12, HM-20 | 457424 | Bacteroides_fragilis_3_1_12 | GCA_000157015.1_ASM15701v1 | mGAM |
| B. thetaiotaomicron | Bacteroides thetaiotaomicron E50, VPI 5482, DSM 2079, ATCC 29148, NCTC 10582 | 226186 | Bacteroides_thetaiotaomicron_VPI_5482 | GCA_000011065.1 ASM1106v1 | mGAM |
| B. uniformis | Bacteroides uniformis VPI 0061, DSM 6597, ATCC 8492 | 411479 | Bacteroides_uniformis_ATCC_8492 | GCA_000154205.1_ASM15420v1 | mGAM |

-continued

| Designation in screen | Strain | TaxID | Metabolic model | Assembly | Pre-inoculation media |
|---|---|---|---|---|---|
| *B. vulgatus* | *Bacteroides vulgatus* DSM 1447, ATCC 8482 | 435590 | *Bacteroides*_vulgatus_ATCC_8482 | GCA_000012825.1_ ASM1282v1 | mGAM |
| *B. adolescentis* | *Bifidobacterium adolescentis* E194a (Variant a), DSM 20083, ATCC 15703, CCUG 18363, NCTC 11814 | 367928 | *Bifidobacterium_adolescentis*_ATCC_15703 | GCA_000010425.1_ ASM1042v1 | mGAM |
| *B. longum* subsp. *infantis* | *Bifidobacterium longum* subsp. *infantis* S12, DSM 20088, ATCC 15697, NCTC 11817 | 391904 | Bifidobacterium_*longum*_*infantis* ATCC_15697 | GCA_000269965.1_ ASM26996v1 | GMM |
| *B. wadsworthia* | *Bilophila wadsworthia* WAL 7959 [Lab 88-130H], ATCC 49260 | 1408428 | no | GCA_000701705.1_ ASM70170v1 | mGAM++ |
| *B. hansenii* | *Blautia hansenii* VPI C7-24, DSM 20583, ATCC 27752 | 537007 | *Blautia_hansenii*_VPI_C7_24_DSM_20583 | GCA_000156675.1_ ASM15667v1 | mGAM |
| *B. obeum* | *Blautia obeum* VPI B3-21, DSM 25238, ATCC 29174, KCTC 15206 | 411459 | *Blautia_obeum*_ATCC_29174 | GCA_000153905.1_ ASM15390v1 | mGAM |
| *B. crossotus* | *Butyrivibrio crossotus* VPI T9-40A, DSM 2876, ATCC 29175 | 511680 | *Butyrivibrio_crossotus*_DSM_2876 | GCA_000156015.1_ ASM15601v1 | mGAM |
| *C. bolteae* | *Clostridium bolteae* WAL 16351, DSM 15670, ATCC BAA-613, CCUG 46953 | 411902 | *Clostridium_bolteae*_ATCC_BAA_613 | GCA_000154365.1_ ASM15436v1 | GMM |
| *C. leptum* | *Clostridium leptum* VPI T7-24-1, DSM 753, ATCC 29065 | 428125 | *Clostridium_leptum*_DSM_753 | GCA_000154345.1_ ASM15434v1 | GMM |
| *C. ramosum* | *Clostridium ramosum* 113-I, VPI 0427, DSM 1402, ATCC 25582, NCIB 10673 | 445974 | *Clostridium_ramosum*_VPI_0427_DSM_1402 | GCA_000154485.1_ ASM15448v1 | GMM |
| *C. aerofaciens* | *Collinsella aerofaciens* VPI 1003, DSM 3979, ATCC 25986 | 411903 | *Collinsella_aerofaciens*_ATCC_25986 | GCA_000169035.1_ ASM16903v1 | mGAM |
| *C. comes* | *Coprococcus comes* VPI CI-38, ATCC 27758 | 470146 | *Coprococcus_comes*_ATCC_27758 | GCA_000155875.1_ ASM15587v1 | mGAM |
| *D. piger* | *Desulfovibrio piger* VPI 11112, VPI C3-23, DSM 749, ATCC 29098, JCM 12224 | 411464 | *Desulfovibrio_piger*_ATCC_29098 | GCA_000156375.1_ ASM15637v1 | BHI++ |
| *D. formicigenerans* | *Dorea formicigenerans* VPI C8-13, DSM 3992, ATCC 27755, JCM 10342 | 411461 | *Dorea_formicigenerans*_ATCC_27755 | GCA_000169235.1_ ASM16923v1 | mGAM |
| *E. coli* ED1a | *Escherichia coli* ED1a | 585397 | iECED1_1282 | GCA_000026305.1_ ASM2630v1 | mGAM |
| *E. coli* IAI1 | *Escherichia coli* IAI1 | 585034 | iECIAI1_1343 | GCA_000026265.1_ ASM2626v1 | mGAM |
| *E. eligens* | *Eubacterium eligens* C15-B4, DSM 3376, ATCC 27750 | 515620 | *Eubacterium_eligens*_ATCC_27750 | GCA_000146185.1_ ASM14618v1 | mGAM |
| *E. rectale* | *Eubacterium rectale* A1-86, DSM 17629, NCIMB 14373 | 657318 | no | GCA_000209935.1_ ASM20993v1 | mGAM |
| *E. siraeum* | *Eubacterium siraeum* VPI T9-50-2, DSM 15702, ATCC 29066, DSM 3996 | 428128 | *Eubacterium_siraeum*_DSM_15702 | GCA_000154325.1_ ASM15432v1 | mGAM |
| *H. parainfluenzae* | *Haemophilus parainfluenzae* DSM 8978, ATCC 33392, NCTC 7857 | 888828 | no | GCA_000191405.1_ ASM19140v1 | BHI++ |
| *O. splanchnicus* | *Odoribacter splanchnicus* 1651/6, DSM 20712, ATCC 29572, CCUG 21054, CIP 104287, LMG 8202, NCTC 10825 | 709991 | *Odoribacter_splanchnicus*_1651_6_DSM_20712 | GCA_000190535.1_ ASM19053v1 | mGAM |
| *P. distasonis* | *Parabacteroides distasonis* DSM 20701, ATCC 8503, CCUG 4941, JCM 5825, NCTC 11152 | 435591 | *Parabacteroides*_distasonis_ATCC_8503 | GCA_000012845.1_ ASM1284v1 | mGAM |
| *P. merdae* | *Parabacteroides merdae* VPI T4-1, DSM 19495, ATCC 43184, CCUG 38734, CIP 104202, JCM 9497 | 411477 | *Parabacteroides_merdae*_ATCC_43184 | GCA_000154105.1_ ASM15410v1 | mGAM |
| *P. copri* | *Prevotella copri* CB7, DSM 18205, JCM 13464 | 537011 | Prevotella_*copri*_CB7_DSM_18205 | GCA_000157935.1_ ASM15793v1 | mGAM |
| *R. hominis* | *Roseburia hominis* A2-183, DSM 16839, CIP 109406, JCM 17582, NCIMB 14029 | 585394 | *Roseburia_hominis*_A2_183 | GCA_000225345.1_ ASM22534v1 | GMM + mGAM |
| *R. intestinalis* | *Roseburia intestinalis* L1-82, DSM 14610, CIP 107878, JCM 17583, NCIMB 13810 | 536231 | *Roseburia_intestinalis*_L1_82 | GCA_000156535.1_ ASM15653v1 | mGAM |
| *R. gnavus* | *Ruminococcus gnavus* VPI C7-9, ATCC 29149 | 411470 | *Ruminococcus_gnavus*_ATCC_29149 | GCA_000169475.1_ ASM16947v1 | GMM |

-continued

| Designation in screen | Strain | TaxID | Metabolic model | Assembly | Pre-inoculation media |
|---|---|---|---|---|---|
| R. torques | Ruminococcus torques VPI B2-51, ATCC 27756 | 411460 | Ruminococcus_torques_ATCC_27756 | GCA_000153925.1_ASM15392v1 | GMM |
| S. parasanguinis | Streptococcus parasanguinis DSM 6778, ATCC 15912, CIP 13046, SS 898 | 760570 | no | GCA_000164675.2_ASM16467v2 | mGAM |
| S. salivarius | Streptococcus salivarius 275, DSM 20560, ATCC 7073, NCTC 8618 | 1304 | no | NT5038 | mGAM |
| V. parvula | Veillonella parvula Te3, DSM 2008, ATCC 10790, JCM 12972, NCTC 11810 | 479436 | Veillonella_parvula_Te3_DSM_2008 | GCA_000024945.1_ASM2494v1 | BHI++ |

Table 2 shows media composition of dGMM and LAB medium, dGMM and LAB medium comprising a reduced amount of minerals and vitamins, dGMM and LAB medium excluding short chain fatty acids (SOFA), dGMM and LAB medium comprising monosaccharides as only carbohydrate source, dGMM and LAB medium comprising Mucin, dGMM and LAB medium comprising Mucin as only carbohydrate source, dGMM and LAB medium comprising containing only 10% amino acids and dGMM and LAB medium excluding aromatic amino acids.

|  |  | Media name | | | | | | | | | |
|---|---|---|---|---|---|---|---|---|---|---|---|
|  |  | dGMM | LAB | dGMM + LAB | dGMM + LAB low M/V | dGMM + LAB exclude SCFA | dGMM + LAB + only mono-sacharides | dGMM + LAB + Mucin | dGMM + LAB + only Mucin | dGMM + LAB + 10% amino-acids | dGMM + LAB exclude aromatic amino acids |
| Sugar | D-glucose | 0.4 g | 15 g | 5 g | 5 g | 5 g | 5 g | 5 g |  | 5 g | 5 g |
|  | Fructose | 1 g |  | 1 g | 1 g | 1 g | 1 g | 1 g |  | 1 g | 1 g |
|  | Cellobiose | 1 g |  | 1 g | 1 g | 1 g |  | 1 g |  | 1 g | 1 g |
|  | Maltose | 1 g |  | 1 g | 1 g | 1 g |  | 1 g |  | 1 g | 1 g |
|  | Lactose |  |  | 1 g | 1 g | 1 g |  | 1 g |  | 1 g | 1 g |
| Others | Resazurin | 1 mg |  | 1 mg | 1 mg | 1 mg | 1 mg | 1 mg | 1 mg | 1 mg | 1 mg |
|  | NAD (N1511) |  |  | 2 mg | 2 mg | 2 mg | 2 mg | 2 mg | 2 mg | 2 mg | 2 mg |
|  | Hemin |  |  | 0.5 mg | 0.5 mg | 0.5 mg | 0.5 mg | 0.5 mg | 0.5 mg | 0.5 mg | 0.5 mg |
|  | Mucin |  |  |  |  |  |  | 5 g | 5 g |  |  |
|  | KCl |  |  |  |  |  |  | 50 mg | 50 mg |  |  |
|  | Hematin | 1.2 mg |  | 1.2 mg | 1.2 mg | 1.2 mg | 1.2 mg | 1.2 mg | 1.2 mg | 1.2 mg | 1.2 mg |
| Amino acids | I-Histidine | 31 mg | 0.17 g | 0.171 g | 0.171 g | 0.171 g | 0.171 g | 0.171 g | 0.171 g | 31 mg | 0.171 g |
|  | I-Isoleucine |  | 0.24 g | 0.24 g | 0.24 g | 0.24 g | 0.24 g | 0.24 g | 0.24 g | 24 mg | 0.24 g |
|  | I-Leucine |  | 1 g | 1 g | 1 g | 1 g | 1 g | 1 g | 1 g | 0.1 g | 1 g |
|  | I-Methionine |  | 0.125 g | 0.125 g | 0.125 g | 0.125 g | 0.125 g | 0.125 g | 0.125 g | 12.5 mg | 0.125 g |
|  | I-Valine |  | 0.7 g | 0.7 g | 0.7 g | 0.7 g | 0.7 g | 0.7 g | 0.7 g | 70 mg | 0.7 g |
|  | I-Arginine |  | 0.72 g | 0.72 g | 0.72 g | 0.72 g | 0.72 g | 0.72 g | 0.72 g | 72 mg | 0.72 g |
|  | I-Cysteine | 0.5 g | 0.2 g | 0.5 g | 0.5 g | 0.5 g | 0.5 g | 0.5 g | 0.5 g | 50 mg | 0.5 g |
|  | I-Glutamic acid |  | 0.6 g | 0.6 g | 0.6 g | 0.6 g | 0.6 g | 0.6 g | 0.6 g | 60 mg | 0.6 g |
|  | I-Phenylalanine |  | 0.4 g | 0.4 g | 0.4 g | 0.4 g | 0.4 g | 0.4 g | 0.4 g | 40 mg |  |
|  | I-Proline |  | 0.7 g | 0.7 g | 0.7 g | 0.7 g | 0.7 g | 0.7 g | 0.7 g | 70 mg | 0.7 g |
|  | I-Asparagine |  | 0.5 g | 0.5 g | 0.5 g | 0.5 g | 0.5 g | 0.5 g | 0.5 g | 50 mg | 0.5 g |
|  | I-Aspartic acid |  | 0.05 g | 0.05 g | 0.05 g | 0.05 g | 0.05 g | 0.05 g | 0.05 g | 5 mg | 0.05 g |
|  | I-Glutamine |  | 0.6 g | 0.6 g | 0.6 g | 0.6 g | 0.6 g | 0.6 g | 0.6 g | 60 mg | 0.6 g |
|  | I-Serine |  | 0.5 g | 0.5 g | 0.5 g | 0.5 g | 0.5 g | 0.5 g | 0.5 g | 50 mg | 0.5 g |
|  | I-Threonine |  | 0.5 g | 0.5 g | 0.5 g | 0.5 g | 0.5 g | 0.5 g | 0.5 g | 50 mg | 0.5 g |
|  | I-Alanine |  | 0.4 g | 0.4 g | 0.4 g | 0.4 g | 0.4 g | 0.4 g | 0.4 g | 40 mg | 0.4 g |
|  | Glycine |  | 0.3 g | 0.3 g | 0.3 g | 0.3 g | 0.3 g | 0.3 g | 0.3 g | 30 mg | 0.3 g |
|  | I-Lysine |  | 0.5 g | 0.5 g | 0.5 g | 0.5 g | 0.5 g | 0.5 g | 0.5 g | 50 mg | 0.5 g |
|  | I-Tryptophan |  | 0.2 g | 0.2 g | 0.2 g | 0.2 g | 0.2 g | 0.2 g | 0.2 g | 20 mg |  |
|  | I-Tyrosine |  | 0.3 g | 0.3 g | 0.3 g | 0.3 g | 0.3 g | 0.3 g | 0.3 g | 30 mg |  |
| Nucleotids | Adenine |  | 11 mg | 11 mg | 11 mg | 11 mg | 11 mg | 11 mg | 11 mg | 11 mg | 11 mg |
|  | Guanine |  | 5.6 mg | 5.6 mg | 5.6 mg | 5.6 mg | 5.6 mg | 5.6 mg | 5.6 mg | 5.6 mg | 5.6 mg |
|  | Uracil |  | 23 mg | 23 mg | 23 mg | 23 mg | 23 mg | 23 mg | 23 mg | 23 mg | 23 mg |
|  | Xanthine |  | 3.8 mg | 3.8 mg | 3.8 mg | 3.8 mg | 3.8 mg | 3.8 mg | 3.8 mg | 3.8 mg | 3.8 mg |

-continued

| | | | | | Media name | | | | | |
|---|---|---|---|---|---|---|---|---|---|---|---|
| | | dGMM | LAB | dGMM + LAB | dGMM + LAB low M/V | dGMM + LAB exclude SCFA | dGMM + LAB + only mono-sacharides | dGMM + LAB + Mucin | dGMM + LAB + only Mucin | dGMM + LAB + 10% amino-acids | dGMM + LAB exclude aromatic amino acids |
| Salts & Minerals | KCH3CO2 (Potassium acetate) | | 0.9 g | 0.9 g | 0.9 g | 0.9 g | 0.9 g | 0.9 g | 0.9 g | 0.9 g | 0.9 g |
| | FeSO4•7H2O | 1.4 mg | 4 mg | 4 mg | 1.4 mg | 4 mg | 4 mg | 4 mg | 4 mg | 4 mg | 4 mg |
| | MgCl2 | | 0.386 g | 0.386 g | 0.386 g | 0.386 g | 0.386 g | 0.386 g | 0.386 g | 0.386 g | 0.386 g |
| | ZnSO4•7 H2O | 1 mg | 5 mg | 5 mg | 1 mg | 5 mg | 5 mg | 5 mg | 5 mg | 5 mg | 5 mg |
| | Co(NO3)2•6H2O | 1 mg | | 1 mg | 1 mg | 1 mg | 1 mg | 1 mg | 1 mg | 1 mg | 1 mg |
| | AlK(SO4)2 (anhydrous) | 0.1 mg | | 0.1 mg | 0.1 mg | 0.1 mg | 0.1 mg | 0.1 mg | 0.1 mg | 0.1 mg | 0.1 mg |
| | Na2SeO3 (anhydrous) | 10 µg | | 10 µg | 10 µg | 10 µg | 10 µg | 10 µg | 10 µg | 10 µg | 10 µg |
| | Na2WO4•2H2O | 0.1 mg | | 0.1 mg | 0.1 mg | 0.1 mg | 0.1 mg | 0.1 mg | 0.1 mg | 0.1 mg | 0.1 mg |
| | NiCl2•6H2O | 0.2 mg | | 0.2 mg | 0.2 mg | 0.2 mg | 0.2 mg | 0.2 mg | 0.2 mg | 0.2 mg | 0.2 mg |
| | CaCl2 (anhydrous) | 9 mg | 30.2 mg | 30.2 mg | 9 mg | 30.2 mg | 30.2 mg | 30.2 mg | 30.2 mg | 30.2 mg | 30.2 mg |
| | CoCl2•6H2O | | 0.19 mg | 0.19 mg | 0.19 mg | 0.19 mg | 0.19 mg | 0.19 mg | 0.19 mg | 0.19 mg | 0.19 mg |
| | CuSO4 (anhydrous) | 0.064 mg | 0.12 mg | 0.12 mg | 0.064 mg | 0.12 mg | 0.12 mg | 0.12 mg | 0.12 mg | 0.12 mg | 0.12 mg |
| | H3BO3 | 0.1 mg | 0.75 mg | 0.75 mg | 0.1 mg | 0.75 mg | 0.75 mg | 0.75 mg | 0.75 mg | 0.75 mg | 0.75 mg |
| | KI | | 0.11 mg | 0.11 mg | 0.11 mg | 0.11 mg | 0.11 mg | 0.11 mg | 0.11 mg | 0.11 mg | 0.11 mg |
| | MnSO4•H2O | 5 mg | 0.11 mg | 5 mg | 5 mg | 5 mg | 5 mg | 5 mg | 5 mg | 5 mg | 5 mg |
| | (NH4)6Mo7O24•4H2O | | 0.19 mg | 0.19 mg | 0.19 mg | 0.19 mg | 0.19 mg | 0.19 mg | 0.19 mg | 0.19 mg | 0.19 mg |
| | K2SO4 | | 23 mg | 23 mg | 23 mg | 23 mg | 23 mg | 23 mg | 23 mg | 23 mg | 23 mg |
| | NaCl | 90 mg | 3 g | 3.01 g | 3.01 g | 3.01 g | 3.01 g | 0.81 g | 0.81 g | 3.01 g | 3.01 g |
| | Ammonium citrate dibasic | | 1.7 g | 1.7 g | 1.7 g | 1.7 g | 1.7 g | 1.7 g | 1.7 g | 1.7 g | 1.7 g |
| | FeCl3 | | 3 mg | 3 mg | 3 mg | 3 mg | 3 mg | 3 mg | 3 mg | 3 mg | 3 mg |
| | MgSO4•7 H2O | 30 mg | | 30 mg | 30 mg | 30 mg | 30 mg | 30 mg | 30 mg | 30 mg | 30 mg |
| | NaHCO3 | 0.4 g | | 0.4 g | 0.4 g | 0.4 g | 0.4 g | 0.4 g | 0.4 g | 0.4 g | 0.4 g |
| | Na2MoO4•2H2O | 0.1 mg | | 0.1 mg | 0.1 mg | 0.1 mg | 0.1 mg | 0.1 mg | 0.1 mg | 0.1 mg | 0.1 mg |
| Vitamins & Anti-oxidants | myo-Inositol | | 2 mg | 2 mg | 2 mg | 2 mg | 2 mg | 2 mg | 2 mg | 2 mg | 2 mg |
| | L-Glutathione reduced | | 15 mg | 15 mg | 15 mg | 15 mg | 15 mg | 15 mg | 15 mg | 15 mg | 15 mg |
| | Biotin | 20 µg | 6 mg | 6.02 mg | 20 µg | 6.02 mg | 6.02 mg | 6.02 mg | 6.02 mg | 6.02 mg | 6.02 mg |
| | Thiamine HCl | 50 µg | 0.56 mg | 0.56 mg | 50 µg | 0.56 mg | 0.56 mg | 0.56 mg | 0.56 mg | 0.56 mg | 0.56 mg |
| | Riboflavin | 50 µg | 0.9 mg | 0.9 mg | 50 µg | 0.9 mg | 0.9 mg | 0.9 mg | 0.9 mg | 0.9 mg | 0.9 mg |
| | Ascorbic acid | | 0.5 g | 0.5 g | 0.5 g | 0.5 g | 0.5 g | 0.5 g | 0.5 g | 0.5 g | 0.5 g |
| | Pyridoxamine · 2 HCl | | 5 mg | 5 mg | 5 mg | 5 mg | 5 mg | 5 mg | 5 mg | 5 mg | 5 mg |
| | Niacin | 50 µg | 0.9 mg | 0.9 mg | 50 µg | 0.9 mg | 0.9 mg | 0.9 mg | 0.9 mg | 0.9 mg | 0.9 mg |
| | Pyridoxine HCl | 0.1 mg | 4.8 mg | 4.8 mg | 0.1 mg | 4.8 mg | 4.8 mg | 4.8 mg | 4.8 mg | 4.8 mg | 4.8 mg |
| | Calcium Pantothenate | 50 µg | 1.2 mg | 1.2 mg | 50 µg | 1.2 mg | 1.2 mg | 1.2 mg | 1.2 mg | 1.57 mg | 1.57 mg |
| | Folic acid | 20 µg | 0.56 mg | 0.56 mg | 20 µg | 0.56 mg | 0.56 mg | 0.56 mg | 0.56 mg | 0.56 mg | 0.56 mg |
| | p-Aminobenzoic acid | 50 µg | 56 µg | 50 µg | 50 µg | 50 µg | 50 µg | 50 µg | 50 µg | 50 µg | 50 µg |
| | Lipoic acid | 50 µg | 1 mg | 1.05 mg | 1.05 mg | 1.05 mg | 1.05 mg | 1.05 mg | 1.05 mg | 1.05 mg | 1.05 mg |
| | Vitamin B12 | 1 µg | | 1 µg | 1 µg | 1 µg | 1 µg | 1 µg | 1 µg | 1 µg | 1 µg |
| | Vitamin K (menadione) | 1 mg | | 1 mg | 1 mg | 1 mg | 1 mg | 1 mg | 1 mg | 1 mg | 1 mg |
| SCFA | Acetic acid | 1.7 mL | | 1.7 mL | 1.7 mL | | 1.7 mL | 1.7 mL | 1.7 mL | 1.7 mL | 1.7 mL |
| | Isovaleric acid | 0.1 mL | | 0.1 mL | 0.1 mL | | 0.1 mL | 0.1 mL | 0.1 mL | 0.1 mL | 0.1 mL |
| | Propionic acid | 2 mL | | 2 mL | 2 mL | | 2 mL | 2 mL | 2 mL | 4 mL | 2 mL |
| | Butyric acid | 2 mL | | 2 mL | 2 mL | | 2 mL | 2 mL | 2 mL | 2 mL | 2 mL |
| Buffer compounds | KH2PO4 | 13.61 g | 3.1 g | 13.61 g | 3.11 g | 13.61 g | 13.61 g | 13.61 g | 13.61 g | 13.61 g | 13.61 g |
| | K2HPO4 | | 6.48 g | 6.48 g | 6.48 g | 6.48 g | 6.48 g | 6.48 g | 6.48 g | 6.48 g | 6.48 g |
| | Tricine | | 1.5 g | 1.5 g | 1.5 g | 1.5 g | 1.5 g | 1.5 g | 1.5 g | 1.5 g | 1.5 g |
| | EDTA [mg] | 5 | 7.34 | 12.34 | 12.34 | 12.34 | 12.34 | 12.34 | 12.34 | 12.34 | 12.34 |
| | Nitrilotriacetic acid [mg] | | 7.34 | 7.34 | 7.34 | 7.34 | 7.34 | 7.34 | 7.34 | 7.34 | 7.34 |

Table 3 shows the effect of media and pH on the in vitro assembly of a stable bacterial community. The numbers are relative abundances.

| | dGMM + LAB | | dGMM + LAB + Mucin | |
|---|---|---|---|---|
| | pH 5.5 | pH 7.0 | pH 5.5 | pH 7.0 |
| E. coli CFT073 | 0.000 | 0.000 | 0.000 | 0.000 |
| B. vulgatus | 0.000 | 0.000 | 0.000 | 0.090 |
| B. uniformis | 0.000 | 0.200 | 0.000 | 0.267 |
| B. fragilis | 0.000 | 0.021 | 0.015 | 4.316 |
| B. thetaiotaomicron | 0.008 | 0.065 | 0.000 | 6.610 |
| B. hansenii | 0.000 | 0.000 | 0.000 | 0.000 |
| C. ramosum | 0.020 | 31.068 | 0.081 | 28.092 |
| L. gasseri | 0.000 | 0.000 | 0.029 | 0.000 |
| E. rectale | 0.000 | 0.000 | 0.000 | 0.000 |
| B. crossotus | 0.000 | 0.000 | 0.000 | 0.000 |
| H. parainfluenzae | 0.000 | 0.000 | 0.000 | 0.000 |
| P. copri | 0.000 | 0.000 | 0.000 | 0.000 |
| P. melaninogenica | 0.000 | 0.000 | 0.000 | 0.000 |
| B. adolescentis | 0.000 | 0.000 | 0.023 | 0.000 |
| E. lenta | 0.000 | 0.004 | 0.000 | 0.018 |
| F. nucleatum subsp. nucleatum | 0.000 | 0.000 | 0.000 | 0.110 |
| C. bolteae | 0.000 | 0.000 | 0.014 | 1.900 |
| B. longum subsp. longum | 0.000 | 0.000 | 0.000 | 0.004 |
| F. nucleatum subsp. animalis | 0.000 | 0.000 | 0.000 | 0.000 |
| C. perfringens 756 | 0.000 | 1.614 | 0.033 | 3.606 |
| D. piger | 0.000 | 0.000 | 0.000 | 0.000 |
| C. saccharolyticum | 0.000 | 0.193 | 0.000 | 0.061 |
| S. salivarius | 0.021 | 53.887 | 0.094 | 32.211 |
| E. siraeum | 0.000 | 0.000 | 0.000 | 0.000 |
| L. paracasei | 90.617 | 8.144 | 78.272 | 10.857 |
| B. animalis subsp. lactis BI-07 | 0.000 | 0.000 | 0.000 | 0.000 |
| R. gnavus | 0.000 | 0.000 | 0.000 | 0.000 |
| C. comes | 0.000 | 0.371 | 0.057 | 7.577 |
| E. coli IAI1 | 0.041 | 3.333 | 0.059 | 3.254 |
| C. difficile | 0.000 | 0.720 | 0.000 | 0.520 |
| S. sonnei | 0.000 | 0.000 | 0.000 | 0.000 |
| L. lactis | 0.000 | 0.000 | 0.000 | 0.107 |
| L. plantarum | 9.293 | 0.249 | 21.323 | 0.063 |
| S. typhimurium LT2 | 0.000 | 0.131 | 0.000 | 0.337 |
| V. cholerae N16961 | 0.000 | 0.000 | 0.000 | 0.000 |

The invention claimed is:

1. An in-vitro model of the human gut microbiome, comprising a panel consisting of bacterial species selected from *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella*, and *Bilophila*, and a medium kit for culturing bacteria of the human gut microbiome, wherein the medium kit comprises at least one of defined gut microbiota medium (dGMM), lactic acid bacteria (LAB) medium, dGMM and LAB medium, dGMM and LAB medium comprising a reduced amount of minerals and vitamins, dGMM and LAB medium excluding short chain fatty acids (SCFA), dGMM and LAB medium comprising monosaccharides as only carbohydrate source, dGMM and LAB medium comprising Mucin, dGMM and LAB medium comprising Mucin as only carbohydrate source, dGMM and LAB medium comprising only 10% amino acids, and dGMM and LAB medium excluding aromatic amino acids, and wherein said panel has a cumulative enzymatic coverage of more than 85% of the gut microbiome of a healthy human.

2. The in-vitro model according to claim 1, wherein said species is selected from *Bacteroides caccae, Bacteroides clarus, Bacteroides coprocola, Bacteroides dorei* or *Bacteroides vulgatus, Bacteroides eggerthii, Bacteroides fragilis, Bacteroides ovatus, Bacteroides thetaiotaomicron, Bacteroides xylanisolvens, Bacteroides stercoris, Bacteroides uni-*

*formis, Eubacterium eligens, Eubacterium rectale, Eubacterium siraeum, Alistipes putredinis, Alistipes shahii, Ruminococcus gnavus, Ruminococcus torques, Ruminococcus bromii, Ruminococcus obeum, Roseburia hominis, Roseburia intestinalis, Parabacteroides distasonis, Parabacteroides merdae, Prevotella copri, Bifidobacterium adolescentis, Bifidobacterium longum, Coprococcus comes, Dorea formicigenerans, Blautia hansenii, Odoribacter splanchnicus, Clostridium bolteae, Clostridium leptum, Clostridium ramosum, Streptococcus parasanguinis, Streptococcus salivarius, Collinsella aerofaciens*, and *Bilophila wadsworthia.*

3. The in-vitro model according to claim 1, the medium kit for culturing bacteria of the human gut microbiome, comprising at least one of defined gut microbiota medium (dGMM) and LAB medium, dGMM and LAB medium comprising a reduced amount of minerals and vitamins, dGMM and LAB medium excluding short chain fatty acids (SCFA), dGMM and LAB medium comprising monosaccharides as only carbohydrate source, dGMM and LAB medium comprising Mucin, dGMM and LAB medium comprising Mucin as only carbohydrate source, dGMM and LAB medium comprising only 10% amino acids, and dGMM and LAB medium excluding aromatic amino acids.

4. The in-vitro model according to claim 1, wherein the medium kit for culturing bacteria of the human gut microbiome comprises one of dGMM and LAB medium comprising a reduced amount of minerals and vitamins, dGMM and LAB medium excluding short chain fatty acids (SCFA), dGMM and LAB medium comprising monosaccharides as the only carbohydrate source, dGMM and LAB medium comprising Mucin, dGMM and LAB medium comprising Mucin as the only carbohydrate source, dGMM and LAB medium comprising only 10% amino acids, and dGMM and LAB medium excluding aromatic amino acids.

5. The in-vitro model according to claim 1, the medium kit for culturing bacteria of the human gut microbiome comprising one of dGMM and LAB medium excluding short chain fatty acids (SCFA), dGMM and LAB medium comprising monosaccharides as the only carbohydrate source, dGMM and LAB medium comprising Mucin as the only carbohydrate source, dGMM and LAB medium comprising only 10% amino acids, and dGMM and LAB medium excluding aromatic amino acids.

6. The in-vitro model according to claim 1, the dGMM being gut microbiota medium (GMM) excluding yeast and meat extract.

7. A method for determining the effect of at least one compound on the human gut microbiome, comprising the steps of a) providing an in-vitro model of the human gut microbiome according to claim 1;

b) providing at least one compound to be tested;

c) culturing said in-vitro model in the presence of said compound in vitro;

d) determining the bacterial growth in said in-vitro model; and e) determining the effect of said at least one compound on said human gut microbiome comprising comparing said growth to a control culture.

8. The method according to claim 7, wherein said compound is a food ingredient, a food additive, a drink additive, a food supplement, a drink supplement, a dietary supplement, a food flavor, a flavor enhancer, a nutritional product, a bioactive ingredient, a medical food, a cosmetic product, an herbal product, a therapeutic compound, a pharmaceutical compound, a pharmaceutical additive, an antimicrobial and/or immune enhancer, an antioxidant, an antibiotic, an immunosuppressant, a natural product, a bioactive compound, a protein, an amino acid, a manufactured product, a processed product, a synthetic product, and/or a preservative, optionally wherein said effect of said at least one compound on the human gut microbiome is determined to predict a side effect of said at least one compound on a human subject.

9. A method for diagnosing a disorder in a human subject, comprising a) providing an in-vitro model of the gut microbiome of said subject comprising a panel of bacterial species selected from *Bacteroides, Eubacterium, Alistipes, Ruminococcus, Roseburia, Parabacteroides, Prevotella, Bifidobacterium, Coprococcus, Dorea, Blautia, Odoribacter, Clostridium, Streptococcus, Collinsella, and Bilophila;* b) providing an in-vitro model of the gut microbiome according to claim 1;

c) culturing said in-vitro model from a) and culturing said in-vitro model from b), and e) comparing said bacterial growths, wherein a difference in said bacterial growths is indicative for a disorder in said subject.

10. The method according to claim 9, wherein said disorder is selected from a gastrointestinal disorder, a proliferative disease, a metabolic disorder, a cardiovascular disease, an immunological disease, and an infectious disease.

11. The method according to claim 10, wherein said disorder is selected from the group consisting of a gastrointestinal motility disorder, irritable bowel syndrome, constipation, a functional gastrointestinal disorder, gastroesophageal reflux disease, functional heartburn, dyspepsia, functional dyspepsia, nonulcer dyspepsia, gastroparesis, chronic intestinal pseudo-obstruction, colonic pseudo-obstruction, Crohn's disease, colitis, ulcerative colitis, inflammatory bowel disease, diverticulitis, gluten and/or lactose intolerance, stomach rumble, meteorism, flatulence, atherosclerosis, rheumatoid arthritis, and a cancer disease.

\*   \*   \*   \*   \*